US011084860B2

(12) United States Patent
Donahoe et al.

(10) Patent No.: US 11,084,860 B2
(45) Date of Patent: Aug. 10, 2021

(54) MODIFIED MULLERIAN INHIBITING SUBSTANCE (MIS) PROTEINS AND USES THEREOF FOR THE TREATMENT OF DISEASES

(71) Applicants: THE GENERAL HOSPITAL CORPORATION, Boston, MA (US); MASSACHUSETTS EYE AND EAR INFIRMARY, Boston, MA (US)

(72) Inventors: Patricia K. Donahoe, Boston, MA (US); Demetrios Vavvas, Boston, MA (US); David Pepin, Somerville, MA (US); Mien Van Hoang, Braintree, MA (US)

(73) Assignees: THE GENERAL HOSPITAL CORPORATION, Boston, MA (US); MASSACHUSETTS EYE AND EAR INFIRMARY, Boston, MA (US)

(*) Notice: Subject to any disclaimer, the term of this patent is extended or adjusted under 35 U.S.C. 154(b) by 0 days.

(21) Appl. No.: 14/773,936

(22) PCT Filed: Mar. 12, 2014

(86) PCT No.: PCT/US2014/024010
§ 371 (c)(1),
(2) Date: Sep. 9, 2015

(87) PCT Pub. No.: WO2014/164981
PCT Pub. Date: Oct. 9, 2014

(65) Prior Publication Data
US 2016/0039898 A1 Feb. 11, 2016

Related U.S. Application Data

(60) Provisional application No. 61/777,135, filed on Mar. 12, 2013.

(51) Int. Cl.
| | | |
|---|---|---|
| *A61K 38/00* | (2006.01) | |
| *A61K 38/22* | (2006.01) | |
| *C07K 14/765* | (2006.01) | |
| *C07K 14/575* | (2006.01) | |
| *A61P 15/08* | (2006.01) | |
| *A61P 5/28* | (2006.01) | |
| *A61K 45/06* | (2006.01) | |
| *A61K 31/416* | (2006.01) | |

(52) U.S. Cl.
CPC .......... *C07K 14/575* (2013.01); *A61K 31/416* (2013.01); *A61K 45/06* (2013.01); *C07K 14/765* (2013.01); *A61K 38/00* (2013.01); *C07K 2319/43* (2013.01); *C07K 2319/50* (2013.01); *Y02A 50/30* (2018.01)

(58) Field of Classification Search
CPC ...... A61K 38/00; A61K 38/22; C07K 14/765; C07K 14/575; C07K 2319/00; C07K 2319/43; C07K 2319/50; A61P 15/08; A61P 5/28
See application file for complete search history.

(56) References Cited

U.S. PATENT DOCUMENTS

| | | |
|---|---|---|
| 4,753,794 A | 6/1988 | Donahoe |
| 5,010,055 A | 4/1991 | Donahoe |
| 5,661,126 A | 8/1997 | Donahoe et al. |
| 5,759,802 A | 6/1998 | Maki et al. |
| 6,428,978 B1* | 8/2002 | Olsen .................. C07K 14/765 435/69.1 |
| 6,673,352 B1 | 1/2004 | Donahoe |
| 2003/0124620 A1 | 7/2003 | Seifer |
| 2004/0062750 A1 | 4/2004 | Donahoe |

(Continued)

FOREIGN PATENT DOCUMENTS

| | | |
|---|---|---|
| EP | 1074265 A1 | 2/2001 |
| WO | 88/00054 A1 | 1/1988 |

(Continued)

OTHER PUBLICATIONS

Bordo, D., et al. Suggestions for "safe" residue substitutions in site-directed mutagenesis. Journal of Molecular Biology, 1991,217: 721-729.*
Papakostas et al., "Development of an efficiently cleaved, bioactive, highly pure FLAG-tagged recombinant human Mullerian Inhibiting Substance" Protein Expression and Purification 70:32-38 (2010).
Pieretti-Vanmarcke et al., "Mullerian Inhibiting Substance enhances subclinical doses of chemotherapeutic agents to inhibit human and mouse ovarian cancer" PNAS 103(46):17426-17431 (2006).
Zou et al., "Overexpression of human transforming growth factor-β1 using a recombinant CHO cell expression system" Protein Expression and Purification 37:265-272 (2004).

(Continued)

*Primary Examiner* — Vanessa L. Ford
*Assistant Examiner* — Bruce D. Hissong
(74) *Attorney, Agent, or Firm* — Nixon Peabody LLP; David S. Resnick; Susanna C. Benn

(57) ABSTRACT

The present invention relates to modified recombinant human MIS protein which has improved cleavage and increased bioactivity and increased potency as compared to wild-type human MIS protein. Other aspects of the invention relate to methods to prevent and treat cancers, such as cancers that express the MIS receptor type II (MISRII) by administering to a subject a composition comprising a recombinant human MIS protein. Another aspect of the present invention relates to methods to lower plasma androgen levels in a subject, and/or for the treatment of a subject with a disease characterized by excess androgen. Another aspect provides pharmaceutical compositions and kits and methods for use comprising a recombinant human MIS protein. Another aspect of the present invention relates to methods to decrease the dose of a chemotherapeutic agent by administering the chemotherapeutic agent with the recombinant MIS protein that lowers the effective dose of the chemotherapeutic agent.

14 Claims, 6 Drawing Sheets
Specification includes a Sequence Listing.

(56) References Cited

U.S. PATENT DOCUMENTS

| | | | |
|---|---|---|---|
| 2005/0186664 A1* | 8/2005 | Rosen | A61K 38/04 435/69.7 |
| 2006/0216294 A1 | 9/2006 | McLennan | |
| 2009/0304675 A1 | 12/2009 | McLennan | |
| 2010/0233689 A1 | 9/2010 | Teixeira et al. | |
| 2013/0189327 A1 | 7/2013 | Ortega | |
| 2016/0310574 A1 | 10/2016 | Donahoe et al. | |

FOREIGN PATENT DOCUMENTS

| | | | |
|---|---|---|---|
| WO | 1989/006695 | A1 | 7/1989 |
| WO | 1992/013951 | A1 | 8/1992 |
| WO | 2001/008695 | A2 | 2/2001 |
| WO | 2001/019387 | A1 | 3/2001 |
| WO | 2003016514 | A1 | 2/2003 |
| WO | 2005/030963 | A1 | 4/2005 |
| WO | 2009/012357 | A2 | 1/2009 |
| WO | 2015/041718 | A1 | 3/2015 |
| WO | 2014/16498 | A1 | 10/2017 |

OTHER PUBLICATIONS

Benatar et al., "Lost in translation: treatment trials in the SOD1 mouse and in human ALS", Neurobiol Dis 26(1) 1-13 (2007).

Dibernardo et al., "Translating preclinical insights into effective human trials in ALS", Biochim Biophys Acta 1762 (11-12) 1139-1149 (2006).

Kano et al., "AMH/MIS as a contraceptive that protects the ovarian reserve during chemotherapy", Proc Natl Acad Sci USA 114(9) E1688-E1697 (2017).

Kurian et al., "Cleavage of Müllerian inhibiting substance activates antiproliferative effects in vivo", Clin Cancer Res 1 (3) 343-349 (1995).

Depin et al., "An albumin leader sequence coupled with a cleavage site modification enhances the yield of recombinant C-terminal Mullerian Inhibiting Substance", Technology 1(1) 63-71 (2013).

Search result generated on May 17, 2017 shows SEQ ID No. 3 integrated into UniProtKB/Swiss-Prot in 1986; 4 pages total.

Skaar et al., "Proteolytically activated, recombinant anti-mullerian hormone inhibits androgen secretion, proliferation, and differentiation of spermatogonia in adult zebrafish testis organ cultures", Endocrinology 152(9) 3527-3540 (2011).

Behringer et al., "Abnormal sexual development in transgenic mice chronically expressing Mullerian inhibiting susbstance", Nature 345(6271):167-170 (1990).

Durlinger et al., "Control of Primordial Follicle Recruitment by Anti-Mullerian Hormone in the Mouse Ovary", Endocrinology 140(12):5789-5796 (1999).

Durlinger et al., "Anti-Mullerian Hormone Inhibits Initiation of Primordial Follicle Growth in the Mouse Ovary", Endocrinology 143(3):1076-1084 (2002).

Maclaughlin et al., "Müllerian inhibiting substance/anti-Müllerian hormone: a potential therapeutic agent for human ovarian and other cancers", Future Oncol, 6(3):391-405 (2010).

Teixeira et al., "Müllerian-Inhibiting Substance Regulates Androgen Synthesis at the Transcriptional Level", Endocrinology 140(10):4732-4738 (1999).

UniProtKB MIZ-Human [online] [Retrieved on Jun. 10, 2016]. Web. <URL:http:uniprot.org/uniprot/P03971.txt?version=138. (Nov. 30, 2010) Entire Document.

Clowse et al., "Ovarian Preservation by GnRH Agonists during Chemotherapy: A Meta-Analysis", Journal of Women's Health 18(3):311-319 (2009).

Carter et al., "Fusion partners can increase the expression of recombinant interleukins via transient transfection in 2936E cells", Protein Sci 19(2) 357-362 (2010).

Meada et al., "Efficient production of active TNF-alpha by albumin signal peptide", Biochem Mol Biol Int 42(4) 825-832 (1997).

Sanfujin-ka Tiryo (Obstetrics and gynecology treatment), 2011, vol. 102, p. 547-551.

Jafarlou et al. "An Overview of the History, Applications, Advantages, Disadvantages and Prospects of Gene Therapy." Journal of Biological Regulators & Homeostatic Agents 30(2): 315-321 (2016).

Nachtigal et al. "Bioactivation of Mullerian inhibiting substance during gonadal development by a kex2/subtilisin-like endoprotease." Proc. Natl. Acad. Sci. USA 93(15): 7711-7716 (1996).

Nakayama. "Furin: a mammalian subtilisin/Kex2p-like endoprotease involved in processing of a wide variety of precursor proteins." Biochem. J. 327(3): 625-635 (1997).

Phillips. "The challenge of gene therapy and DNA delivery." Journal of Pharmacy and Pharmacology. 53(9): 1169-1174 (2001).

Shulman. "Mullerian Anomalies." Clinical Obstetrics and Gynecology 51(1): 214-222 (2008).

Winkler. "Oglionucleotide conjugates for therapeutic applications." Ther. Deliv. 4(7): 791-809 (2013).

Bhattacharya et al., "Impact of genetic variation on three dimensional structure and function of proteins", PLoS One (2017) , 12 (3) :e017355, p. 1-22.

* cited by examiner

LEADER SEQUENCE ALIGNMENT

```
            10        20
MIS 25  MRDLPLTSLALVLSALGALLGTEAL    ← MIS LEADER 25AA
         :  .  .  ::  ...:.  .  ::       (SEQ ID NO: 25)
HSAL    MKWVTFISLLFLFSSAYSR-GVFRR    ← HSA LEADER 24AA
            10        20                 (SEQ ID NO: 6)
```

20% IDENTITY
5 CONSERVED AA (Conventional Numbering)

mrdlpltsla lvlsalgall gtealraeep avgtsglifr edldwppgsp qeplclvalg 60 (35)
LEADER SEQUENCE (1-25 of SEQ ID NO:1)

gdsngssspl rvvgalsaye qaflgavgra rwgprdlatf gvcntgdrqa alpslrrlga 120 (95)

wlrdpgggrl vvlhleevtw eptpslrfqe pppggagppe lallvlypgp gpevtvtrag 180 (155)

lpgaqslcps rdtrylvlav drpagawrgs glaltlqprg edsrlstarl qallfgddhr 240 (215)

cftrmtpall llpr s epapl pahgqldtvp fppprpsael eesppsadpf letltrlvra 300 (275)
Secondary cleavage site (254/255 of SEQ ID NO: 1)

lrvpparasa prlaldpdal agfpqglvnl sdpaalerll dgeeplllll rptaattgdp 360 (335)

aplhdptsap watalarrva aelqaaaael rslpglppat apllarllal cpggpgglgd 420 (395)

plralllka lgglrvewrg rdprgpg raq rs agataadg pcalrelsvd lraersvlip 480 (455)
Primary cleavage recognition sequence (448-452 of SEQ ID NO: 1)

etyqanncqg vcgwpqsdrn prygnhvvll lkmqvrgaal arppccvpta yagkllisls 540 (515)

eerisahhvp nmvatecgcr 560 (535)    (SEQ ID NO:1)

FIG. 5A

| | LOCATION ON SEQ ID NO: 1 | LOCATION ON NORMAL NOMENCLATURE OF MIS (FIRST AMINO ACID IS AFTER THE LEADER SEQUENCE) |
|---|---|---|
| LEADER SEQUENCE: | 1-25 | AMINO ACID RESIDUES -24-0 |
| PRIMARY CLEAVAGE RECOGNITION SEQUENCE | 448-452 (RAQR/S) | 423-427 |
| PRIMARY CLEAVAGE SITE | BETWEEN 451 AND 452 (451/452) | BETWEEN 426 AND 427 (426/427) |
| CHANGE OF PRIMARY CLEAVAGE RECOGNITION SEQUENCE | CHANGE OF AMINO ACID 450 FROM a Q TO an R (Q450R) | CHANGE OF AMINO ACID 425 FROM a Q TO an R (Q425R) |
| SECONDARY CLEAVAGE RECOGNITION SITE | BETWEEN 254 AND 255 (254/255) | BETWEEN 229 AND 230 (

MODIFIED MULLERIAN INHIBITING SUBSTANCE (MIS) PROTEINS AND USES THEREOF FOR THE TREATMENT OF DISEASES

CROSS REFERENCE TO RELATED APPLICATIONS

This application is a 371 National Phase Entry of International Patent Application No. PCT/US2014/024010 filed on Mar. 12, 2014 which claims benefit under 35 U.S.C. § 119(e) of U.S. Provisional Application No. 61/777,135 filed Mar. 12, 2013, the contents of which are incorporated herein by reference in their entirety.

GOVERNMENT SUPPORT

This invention was made with government support under grant Number CA17393 awarded by the National Institutes of Health (NIH). The Government has certain rights in the invention.

SEQUENCE LISTING

The instant application contains a Sequence Listing which has been submitted electronically in ASCII format and is hereby incorporated by reference in its entirety. Said ASCII copy, created on Sep. 3, 2015, is named 030258-076964-PCT_SL.txt and is 28,114 bytes in size.

FIELD OF THE INVENTION

The present invention relates to modified recombinant human MIS protein which has improved cleavage and increased bioactivity and increased potency as compared to wild-type human MIS protein. In some aspects, the recombinant human MIS protein comprises at least one of the following: a modified Kex cleavage site for increased cleavage, a FLAG Tag, and a non-MIS leader sequence in place of the normal MIS leader sequence. Other aspects of the invention relate to methods, uses and kits comprising a recombinant human MIS protein for the treatment of cancers, such as those that expresses the MIS receptor type II (MISRII) or for the treatment of a disease characterized by excess androgen.

BACKGROUND OF THE INVENTION

Mullerian Inhibiting Substance (MIS) also known as anti-Mullerian hormone (AMH), is a 140-kDa disulfide-linked homodimer glycoprotein member of the large transforming growth factor-β (TGFβ) multigene family of glycoproteins. The proteins in this gene family are all produced as dimeric precursors and undergo posttranslational processing for activation, requiring cleavage and dissociation to release bioactive C-terminal fragments. Similarly, the 140 kilodalton (kDa) disulfide-linked homodimer of MIS is proteolytically cleaved to generate its active C-terminal fragments.

The human MIS gene is located on chromosome 19, and its expression is sexually dimorphic. In males, MIS expression begins at 9 weeks gestation in the fetal testes and continues at high levels until puberty, when expression levels fall dramatically. In females, MIS is produced only postnatally in granulosa cells from prepuberty through menopause at levels similar to adult males, after which expression ceases. In male fetuses MIS causes regression of the Mullerian ducts, the precursors to the Fallopian tubes, uterus, cervix, and upper third of the vagina.

MIS exerts its biologic effect after binding to a heterodimer of type I and type II single transmembrane spanning serine threonine kinase receptors, leading to cross phosphorylation of the GS box kinase domain of the type I receptor by the type II receptor. Subsequently, SMAD 1, 5 and 8 (but predominantly SMAD 8) are activated and, together with SMAD 4, regulate gene transcription. Only one MIS receptor type II (MISRII) gene has been identified in mice, rats, and rabbits, where in humans its gene localizes to chromosome 12. It is a 65-kDa protein which has been detected in embryonic and adult Mullerian structures, breast tissue, prostatic tissue, the gonads, motor neurons, and brain. In the fetus, mesoepithelial cells expressing MISRII in the coelomic epithelium covering the urogenital ridge migrate into and become part of the mesenchymal cells surrounding the Mullerian duct epithelium. Expression is also detected in the gonads, as wells as in the ovarian coelomic epithelium. Type I MIS receptors have been identified in mammals, with activin receptor-like kinase (ALK) 2 and 3 being the most likely candidates, depending upon animal species and the tissue examined.

In addition to its well established role in the regression of Mullerian ducts, MIS inhibits the proliferation of various human cancer cell lines in vitro and in vivo. The cell lines showing inhibition were derived from ovarian, cervical, endometrial, prostate and breast cancers. Toxicity has not been observed in vivo even when high concentrations of MIS are maintained systemically in rodents or in human patients with tumors secreting MIS for prolonged periods of time. These findings of relatively restricted receptor expression, anti-proliferative activity against cancer cells expressing the MIS RI and RII, and its apparent non-toxicity, taken together, make MIS an ideal reagent for use in combination with existing chemotherapeutic drugs for the treatment of ovarian cancer, which are known to become resistant to these conventional agents.

MIS acts through MIS Type II receptor cells to serve as a potent tumor suppressor of ovarian cancer initiation (Teixeira et al, unpublished). MIS can also target, as a receptor mediated event the stem/progenitor population of the ovarian cancer cell line (Meirelles et al, 2012; Wei et al, 2010). MIS can be used for the treatment of cancers, for example, expressing MISRII. MISRII is expressed in the majority of epithelial ovarian cancers (Masiakos et al. 1999; Bakkum-Gamez et al. 2008; Song et al. 2009).

MIS also inhibits growth of a variety of cancers in vitro and in vivo, without obvious toxicity after prolonged therapy in vivo (Pieretti-Vanmarcke et al. 2006b). Epithelial ovarian cancer recapitulates the original histology of the embryonic Mullerian ducts and its various subtypes (Scully 1977); for example, serous cystadenocarcinoma resembles embryonic Fallopian tube, endometrioid carcinoma, the endometrium, and mucinous carcinoma, the cervix. Also, MIS acts synergistically or additively with commonly used cancer drugs to control tumor growth (Pieretti-Vanmarcke et al. 2006a).

It has been previously reported that chemotherapeutic agents select for ovarian cancer stem cells, which are typically multi-drug resistant, and/or resistant to chemotherapeutics. In particular, there is a growing body of research reporting that ovarian cancers and cell lines are heterogeneous, with ovarian cancer stem cell populations that are resistant to chemotherapeutic drugs but remain responsive to MIS. MIS particularly targets ovarian cancer side population cells and a population of CD44+, CD24+, EpCam+ and E-Cadherin-negative cells with stem/progenitor characteristics that respond poorly to chemotherapeutic agents currently in clinical use for ovarian cancer (Wei et al, 2010). In particular, MIS has been shown to inhibit ovarian cancer cells both in-vitro and in-vivo and can specifically target and inhibit the growth of an ovarian cancer progenitor cell population enriched by the CD44+, CD24+, Ep-CAM+ and E-cadherin– cell surface markers. In order to accommodate clinical testing of MIS in ovarian cancer patients, the production of recombinant human MIS must be optimized to increase yield and purity.

However, the preparation resulting from purification of native or wild-type MIS is complex and the yield is low. Furthermore, the cleavage necessary to produce the active fragment of MIS is also inefficient. Human MIS protein is produced from a pre-proprotein, which comprises a leader sequence. The leader sequence (amino acids 1-25 of SEQ ID NO: 1) is cleaved off and the remaining preprotein (often called "holo-human MIS") must be post-translationally cleaved to result in a N-terminal and C-terminal domain. These covalently linked N-terminal and C-terminal domains form a monomer, and two identical monomers (comprising the N- and C-terminal domains) form together to generate a homodimer Holo-human MIS is cleaved into its N- and C-terminal domains most likely by means of furin or a related prohormone convertase PC5, expressed in the gonads. Cleavage occurs primarily at a kex-like site characterized by $R^{-4} XXR^{-1}$ with a serine in the +1 site, which makes the MIS cleavage site monobasic. The purified C-terminal domain is the biologically active moiety and cleavage is required for biological activity. A secondary cleavage site, whose significance is unknown, is observed less frequently at residues 229-230 (which corresponds to amino acid residues 254-255 of SEQ ID NO:1). Non-cleavable mutants of MIS are not biologically active and mutations in the human gene that truncate the carboxy-terminal domain lead to persistent Mullerian duct syndrome. The role of the amino-terminal domain in vivo may be to assist in protein folding and to facilitate delivery of the C-terminal peptide to its receptor. In one study (Cate, Pepinsky, et al.) addition of the N-terminal peptide was shown to enhance the biological activity of the C-terminal moiety in vitro, but the mechanism was unclear. The cleavage of recombinant MIS expressed by CHO cells is incomplete, thus cleavage with an exogenous serine protease such as plasmin is required to enhance bioactivity.

Accordingly, there is a need for a more efficient method to produce high concentrations of human MIS protein for use as a therapeutic biologic agent.

SUMMARY OF THE INVENTION

The present invention relates to modified recombinant human MIS protein which has improved cleavage and increased bioactivity and increased potency as compared to wild-type human MIS protein, where the recombinant human MIS protein comprises a combination of the following: a modified Kex cleavage site for increased cleavage, and a non-MIS leader sequence in place of the normal MIS leader sequence, to improve the yield of bioactive protein with or without an, internal label, or Tag to facilitate its purification.

Accordingly, herein the inventors have engineered changes to the native human MIS amino acid sequence to do a combination of the following: (i) modify the primary cleavage site to increase cleavage and thus increase the potency and bioactivity of MIS, without insertion of a tag to facilitate its purification, and (ii) modify the endogenous leader sequence of MIS to increase yield of bioactive protein. Surprisingly, the addition of the leader sequence in combination with a modified primary cleavage site significantly increased both the yield of protein produced and the amount of cleavage from the primary cleavage site of the recombinant MIS protein. Furthermore, there is an unmet need to have a form of bioactive MIS that is labeled for use in receptor and other binding studies that will be very important both for the selection of patients for treatment and for addressing molecular mechanistic questions regarding the interaction of MIS in various receptor bearing tissues. In addition, the labeled ligand will be essential to determine if another receptor or other binding proteins exist in various tissues. Herein, the inventors demonstrate the production of an internally epitope tagged MIS that retains full bioactivity in the Mullerian duct regression assay. In one embodiment, the tag is a "FLAG" tag because of the availability of high quality reagents used for its detection and purification.

Herein, the inventors demonstrate that substitution of the MIS leader sequence to that of human serum albumin (HSA), combined with a modification of the primary endogenous cleavage site from RAQR/S (SEQ ID NO: 26) to RARR/S (SEQ ID NO: 27) results in greater expression, increased c-terminus cleavage and a reduction in unwanted cryptic internal cleavage when produced in CHO cells. Purified MIS containing these alterations retains its capacity to induce regression of the Mullerian duct in fetal rat embryonic urogenital ridge assays, and shows increased potency.

In another embodiment, the recombinant human MIS is engineered with a more efficient cleavage site at the carboxy-terminal end of the N-terminal domain, thereby eliminating the need for exogenous cleavage. This recombinant MIS protein can be used both as a therapeutic and as a probing molecule, without a tag for identification.

Importantly, the change in the endogenous leader sequence with another leader sequence, e.g., a human serum albumin (HSA) leader sequence increased production of the MIS protein. Surprisingly, the inventors demonstrate that the combination of the leader sequence and modified cleavage site increases cleavage from the primary cleavage site from 37% to over 80% which was unexpected, as an increase in protein yield is normally associated with decreased post-translational processing, including cleavage, because increased protein production typically saturates the available or endogeneous cleavage enzymes.

Accordingly, the present invention relates to a method of using a recombinant human MIS protein (e.g., the polypeptide and/or the nucleic acid encoding a recombinant human MIS protein) or a functional fragment or derivative or variant thereof to treat cancer, for example, a cancer which expresses the MIS receptor II (MISRII).

Accordingly, one aspect of the present invention relates to a recombinant Mullerian Inhibiting Substance (MIS) protein comprising a combination of a non-MIS leader sequence or a functional fragment thereof in place of the MIS leader sequence of amino acids 1-25 of SEQ ID NO: 1, and a modification of at least one amino acid between residues 448-452 of SEQ ID NO: 1 to increase cleavage as compared to in the absence of a modification, wherein the recombinant MIS protein has increased cleavage and increased yield of production in vitro as compared to wild-type MIS protein corresponding to amino acid residues of SEQ ID NO: 1. In some embodiments, the recombinant MIS protein lacks a leader sequence. In these embodiments, the recombinant MIS protein can be produced from a pre-proprotein comprising a non-MIS leader sequence or a functional fragment thereof in place of the MIS leader sequence of amino acids 1-25 of SEQ ID NO: 1, wherein the leader sequence is cleaved off during production. In some embodiments, the recombinant MIS protein further comprises a Tag protein.

In some embodiments, a non-MIS leader sequence is an albumin leader sequence or a functional fragment thereof, for example, a human serum albumin (HSA) leader sequence or a fragment thereof. In some embodiments, the HSA leader sequence comprises the amino acid sequence of SEQ ID NO: 6 or a variant that is at least 80% homologous thereto, or a functional fragment, e.g., a fragment of the HSA sequence comprising at least 10 amino acids, or at least about 11, or at least 15 amino acids of SEQ ID NO: 6 or a variant that is at least 80% homologous thereto. In some embodiments, a fragment of the HSA leader sequence is selected from the group consisting of: MKWVTFISLLFLF-SSAYS (SEQ ID NO: 13); MKWVTFISLLFLFSSAY-SRGVFRR (SEQ ID NO: 6); MKWVSFISLLFLFSSAYS (SEQ ID NO:14).

In some embodiments, a non-MIS leader sequence is selected from a group consisting of: immunoglobulin signal peptide fused to a tissue-type plasminogen activator propeptide (IgSP-tPA), murine immunoglobulin signal peptide (IgSP), a MPIF-1 signal sequence (MKVSVAALSCLMLVTALGSQA (SEQ ID NO: 15); a stanniocalcin signal sequence (MLQNSAVLLLLVISASA (SEQ ID NO:16); an invertase signal sequence (MLLQAFLFLLAGFAAKISA (SEQ ID NO:17); a yeast mating factor alpha signal sequence (*K. lactis* killer toxin leader sequence); a hybrid signal sequence (MKWVSFIS-LLFLFSSAYSRSLEKR (SEQ ID NO:18)); a HSA/MFα-1 hybrid signal sequence (MKWVSFISLLFLFSSAY-SRSLDKR (SEQ ID NO:19)); a *K. lactis* killer/MFα-1 fusion leader sequence (MNIFYIFLFLLSFVQGSLDKR (SEQ ID NO:20)); an immunoglobulin Ig signal sequence (MGWSCIILFLVATATGVHS (SEQ ID NO:21)); a Fibulin B precursor signal sequence (MERAAPSRRVPLPLLLLG-GLALLAAGVDA (SEQ ID NO:22)); a clusterin precursor signal sequence (MMKTLLLFVGLLLTWESGQVLG (SEQ ID NO: 23)); and the insulin-like growth factor-binding protein 4 signal sequence (MLPLCLVAALL-LAAGPGPSLG (SEQ ID NO:24)) or a functional fragment thereof.

In some embodiments, a modification of amino acid 450 of SEQ ID NO: 1 from Q to R increases the cleavage from the primary cleavage site in MIS as compared to the amount of cleavage in the absence of such a modification. In some embodiments, a recombinant MIS further comprises a modification of amino acid 452 of SEQ ID NO: 1 from S to R to increase cleavage as compared to in the absence of such a modification.

In some embodiments, the recombinant MIS protein disclosed herein comprises a tag which is a FLAG tag, for example, amino acid sequence DYKDDDDK (SEQ ID NO: 8), or a functional derivative or variant thereof. In some embodiments, a tag, e.g., FLAG tag is located after amino acid residue 452 of SEQ ID NO: 1 and before amino acid residue 453 of SEQ ID NO: 1. In some embodiments, the location of the tag, e.g., Flag Tag is between amino acid residue 452 and 453 of SEQ ID NO: 1. In some embodiments, the tag is located at the N-terminus of the C-terminal domain of MIS. In some embodiments, the tag is no longer than 50 amino acids, for example, no longer than about 50, or about 40, or about 30, or about 20, or about 10 amino acids in length or about 7 amino acids in length.

In some embodiments, a recombinant MIS protein described herein comprises the amino acid sequence of SEQ ID NO: 2 or SEQ ID NO: 3 or a functional fragment thereof, which can be encoded by nucleic acid sequences SEQ ID NO: 4 and 5 respectively.

Another aspect of the present invention relates to a pharmaceutical composition comprising a recombinant MIS protein as discussed herein and a pharmaceutically acceptable carrier.

Another aspect of the present invention relates to a polynucleotide encoding the recombinant MIS protein as discussed herein, e.g., where the polynucleotide corresponds to SEQ ID NO: 4 or SEQ ID NO: 5 or a nucleotide which has at least 95% sequence identity to the nucleic acid sequence of SEQ ID NO: 4 or SEQ ID NO: 5 respectively. Another aspect of the technology described herein relates to a vector comprising the polynucleotide of SEQ ID NO: 4 or SEQ ID NO: 5 or a nucleotide which has at least 95% sequence identity to the nucleic acid sequence of SEQ ID NO: 4 or SEQ ID NO: 5 respectively. In some embodiments, a vector is a viral vector or an expression vector, e.g., pcDNA 3.1, or alternative vectors for *E. coli* or bacteriophage. In some embodiments, a viral vector is selected from the group consisting of an adenoviral vector, a poxvirus vector and a lentiviral vector. In some embodiments, a viral vector is adeno-associated virus (AAV), for example, recombinant AAV serotype 9 (rAAV9).

In some embodiments, a vector comprises a nucleic acid sequence which encodes a recombinant MIS protein or fragment thereof which has at least 95% sequence identity to the nucleic acid sequence of SEQ ID NO: 4 or SEQ ID NO: 5, and where the nucleic acid sequence is operatively linked to tissue- or cell-type specific promoter. In some embodiments, a host cell comprising such a vector is also encompassed in the present invention.

In some embodiments, the vector comprising the polynucleotides as discussed herein can express the recombinant MIS protein at a constant level over a desired period of time.

Another aspect of the present invention relates to a human MIS protein produced by post-translational processing of the recombinant human MIS protein as discussed herein.

Another aspect of the technology discussed herein relates to a pharmaceutical composition comprising the vector as discussed herein and a pharmaceutically acceptable carrier.

Another aspect of the technology discussed herein relates a purified preparation, or substantially purified human MIS protein produced from the recombinant human MIS protein as discussed herein.

Another aspect of the technology as discussed herein relates to a method for treating a subject with cancer, comprising administering a composition comprising a recombinant MIS protein, wherein the recombinant MIS protein comprises a modification of at least one amino acid between residues 448-452 of SEQ ID NO: 1 to increase cleavage as compared to in the absence of a modification, with or without an internal tag protein. In some embodiments, the recombinant MIS protein has increased cleavage and increased yield of production in vitro as compared to wild-type MIS protein corresponding to amino acid residues of SEQ ID NO: 1.

In some embodiments, the recombinant human MIS protein (e.g., the polypeptide and/or the nucleic acid encoding a recombinant human MIS protein) as disclosed herein, or a functional fragment or derivative or variant thereof, can be used to treat a cancer. In some embodiments, the recombinant human MIS protein that can be used for cancer treatment comprises the amino acid residues 25-559 of SEQ ID NO: 2 or a functional fragment thereof. In some embodiments, the recombinant human MIS protein that can be used for cancer treatment comprises the amino acid residues 25-567 of SEQ ID NO: 3 or a functional fragment thereof. In some embodiments, the cancer is a MIS Responsive II (MISRII) cancer, or where the cancer expresses MISRII e.g., an ovarian cancer, or comprises an ovarian cancer cell, vulvar epidermal carcinoma cell, cervical carcinoma cell, endometrial edenocarinaoma cell and ovarian adenocarcinoma. In some embodiments, the cancer includes, but is not limited to any one of: breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, gum cancer, kidney cancer, liver cancer, nasopharynx cancer, ovarian cancer, prostate cancer, pancreatic cancer, skin cancer, stomach cancer, testis cancer, tongue cancer, melanoma, ocular melanoma, or uterine cancer.

In some embodiments of the methods disclosed herein, the administration of the recombinant MIS protein is prior to, during, or after administration of an additional agent or cancer therapy.

In some embodiments, the expression of Mullerian Inhibiting Substance (MIS) receptor is measured in a biological sample obtained from the subject, e.g., a cancer or tumor tissue sample or a cancer cell or tumor cell, e.g., a biopsy tissue sample.

In some embodiments, the cancer is a chemotherapeutic-resistant or multi-drug resistant cancer, e.g., where the cancer is a paclitaxel, cisplatin, rapamycin, pyrazoloanthrone, or Doxorubicin-resistant cancer.

In some embodiments, a recombinant MIS can be administered by any route, e.g., via intravenous, intradermal, intramuscular, intraarterial, intralesional, percutaneous, or subcutaneous, or by aerosol administration. In some embodiments, administration is therapeutic or prophylactic administration. In all aspects as discussed herein, a subject is a mammal, e.g., a human.

In some embodiments, at least one additional agent is administered to the subject in combination with (e.g., before, during or after) administration of the recombinant human MIS, such as a therapeutic agent or chemotherapeutic agent, for example, a chemotherapeutic agent is selected from the group consisting of: paclitaxel, cisplatin, doxorubicin, rapamycin, pyrazoloanthrone, including but not limited to antra(1,9-cd)pyrazol-6(2H)-one (SP600125) or N1-methyl-1,9-pyrazoloanthrone (M-SP600125) or a functional derivative or functional analogue thereof. In some embodiments, a chemotherapeutic agent is a radiotherapeutic agent.

Another aspect of the technology as disclosed herein relates to a method of decreasing the dose of a chemotherapeutic agent for the treatment of cancer, the method comprising administering to the subject a therapeutically effective amount of a recombinant MIS protein, wherein the recombinant MIS protein comprises a modification of amino acid 450 of SEQ ID NO: 1 from Q to R, wherein the therapeutically effective dose of the chemotherapeutic agent in the presence of the recombinant MIS protein is lower as compared to the therapeutically effective dose of the chemotherapeutic agent alone. In some embodiments, the recombinant MIS protein optionally comprises a Tag protein.

Other aspects of the technology as disclosed herein relates to the use of a recombinant MIS protein for the manufacture of a medicament for treating cancer, wherein the recombinant MIS protein comprises a modification of amino acid 450 of SEQ ID NO: 1 from Q to R, and wherein the cancer expresses a Mullerian Inhibiting Substance (MIS) receptor.

Another aspect of the present invention relates to an article of manufacture comprising packaging material and a pharmaceutical composition comprising the recombinant MIS protein as discussed herein, wherein the packaging material comprises a label which indicates the pharmaceutical composition may be administered, for a sufficient term at an effective dose, for treating or reducing the risk of cancer which expresses a Mullerian Inhibiting Substance (MIS) receptor.

Other aspects of the technology as disclosed herein relates to a method of treating a subject affected with cancer, the method comprising assessing the expression and/or activity of Mullerian Inhibiting Substance Receptor II (MISRII) in a biological sample obtained from the subject, wherein a clinician reviews the results and if the results indicate the presence of expression and/or activity of MISRII, the clinician directs the subject to be treated with pharmaceutical composition comprising a recombinant MIS protein as disclosed herein.

Other aspects of the technology as disclosed herein relates to the use of a recombinant MIS protein to decrease the plasma serum levels of one or more androgens in a subject in need thereof, wherein the recombinant MIS protein comprises a modification of amino acid 450 of SEQ ID NO: 1 from Q to R and optionally a tag, e.g., a Flag tag. In some embodiments, the recombinant human MIS protein that can be used for decreasing androgen levels comprises the amino acid residues 25-559 of SEQ ID NO: 2 or a functional fragment thereof.

In some embodiments, one or more androgens is testosterone. In some embodiments, a subject in need thereof has benign prostatic hypertrophy, or prostate cancer or polycystic ovarian disease and/or precocious puberty. In alternative embodiments, a subject in need thereof has a disease or disorder selected from the group including, but not limited to; Benign Prostatic Hyperplasia (BPH), prostate carcinoma, testicular cancer, androgen dependent acne, male pattern baldness, precocious puberty, hyperandrogenism, hirsutism, virilization, Polycystic Ovary Syndrome (POCS), hyperandrogenism (HA) and insulin resistance (IR) and acanthosis *nigricans* (AN) (HIAR-AN) syndrome, ovarian hyperthecosis, follicular maturation arrest, atresia, anovulation, dysmenorrheal, dysfunctional uterine bleeding, infertility and androgen-producing tumors.

Other aspects of the technology as disclosed herein relates to a method to treat a disease or disorder characterized by androgenic dependency, comprising administering to a subject an effective amount of the pharmaceutical composition comprising a recombinant MIS protein as discussed herein, or a pharmaceutical composition comprising a preparation of MIS protein from the cleavage of the recombinant MIS protein as disclosed herein, wherein the pharmaceutical composition reduces the level of at least one androgen in the plasma serum of the subject and results in a decrease in at least one symptom of a disease or disorder characterized by androgenic dependency.

Other aspects of the technology as disclosed herein relates to a method to decrease the plasma level of one or more androgens in a subject, the method comprising administering an effective amount of a recombinant MIS protein, wherein the recombinant MIS protein comprises a modification of amino acid 450 of SEQ ID NO: 1 from Q to R, where the recombinant MIS optionally comprises a tag, and wherein the recombinant MIS protein decreases the plasma serum levels of one or more androgens in the subject.

In some embodiments, a subject has a disease or disorder characterized by androgenic dependency, for example, but not limited to a disease or disorder is selected from the group of; Benign Prostatic Hyperplasia (BPH), prostate carcinoma, testicular cancer, androgen dependent acne, male pattern baldness, precocious puberty, hyperandrogenism, hirsutism, virilization, Polycystic Ovary Syndrome (POCS), hyperandrogenism (HA) and insulin resistance (IR) and acanthosis *nigricans* (AN) (HIAR-AN) syndrome, ovarian hyperthecosis, follicular maturation arrest, atresia, anovulation, dysmenorrheal, dysfunctional uterine bleeding, infertility and androgen-producing tumors.

Other aspects of the technology as disclosed herein relates to a kit comprising a recombinant MIS protein as discussed herein, or preparation of a MIS protein produced by the post-translational processing of a recombinant MIS protein discussed herein, and a pharmaceutically acceptable carrier. In some embodiments, a kit can optionally comprise instructions of use of the recombinant MIS protein for the treatment of cancer or treatment of an androgenic dependency disorder.

BRIEF DESCRIPTION OF THE DRAWINGS

FIG. 1A shows the leader sequence of MIS (25 amino acids) and albumin (24 amino acids) have 20% identity and 5 conserved amino acids. FIG. 1B is a schematic drawing showing the design of the RF (modified cleavage site plus Flag tag), LRF (leader sequence plus modified cleavage site plus Flag tag), and LR (leader sequence plus modified cleavage site) constructs including the placement of the flag tag (F), the modified cleavage site (R), and the albumin leader (L).

FIG. 3A shows purified recombinant RF-MIS, LRF-MIS and WT-MIS is compared using an antibody against the N-terminus which can recognize holo MIS monomer, the cleaved N-terminus, and cryptic cleavage products containing part of the N-terminus. FIG. 3B shows detection of purified recombinant RF-MIS, LRF-MIS and WT-MIS using an antibody against the C-terminus which can recognize holo MIS monomer, the cleaved C-terminus, and cryptic cleavage products containing part of the C-terminus.

FIG. 4A shows representative sections from both the treated ridge and the untreated contralateral control ridge are compared for Mullerian duct regression. FIG. 4B is a histogram showing the frequency distribution of those scores in FIG. 4A. (LRF-MIS N=6, RF-MIS N=39). W, Wolffian duct; M, Müllerian duct.

FIGS. 5A-5B show the amino acid of wild-type MIS protein (SEQ ID NO: 1) with the corresponding amino acid residues using conventional nomenclature of amino acid labeling (where the first numbered amino acid begins after the leader sequence). FIG. 5A shows the amino acid sequence of wild-type MIS protein of SEQ ID NO: 1, showing the leader sequence (in bold) and the primary and secondary cleavage sites highlighted. The corresponding amino acid numbering using conventional numbering is shown in brackets. FIG. 5B shows a Table indicating features on amino acid residues on SEQ ID NO: 1 which correspond with the amino acid residues using normal nomenclature of MIS (where the first numbered amino acid begins after the leader sequence). FIG. 5B discloses "RAQR/S" as SEQ ID NO: 26.

DETAILED DESCRIPTION OF THE INVENTION

Figures 1A, 1B:
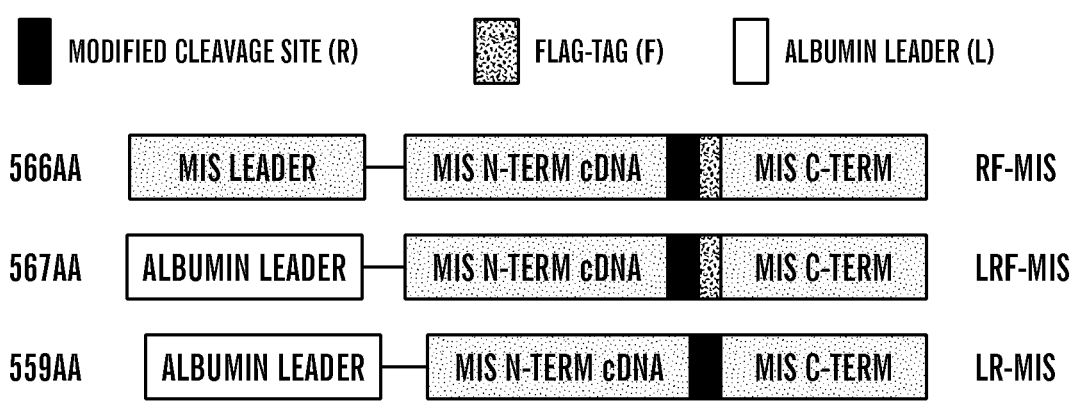
FIGS. 1A-1B are schematic drawings showing the design of new recombinant MIS constructs with the albumin leader sequence.

The present invention relates to modified recombinant human MIS protein which has at least one of the following characteristics; improved cleavage, increased bioactivity, increased potency and can be produced at high yield as compared to the wild-type human MIS protein, where the recombinant human MIS protein comprises a combination of the following: a modified Kex cleavage site for increased cleavage and a non-MIS leader sequence in place of the normal MIS leader sequence, to improve the yield of bioactive protein. In some embodiments, this modified MIS is with or without an internal label, or Tag, to facilitate its purification.

Accordingly, herein the inventors have engineered changes to the native human sequence to increase endogenous cleavage and thus the potency of MIS. The inventors have also, optionally, inserted a tag to facilitate its purification.

The inventors have also additionally modified recombinant human MIS protein to comprise a non-MIS leader sequence instead of the 25 amino acid MIS leader sequence of amino acids 1-25 of SEQ ID NO:1. In some embodiments, the leader sequence comprises an albumin leader sequence, such as a human serum albumin sequence (HSA) or a functional fragment or variant thereof. In some embodiments, the leader sequence comprises 24 amino acids of SEQ ID NO: 6 or a functional fragment thereof, and replaces amino acid residues 1-25 of SEQ ID NO: 1. This addition, surprisingly, has further increased cleavage of the recombinant MIS protein. This combination has led to higher yield of a product that is more homogeneous, with increased potency due to increased cleavage. This combination of changes yields a recombinant human MIS variant that can meet a previously unmet need to have a form of bioactive MIS that is labeled for use in receptor and other binding studies that will be very important both for the selection of patients for treatment and for addressing molecular mechanistic questions regarding the interaction of MIS in various receptor bearing tissues. In addition, the labeled ligand will be essential to determine if another receptor or other binding proteins exist in various tissues. Herein, the inventors demonstrate the production of an internally epitope tagged MIS that retains full bioactivity in the Mullerian duct regression assay. In one embodiment, the tag is a "FLAG" tag because of the availability of high quality reagents used for its detection and purification.

As discussed herein, the present invention provides a method for treating a variety of conditions by administering an effective amount of a recombinant human MIS protein and functional fragments and derivatives thereof as disclosed herein to a subject in need thereof. Conditions that may be treated by the compounds of this invention, or a pharmaceutical composition containing the same, include any condition which is treated or reduces the symptoms by administration of human MIS or activation of MIS signaling or activation of MISRII, and thereby benefit from administration of a recombinant human MIS protein and functional fragments and derivatives thereof. Representative conditions in this regard include, for example, but not limited to, cancers that express MIS receptors, for example cancer that express MISRII, for example, but not limited to ovarian, cervical and endometrial cancer. Other conditions which can be treated with MIS or activation of MIS signalling reduces the symptoms are proliferative diseases such as cancer, or abnormally high androgen stages such as polycysic ovarian disease, precocious puberty, and other hyperandrogen disorders, such as testotoxicosis, or any androgen-dependent tumor such as prostate cancer.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "Mullerian Inhibiting Substance" and "MIS" are used interchangeably herein and is also known as anti-Müllerian hormone or AMH, refer to compounds and materials which are structurally similar to MIS. By "MIS" or "Mullerian Inhibiting Substance" is meant a polypeptide having an amino acid sequence at least about 60%, or at least about 70%, or at least about 80%, or at least about 90%, or at least about 95%, or at least about 96%, or at least about 97%, or at least about 98%, or at least about 99% identical to amino acid residues 26-560 of SEQ ID NO: 1. The present invention is intended to include mutant forms of recombinant human MIS which have substantially the same, or greater biological activity as wild-type MIS. Examples of such mutant MIS molecules carrying a deletion, insertion, or alteration in the amino acid sequence of wild-type MIS (e.g., amino acid residues 26-560 of SEQ ID NO:1). Other forms of include substances are for example, salts, functional derivatives and aglycone forms of wild-type MIS and recombinant human MIS. Additionally, human recombinant MIS protein can be obtained using recombinant DNA technology, or from chemical synthesis of the MIS protein. For reference purposes only, the wild-type human MIS nucleic acid corresponds to RefSeq No: NM_000479, which are incorporated herein by reference.

The term "Mullerian Inhibiting Substance type II receptor" or "MISRII" are used interchangeably herein to refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 and GenBank No: AF172932 which are incorporated herein by reference The term "wild type" refers to the naturally-occurring polynucleotide sequence encoding a protein, or a portion thereof, or protein sequence, or portion thereof, respectively, as it normally exists in vivo. Accordingly, as disclosed herein, the wild type amino acid sequence for the pre-proprotein of human MIS corresponds to SEQ ID NO: 1, where amino acid residues 1-25 correspond to the leader sequence. The proprotein of MIS comprises amino acid residues 26-560 of SEQ ID NO: 1 (e.g., lacking the 1-25 leader sequence), which is then post-translationally processed by cleavage as discussed herein to form a bioactive MIS homodimer.

The term "soluble MIS polypeptide" as used herein refers to a MIS polypeptide that does not comprise at least part of, or all of, the amino acids which allow it to functionally bind to the membrane.

By a "polynucleotide encoding MIS" is meant a polynucleotide encoding a polypeptide having at least about 60%, or at least about 70%, or at least about 80%, or at least about 90%, or at least about 95%, or at least about 96%, or at least about 97%, or at least about 98%, or at least about 99% sequence identity to any of the amino acid sequences corresponding to amino acid residues 26-560 of SEQ ID NO: 1.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G." a thymine "T" or a cytosine "C") or RNA (e.g. an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. The term "nucleic acid" also refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid may encompass a double-stranded molecule or a double-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

As used herein, the term "gene product(s)" is used to refer to include RNA transcribed from a gene (e.g., mRNA), or a polypeptide encoded by a gene or translated from RNA.

The terms "polypeptide" and "protein" are used interchangeably to refer to a polymer of amino acid residues, and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., leader sequence cleavage of amino acids 1-25 of SEQ ID NO:1) and post-translational modifications of the polypeptide, such as, for example, disulfide-bond formation, glycosylation, acetylation, phosphorylation, proteolytic cleavage (e.g., cleavage by furins or metalloproteases and prohormone convertases (PCs)), and the like. Furthermore, for purposes of the present invention, a "polypeptide" encompasses a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a recombinant human MIS protein is comprised of D- or L-amino acid residues, as use of naturally occurring L-amino acid residues has the advantage that any break-down products should be relatively non-toxic to the cell or organism.

In yet a further embodiment, a recombinant human MIS protein or fragments or derivatives thereof can be a retro-inverso peptides. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The term "fragment" of a peptide, polypeptide or molecule as used herein refers to any contiguous polypeptide subset of the molecule. The term "protein fragment" as used herein includes both synthetic and naturally-occurring amino acid sequences derivable from the naturally occurring amino acid sequence of MIS (SEQ ID NO:1). The protein is said to be "derivable from the naturally-occurring amino acid sequence of a recombinant human MIS protein" if it can be obtained by fragmenting the recombinant human MIS protein, or if it can be synthesized based upon a knowledge of the sequence of the naturally occurring amino acid sequence or of the genetic material (DNA or RNA) which encodes this sequence. Accordingly, a "fragment" of a molecule, is meant to refer to any polypeptide subset of the molecule. In some embodiments, a functional fragment of recombinant human MIS comprises at least the C-terminal domain and at least the N-terminal domain. In some embodiments, a functional fragment comprises a portion of the C-terminal and/or a portion (e.g., fragment) of the N-terminal domain of the recombinant human MIS protein. Fragments of a recombinant human MIS protein which have the activity at least or greater than the wildtype MIS protein of SEQ ID NO: 1 as disclosed herein and which are soluble are also encompassed for use in the present invention.

Fragments of a recombinant human MIS protein, for example functional fragments of SEQ ID NO: 2 or 3 useful in the methods as disclosed herein have at least 30% the activity as that of a polypeptide of SEQ ID NO: 2 or 3 in vivo, e.g., to cause Mullerian duct regression in an Mullerian duct regression bioassay as disclosed herein in the Examples. Stated another way, a functional fragment of a recombinant human MIS protein is a fragment of any of SEQ ID NO: 2 or 3 which, alone or as a fusion protein can result in at least 30% of the same activity as compared to SEQ ID NO: 2 or 3 to bind and activate MISRII, or cause Mullerian duct regression in a Mullerian duct regression bioassay as disclosed herein (see FIG. 4). Fragments as used herein can be soluble (i.e. not membrane bound). A "fragment" can be at least about 6, at least about 9, at least about 15, at least about 20, at least about 30, least about 40, at least about 50, at least about 100, at least about 250, at least about 300 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NO:2 or 3 can be, for example, 1, 2, 3, 4, 5, 6, 7, 8, 9 or 10 amino acids or more than 10 amino acids, such as 15, 30, 50, 100 or more than 100 amino acids deleted from the N-terminal and/or C-terminal of SEQ ID NO: 2 or 3, respectively. Persons of ordinary skill in the art can easily identify the minimal peptide fragment of SEQ ID NO: 2 or 3 useful in the methods and compositions as disclosed herein, or fusion proteins as disclosed herein, by sequentially deleting N- and/or C-terminal amino acids from SEQ ID NO: 2 or 3, or sequentially deleting N- and C-terminal amino acids from recombinant human MIS protein and assessing the function of the resulting peptide fragment, alone or when it is cleaved. One can create functional fragments with multiple smaller fragments. These can be attached by bridging peptide linkers. One can readily select linkers to maintain wild type conformation. One of ordinary skill in the art can easily assess the function of recombinant human MIS protein as disclosed herein to activate MISRII or in the Mullerian duct regression bioassay, as disclosed herein as compared to a recombinant human MIS protein corresponding to SEQ ID NO: 2 or 3. Using such an in vivo assay, if the fragment of the recombinant human MIS protein has at least 30% of the biological activity of the recombinant human MIS protein corresponding to SEQ ID NO:2 or 3 as disclosed herein, then the fragment is considered a valid recombinant human MIS protein-fragment and can used in the compositions and methods as disclosed herein. In some embodiments, a fragment of SEQ ID NO: 2 or 3 can be less than 200, or less than 150 or less than 100, or less than 50, or less than 20 amino acids of SEQ ID NO: 2 or 3. In some embodiments, a fragment of SEQ ID NO: 2 or 3 is less than 100 peptides in length. However, as stated above, the fragment must be at least 6 amino acids, at least about 9, at least about 15, at least about 20, at least about 30, at least about 40, at least about 50, at least about 100, at least about 250, at least about 500 nucleic acids or amino acids, or any integers in between.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" or "fragment" refers to a polypeptide which possess a biological activity (either functional or structural) that is substantially similar to a biological activity of the polypeptide which it is a functional derivative, variant or functional fragment thereof. The term functional derivative is intended to include the fragments, analogues or chemical derivatives of a molecule. By "substantially similar" in this context is meant that the biological activity, e.g., activation of MISRII is at 25% or at least 35%, or at least 50% as active as a reference polypeptide, e.g., a corresponding wild-type MIS polypeptide or recombinant human MIS protein, and preferably at least 60% as active, 70% as active, 80% as active, 90% as active, 95% as active, 100% as active or even higher (i.e., the variant or derivative has greater activity than the wild-type), e.g., 110% as active, 120% as active, or more. Stated another way, a "substantially similar" functional fragment of a recombinant human MIS protein in this context is meant that at least 25%, at least 35%, at least 50% of the relevant or desired biological activity of a corresponding recombinant human MIS protein is retained. In the instance of a functional fragment or peptide of a recombinant human MIS protein as disclosed herein (e.g., SEQ ID NO: 2 or 3), a functional fragment of SEQ ID NO: 2 or 3 would be a protein or peptide comprising a portion of SEQ ID NO: 2 or 3 which retained an activity to activate MISRII, or in the Mullerian duct regression bioassay, as disclosed herein in the Examples; preferably the fragment of SEQ ID NO: 2 or 3 that retains at least 25%, at least 35%, at least 50% at least 60%, at least 70%, at least 80%, at least 90%, at least 95%, at least 100% or even higher (i.e., the variant or derivative has greater activity than the wild-type MIS of SEQ ID NO: 1 or of a recombinant human MIS protein of SEQ ID NO 2 or 3), e.g., at least 110%, at least 120%, or more activity compared to the full length SEQ ID NO: 2 or 3 to activate MISRII or cause Mullerian duct regression in the Mullerian duct regression bioassay as disclosed herein. As another example, in the instance of a fragment of MIS (e.g., amino acids 26-560 of SEQ ID NO: 1) would be a protein or peptide comprising a portion of amino acids 26-560 of SEQ ID NO: 1 which retained an activity for Mullerian duct regression, preferably the fragment of amino acids 26-560 of SEQ ID NO: 1 retains at least 25%, at least 35%, at least 50% at least 60%, at least 70%, at least 80%, at least 90%, at least 95%, at least 100% or even higher (i.e., the variant or derivative has greater activity than the wild-type), e.g., at least 110%, at least 120%, or more activity compared to the full length amino acids 26-560 of SEQ ID NO: 1 to cause Mullerian duct regression in an mullerian duct regression bioassay as disclosed herein in the Examples. As an alternative example, a fragment of a HSA leader sequence of SEQ ID NO: 6 would be a protein or peptide comprising a portion of SEQ ID NO: 6 which retained at least 25%, at least 35%, at least 50% at least 60%, at least 70%, at least 80%, at least 90%, at least 95%, at least 100% or even higher (i.e., the variant or derivative has greater activity than the wild-type HSA sequence), e.g., at least 110%, at least 120%, or more activity compared to the full length HSA sequence of SEQ ID NO: 6, as determined by an assay, for example as disclosed in U.S. Pat. No. 5,759,802 which is incorporated herein in its entirety by reference.

The term "functional derivative" and "mimetic" or "biologically active variant" or "biologically active fragment" are used interchangeably, and refers to a compound which possess a biological activity (either functional or structural) that is substantially similar to a biological activity of the entity or molecule its is a functional derivative of (e.g., the recombinant human MIS protein). The term functional derivative is intended to include the fragments, variants, analogues or chemical derivatives of a molecule.

The term "functional derivatives" is intended to include the "fragments," "variants," "analogs," or "chemical derivatives" of a molecule. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a recombinant human MIS protein is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

A "variant" of a recombinant human MIS protein is meant to refer to a molecule substantially similar in structure and function to either the entire molecule, or to a fragment thereof. Accordingly, the term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a recombinant human MIS protein is meant to refer to a molecule substantially similar in structure and function, i.e. where the function is the ability to activate MISRII.

For example, a variant of a recombinant human MIS protein can contain a mutation or modification that differs from a reference amino acid in SEQ ID NO: 2 or 3. In some embodiments, a variant of SEQ ID NO: 2 or 3 is a fragment of SEQ ID NO: 2 or 3 as disclosed herein. In some embodiments, a variant can be a different isoform of SEQ ID NO: 2 or 3 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to reduce T-reg cells and/or decrease inflammatory cytokines as disclosed herein). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the MIS protein (i.e. the ability of a recombinant human MIS protein or variant to cause Mullerian duct regression in vivo, which can be determined using the Mullerian Duct regression bioassay as disclosed herein). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983) 171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a recombinant human MIS protein, for example a variant of SEQ ID NO: 2 or 3 is meant to refer to any molecule substantially similar in structure and function to either the entire molecule of SEQ ID NO:2 or 3, or to a fragment thereof.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical.

Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

A molecule is said to be "substantially similar" to another molecule if both molecules have substantially similar structures or if both molecules possess a similar biological activity, for example if both molecules are able to activate MISRII. Thus, provided that two molecules possess a similar activity, (i.e. a variant of a recombinant human MIS protein which can activate MISRII similar to that of the MIS protein which corresponds to SEQ ID NO: 1, or recombinant human MIS protein which corresponds to SEQ ID NO: 2 or 3) are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical. In particular, the term "substantially similar", when used to define a recombinant human MIS protein comprising a functional variant of recombinant human MIS protein as compared to the recombinant human MIS protein encoded by SEQ ID NO:2 or 3, means that a particular subject sequence, for example, a recombinant human MIS protein variant or derivative sequence, varies from the sequence of the natural (or wild-type) MIS of SEQ ID NO: 1 or recombinant human MIS protein (i.e. encoded by SEQ ID NO: 2 or 3), by one or more substitutions, deletions, or additions, although the net effect of which is to retain at least some of the biological activity found in the recombinant human MIS protein as disclosed herein. As such, nucleic acid and amino acid sequences having lesser degrees of similarity but comparable biological activity to recombinant human MIS protein are considered to be equivalents. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a specific nucleic acid sequence of SEQ ID NO:4 or 5 as disclosed herein if: (a) the nucleotide sequence is hybridizes to the coding regions of the natural MIS nucleic acid, or (b) the nucleotide sequence is capable of hybridization to nucleotide sequence of a recombinant human MIS protein encoded by SEQ ID NO: 4 or 5 under moderately stringent conditions and has biological activity similar to the recombinant human MIS protein; or (c) the nucleotide sequences which are degenerative as a result of the genetic code to the nucleotide sequences defined in (a) or (b). Substantially similar proteins will typically be greater than about 80% similar to the corresponding sequence of the native protein.

The term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

In one embodiment, the term "human homolog" to a gene transcript refers to a DNA sequence that has at least about 55% homology to the full length nucleotide sequence of the sequence of a recombinant human MIS protein gene as encoded by the genome of humans or an animal, for example mouse or transgenic animal. In one embodiment, the term "human homolog" to a protein identified as associated with a recombinant human MIS protein refers to an amino acid sequence that has 40% homology to the full length amino acid sequence of the protein identified as associated with a recombinant human MIS protein as encoded by the genome of the transgenic animal of the present invention, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.). Determination of the human homologs of the genes of the present invention may be easily ascertained by the skilled artisan.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions."

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a recombinant human MIS protein, for example SEQ ID NO: 2 or 3 refers to a molecule similar in function to either the entire molecule or to a fragment thereof. The term "analog" is also intended to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, γ-carboxyglutamate, ε-N,N,N-trimethyllysine, ε-N-acetyllysine, σ-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the recombinant human MIS-fusion protein is derived from the nucleotide sequence of encoding a recombinant human MIS protein or a functional derivative fragment or variant thereof, fused in frame to an end, either the 5' or the 3' end, of a gene encoding a first fusion partner, such as a IgG1 Fc fragment. In this manner, on expression of the gene, the recombinant human MIS protein or functional derivative fragment or variant thereof is functionally expressed and fused to the N-terminal or C-terminal end of the IgG1 Fc. In certain embodiments, modification of the polypeptide probe is such that the functionality of the recombinant human MIS protein or a functional derivative fragment or variant thereof remains substantially unaffected in terms of its biological activity by fusion to the first fusion partner, such as IgG1 Fc.

By "specifically binds" or "specific binding" is meant a compound or antibody that recognizes and binds a desired polypeptide but that does not substantially recognize and bind other molecules in a sample, for example, a biological sample, which naturally includes a polypeptide of the invention.

By "substantially pure" or is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By "enhanced proteolytic stability" is meant a reduction of in the rate or extent of proteolysis of a peptide sequence by at least about 2%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, or at least about 99% as compared to a control sequence under the same conditions (e.g., in vivo or in an in vitro system such as in a cell or cell lysate). A peptide with enhanced proteolytic stability may contain any modification, for example, insertions, deletions, or point mutations which reduce or eliminate a site subject to proteolytic cleavage at a particular site. Sites of proteolytic cleavage may be identified based on known target sequences or using computer software (e.g., software described by Gasteiger et al., *Protein Identification and Analysis Tools on the ExPASy Server*. In John M. Walker, ed. *The Proteomics Protocols Handbook*, Humana Press (2005)). Alternatively, proteolytic sites can be determined experimentally, for example, by Western blot for the protein following expression or incubation in a cellular system or cellular lysate, followed by sequencing of the identified fragments to determine cleavage sites.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The terms "subject" and "individual" are used interchangeably herein, and refer to an animal, for example a human, to whom treatment, including prophylactic treatment, with the pharmaceutical composition according to the present invention, is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. The term subject also encompasses a mammal, for example, a human, to whom treatment, such as therapeutic treatment and/or prophylactic treatment with a composition comprising a recombinant human MIS protein as disclosed herein is provided.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "therapy resistant cancer" as used herein refers to a cancer present in a subject which is resistant to, or refractory to at least two different anti-cancer agents such as chemotherapy agents, which means, typically a subject has been treated with at least two different anti-cancer agents that did not provide effective treatment as that term is defined herein.

The term 'sensitize' or 'sensitizes' used interchangeably herein, refers to making the cell sensitive, or susceptible to other secondary agents, for example other pro-drugs or other environmental effects such as radiation etc.

As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a measurable lessening of one or more symptoms or measurable markers of a disease or disorder (e.g., cancer) and/or a cessation of at least slowing of progress or worsening of symptoms that would be expected in absence of treatment. Measurable lessening includes any statistically significant decline in a measurable marker or symptom. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis. In some embodiments, treatment can be prophylactic treatment.

The term "effective amount" as used herein refers to the amount of a recombinant human MIS protein as disclosed herein, to alleviate at least one or more symptom of the disease or disorder, and relates to a sufficient amount of pharmacological composition to provide the desired effect. The phrase "therapeutically effective amount" as used herein, e.g., a pharmaceutical composition comprising at least one recombinant human MIS protein as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylacticly significant reduction in a symptom or clinical marker associated with a cancer or a cancer-mediated condition.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer with a pharmaceutical composition comprising at least one recombinant human MIS protein as disclosed herein, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a cancer treatment is used to refer to the reduction of a symptom and/or a biochemical marker of cancer, for example a significant reduction in at least one biochemical marker of cancer would be considered an effective treatment. Examples of such biochemical markers of cancer include CD44, telomerase, TGF-α, TGF-β, erbB-2, erbB-3, MUC1, MUC2, CK20, PSA, CA125 and FOBT. A reduction in the rate of proliferation of the cancer cells by at least about 10% would also be considered effective treatment by the methods as disclosed herein. As alternative examples, a reduction in a symptom of cancer, for example, a slowing of the rate of growth of the cancer by at least about 10% or a cessation of the increase in tumor size, or a reduction in the size of a tumor by at least about 10% or a reduction in the tumor spread (i.e. tumor metastasis) by at least about 10% would also be considered as affective treatments by the methods as disclosed herein. In some embodiments, it is preferred, but not required that the therapeutic agent actually kill the tumor.

The term "prophylactically effective amount" refers to an amount of a recombinant human MIS protein or functional fragment or variant thereof which is effective, at dosages and for periods of time necessary, to achieve the desired prophylactic result, e.g., to prevent the onset of cancer in a subject who is at risk of developing cancer. Typically, since a prophylactic dose of a recombinant human MIS protein or functional fragment or variant thereof is administered to a subject prior to, or at an earlier stage of a cancer, or to a subject who has a genetic predisposition to get cancer, for example, but by no way a limitation, to a subject that has a mutation in a gene which increases the likelihood of the subject getting ovarian cancer. In some embodiments, a prophylactically effective amount is less than the therapeutically effective amount. A prophylatically effective amount of a recombinant human MIS protein or functional fragment or variant thereof is also one in which any toxic or detrimental effects of the compound are outweighed by the beneficial effects.

As used herein, the terms "prevent," "preventing" and "prevention" refer to the avoidance or delay in manifestation of one or more symptoms or measurable markers of a disease or disorder, e.g., of an autoimmune disease. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the terms "administering," and "introducing" are used interchangeably herein and refer to the placement of the agents of metabolic regulators of the present invention into a subject by a method or route which results in at least partial localization of a recombinant human MIS protein at a desired site. The compounds of the present invention can be administered by any appropriate route which results in an effective treatment in the subject. In some embodiments, for the treatment of a cancer, the recombinant human MIS protein can be placed directly at, or near the site of the tumor or alternatively administered systemically.

A "composition" or "pharmaceutical composition" are used interchangeably herein refers to a composition that usually contains an excipient, such as a pharmaceutically acceptable carrier that is conventional in the art and that is suitable for administration to cells. The cells may be part of a subject, for example for therapeutic, diagnostic, or prophylactic purposes. The cells may also be cultured, for example cells as part of an assay for screening potential pharmaceutical compositions, and the cells may be part of a transgenic animal for research purposes. The composition can also be a cell culture, in which a polypeptide or polynucleotide encoding a metabolic regulator of the present invention is present in the cells and/or in the culture medium. In addition, compositions for topical (e.g., oral mucosa, respiratory mucosa) and/or oral administration can form solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: *The Science and Practice of Pharmacy with Facts and Comparisons,* 21st Ed.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of a recombinant human MIS protein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "oncogene" as used herein refers to a nucleic acid sequence encoding, or polypeptide, of a mutated and/or overexpressed version of a normal gene that in a dominant fashion can release the cell from normal restraints on growth and thus alone or in concert with other changes, contribute to a cells tumorigenicity. Examples of oncogenes include; gp40 (v-fms); p21 (ras); p55 (v-myc); p65 (gag-jun); pp60 (v-src); v-abl; v-erb; v-erba; v-fos etc. A proto-oncogene refers to the normal expression of a nucleic acid expressing the normal, cellular equivalent of an oncogene, typically these genes are usually a gene involved in the signaling or regulation of cell growth.

The term "regeneration" means regrowth of a cell population, organ or tissue, and in some embodiments after disease or trauma.

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors". Expression vectors can result in stable or transient expression of the DNA. An exemplary expression vector for use in the present invention is pcDNA3.1.

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g. EPV and EBV vectors.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter.

As used herein, the term "biological sample" also refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from a subject, but the term can also refer to non-cellular biological material, such as non-cellular fractions of blood, saliva, or urine, that can be used to measure protein phosphorylation levels. In some embodiments, a "biological sample" or "tissue sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, a biological sample is from a resection, bronchoscopic biopsy, or core needle biopsy of a primary, secondary or metastatic tumor, or a cellblock from pleural fluid. In addition, fine needle aspirate biological samples are also useful. In some embodiments, a biological sample is primary ascite cells. Samples can be fresh, frozen, fixed or optionally paraffin-embedded, frozen or subjected to other tissue preservation methods, including for example methods to preserve the phosphorylation status of polypeptides in the biological sample. A biological sample can also mean a sample of biological tissue or fluid that comprises protein or cells. Such samples include, but are not limited to, tissue isolated from subjects or animals. Biological samples may also include sections of tissues such as biopsy and autopsy samples, frozen sections taken for histological purposes, blood, plasma, serum, sputum, stool, tears, mucus, hair, and skin. Biological samples also include explants and primary and/or transformed cell cultures derived from patient tissues. A biological sample may be provided by removing a sample of cells from subject, but can also be accomplished by using previously isolated cells (e.g., isolated by another person, at another time, and/or for another purpose), or by performing the methods of the invention in vivo. Archival tissues, such as those having treatment or outcome history may also be used. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. The biological sample can be obtained by removing a sample of cells from a subject, but can also be accomplished by using previously isolated cells (e.g. isolated by another person), or by performing the methods of the invention in vivo. Such samples include, but are not limited to, whole blood, cultured cells, primary cell preparations, sputum, amniotic fluid, tissue or fine needle biopsy samples, peritoneal fluid, and pleural fluid, among others. In some embodiments a biological sample is taken from a human patient, and in alternative embodiments the biological sample is taken from any mammal, such as rodents, animal models of diseases, commercial animals, companion animals, dogs, cats, sheep, cattle, and pigs, etc. The biological sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The biological sample can in certain circumstances be stored for use prior to use in the assay as disclosed herein. Such storage can be at +4 C or frozen, for example at −20 C or −80 C, provided suitable cryopreservation agents are used to maintain cell viability once the cells are thawed.

The term "reduced" or "reduce" or "decrease" or "lower" as used herein generally means a decrease by a statistically significant amount relative to a reference. However, for avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e. absent level as compared to a reference sample), or any decrease between 10-100% as compared to a reference level, as that term is defined herein. The term "decrease" or "inhibition" used in the context of the level of expression or activity of a gene refers to a reduction in protein or nucleic acid level or activity in a cell, a cell extract, or a cell supernatant. For example, such a decrease may be due to reduced RNA stability, transcription, or translation, increased protein degradation, or RNA interference. Preferably, this decrease is at least about 5%, at least about 10%, at least about 25%, at least about 50%, at least about 75%, at least about 80%, or even at least about 90% of the level of expression or activity under control conditions.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e. absent level as compared to a reference sample).

The terms "increased" or "increase" as used herein generally mean an increase by a statically significant amount; for the avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein. The term an "increase" as used in the context of the expression or activity of a gene or protein is meant a positive change in protein or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The term "high" as used herein generally means a higher by a statically significant amount relative to a reference; for the avoidance of doubt, "high" means a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, at least 2-fold higher, at least 3-fold higher, at least 4-fold higher, at least 5-fold higher, at least 10-fold higher or more, as compared to a reference level.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Mullerian Inhibiting Substance (MIS)

Without wishing to be bound by theory, the Mullerian Inhibiting Substance (MIS) is a member of the TGFβ multigene family of glycoproteins. The proteins in this gene family are all produced as dimeric precursors and undergo posttranslational processing for activation, requiring cleavage and dissociation to release bioactive C-terminal fragments. MIS is a 140-kDa dimer which consists of identical 70 kDa disulfide-linked monomers, each composed of a 57 kDa N-terminal domain and a 12.5 kDa carboxyl-terminal (C-terminal). Thus, MIS comprises 2 identical monomers (and thus is termed a "homodimer"), each monomer comprising two domains, the N-terminal and C-terminal domain, which are held in non-covalent association. The purified C-terminal domain is the biologically active moiety and cleavage is required for activity. The N-terminal domain may assist with protein folding in vivo and facilitate delivery of the C-terminal peptide to its receptor, e.g., MISRI and MISRII. A non-cleavable mutant of MIS is biologically inactive.

The carboxy-terminal active domain shares amino acid homology with other TGFb family members, such as TGF-B 1, 2, and 3, inhibin, activin, and bone morphogenetic proteins, as well as a member of Growth and Differentiation Factors (GDFs). The structure of the MIS carboxy-terminal domain is supported by seven cysteines involved both in intra- and intermolecular disulfides bridges that lead to its structural stability, as revealed by homology to the three dimensional structure of TGFb using molecular modeling (Lorenzo, Donahoe, et al., unpublished data).

Like other TGFb family members, MIS can be cleaved by plasmin which generates its amino- and carboxy-terminal domains. This proteolytic process is required for its physiological activity and occurs at a site in a position similar to the dibasic cleavage site found in the sequence of TGFb. The resultant products are tightly associated in a non-covalent complex that dissociates at low pH; therefore, technically complex and time-demanding protocols with plasmin treatment and molecular size exclusion chromatography are required to enhance or complete the separation of the carboxy terminus from the amino terminus.

MIS contains two major cleavage sites that are sensitive to plasmin; the primary monobasic site which is located at amino acid position 426-427 of human wild-type MIS (corresponding to amino acid 451-452 of SEQ ID NO:1 herein). Cleavage at this site, which releases the active carboxy-terminal domain of MIS, resembles a consensus furin cleavage site. A secondary cleavage site (referred to as "R/S"), identified by amino-terminal sequencing of MIS fragments is located at residues 229-230 in the amino-terminal domain of wild-type MIS (corresponding to amino acids 254-255 of SEQ ID NO: 1). This site contains an R/S, but otherwise does not follow the consensus Arg-X-(Arg/Lys)-Arg for furin cleavage. Separation of purified carboxy-terminal from amino-terminal MIS after digestion with exogenous plasmin previously used molecular size-exclusion chromatography under acidic conditions. This technique requires extreme care to control MIS digestion, since long incubations of MIS in plasmin produced the carboxy-terminal MIS domain plus other fragments of 22 and 34 kDa, due to cleavage both at the primary and secondary sites, are extremely difficult to separate from one another by size exclusion. Since all fragments generated after plasmin digestion are glycosylated, except the carboxy-terminal domain, wheat-germ lectin affinity can be used as an alternative to size chromatography separation to purify the carboxy-terminal domain of MIS. After plasmin cleavage, the resulting fragments can be loaded onto a wheat germ lectin column at pH 3.5 in order to dissociate the amino- and carboxy-terminal domains, as disclosed in Lorenzo et al., J. Chromatography, (2001), 776; 89-98, which is incorporated herein its entirety by reference.

Accordingly, to overcome several issues with respect to avoiding the production of fragments of MIS, e.g., both the carboxy-terminal MIS domain plus a 22 and 34 kDa fragments due to cleavage both at the primary and secondary sites, the inventors have modified the primary cleavage site at amino acid position 426-427 of human wild-type MIS (corresponding to amino acid 451-452 of SEQ ID NO:1 herein). To aid the purification of the C-terminal domain without the need for complicated methods using wheat-germ lectin affinity or size chromatography columns, the most flexible domain of the C-terminus, the inventors have included a tag at the N-terminus of the C-terminal domain.

Furthermore, the wild-type MIS protein is produced as a prohormone comprising a N-terminal leader sequence, which corresponds to amino acid residues 1-25 of SEQ ID NO: 1. Processing of the mature hormone MIS protein can involve the proteolytic cleavage and removal of the leader sequence (e.g., amino acids 1-25 of SEQ ID NO: 1), the cleavage of the MIS protein at the primary site to generate the N-terminal and C-terminal domains, and the formation of these domains into a monomer, which is disulfide linked by inter- and intrachain disulfide bonds to an identical monomer to form the bioactive homodimer MIS protein.

Leader Sequences

Without wishing to be bound by theory, leader sequences improve expression and/or secretion of a polypeptide of interest in a host cell, and are useful for the recombinant production of proteins. Generally, as an efficient method for secreting a desired protein by a genetic engineering procedure, a method is known wherein a fused protein comprising the desired protein (e.g., MIS) and a prepropeptide (signal peptide+propeptide) is expressed in a host cell and then intracellularly cleaved (processed) by enzymes of the host, and then, extracellularly secreted. According to this process, however, the fused protein must be cleaved twice by enzymes of the host to be a mature protein, resulting in lower yield of the mature protein and contamination of the mature protein with residual fused protein.

Accordingly, secreted proteins are expressed initially inside the cell in a precursor form containing a leader sequence ensuring entry into the secretory pathway. Such leader sequences, also referred to as signal peptides, direct the expressed product across the membrane of the endoplasmic reticulum (ER). Signal peptides are generally cleaved off by signal peptidases during translocation to the ER. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer and Rothman (1987) Ann. Rev. Biochem. 56:829-852).

For Industrial production of a secreted protein, the protein to be produced needs to be secreted efficiently from the host cell or the host organism. The signal peptide may be, e.g., the native signal peptide of the protein to be produced, a heterologous signal peptide, or a hybrid of native and heterologous signal peptide. However, several problems are encountered with the use of currently known signal peptides. One problem often encountered when producing a human protein from a non-human host cell or organism is that the native signal peptide does not ensure efficient translocation and/or cleavage of the signal peptide. This leads to low rates of protein secretion and/or to secretion of mature proteins that display N-terminal extensions due to an incorrect cleavage of the signal peptide. Thus the choice of the signal peptide is of great importance for industrial production of a protein.

In addition of leader sequences directing the secretion of the protein, a precursor form can comprise supplemental leader sequences that are cleaved during maturation. These supplemental leader peptides, named propeptides, usually follow the signal peptide. Virtually all peptide hormones, numerous bioactive protein (for example, growth factors, receptors and cell-adhesion molecules, and including MIS), and many bacterial toxins and viral envelope glycoproteins comprise a propeptide that is post-translationally excised to generate the mature and biologically active protein (Seidah and Chretien (1999) Brain Res. 848:45-62).

Peptides are further cleaved by enzymes named proprotein convertases. Mammalian proprotein convertases include, e.g., the subtilisin convertases PCSK1, PCSK2 and furin. Furin is ubiquitously expressed and located in the trans-Golgi network. Furin proteolytically activates large numbers of proproteins substrates in secretory pathway compartments. (Thomas (2002) Nat Rev Mol Cell Biol. 3:753-766). More specifically, furin localizes to the Trans Golgi Network, a late Golgi structure that is responsible for sorting secretory pathway proteins to their final destinations, including the cell surface, endosomes, lysosomes and secretory granules. The site that furin cleaves has been extensively studied. The cleavage site is positioned after the carboxyl-terminal arginine of the consensus sequence R-X-L/R-R, wherein X may represent any amino acid (Nakayama (1997) Biochem. J 327:625-635). The cleavage efficiency is increased when X is a lysine, a valine, an isoleucine or an alanine (Watanabe et al (1992) J Biol. Chem. 267:8270-8274).

In some embodiments, the recombinant human MIS protein comprises a modified leader sequence in place of the wild-type leader sequence of the MIS protein of SEQ ID NO:1. In some embodiments, the native leader sequence of amino acid residues 1-25 of SEQ ID NO: 1 is replaced with a non-MIS leader sequence, for example, but not limited to an albumin leader sequence, or functional fragment thereof. In some embodiments, the non-MIS leader sequence is a human serum albumin sequence (HSA), for example, a leader sequence corresponding to SEQ ID NO:6, which is encoded by nucleic acids corresponding to SEQ ID NO: 7.

In some embodiments, a HSA sequence is a functional fragment of SEQ ID NO: 6, for example, or at least 23, or at least 22, or at least 21, or at least 20, or at least 19, or at least 18, or at least 17, or at least 16, or at least 15, or at least 14, or at least 13, or at least 12, or at least 11, or at least 10, or less than 10 consecutive or non-consecutive amino acids of SEQ ID NO:6. Modified versions of HSA leader sequence are also encompassed for use in the present invention and are disclosed in U.S. Pat. No. 5,759,802 which is incorporated herein in its entirety by reference. In some embodiments, a functional fragment of HSA leader sequence is MKWVTFISLLFLFSSAYS (SEQ ID NO: 13) or variations therefor, which are disclosed in EP patent EP2277889 which is incorporated herein in its entirety. Variants of the pre-pro region of the HSA signal sequence (e.g., MKWVTFISLL-FLFSSAYSRGVFRR, SEQ ID NO: 6) include fragments, such as the pre region of the HSA signal sequence (e.g., MKWVTFISLLFLFSSAYS, SEQ ID NO:13) or variants thereof, such as, for example, MKWVSFISLLFLFSSAYS, (SEQ ID NO:14)

In some embodiments, the leader sequence is a leader sequence is at least about 60%, or at least about 70%, or at least about 80%, or at least about 90%, or at least about 95%, or at least about 96%, or at least about 97%, or at least about 98%, or at least about 99% identical to amino acid residues of SEQ ID NO: 6.

Figure 2:
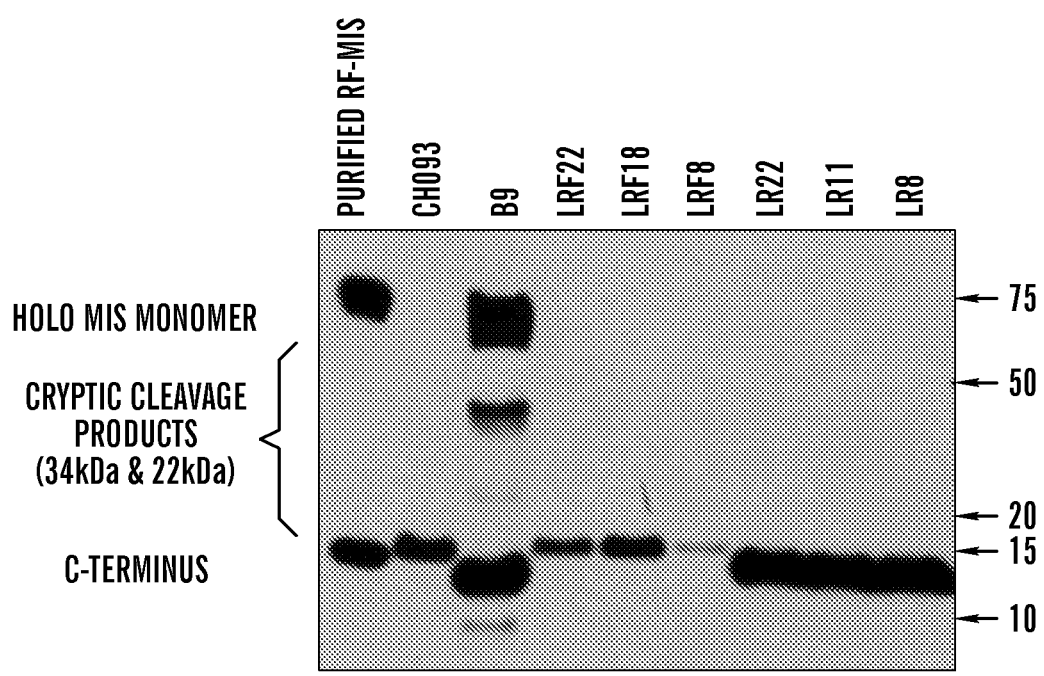
FIG. 2 shows MIS production and cleavage in CHOK1 clones stably transfected with recombinant human LR-MIS and LRF-MIS constructs. Western blot of 4% reduced SDS gels of media supernatant after 72 h in culture using an anti-MIS goat polyclonal antibody targeting the c-terminus of MIS (1:200). Purified RF-MIS, CHO93 media and B9 media shown as positive controls.
Figure 3A:
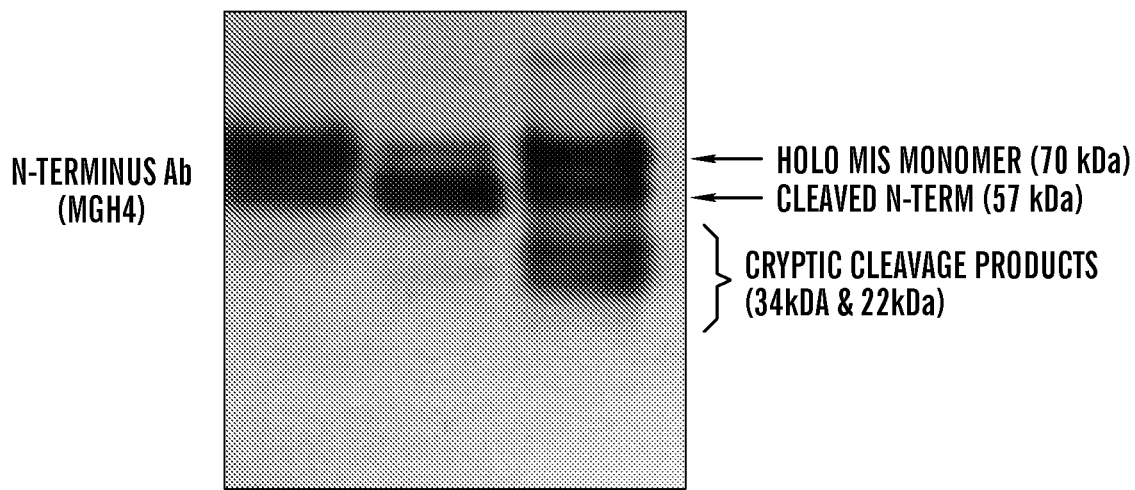
FIGS. 3A-3B show purified recombinant MIS analyzed by western blot of reduced SDS gels to estimate the amount of cleavage.
Figure 3B:
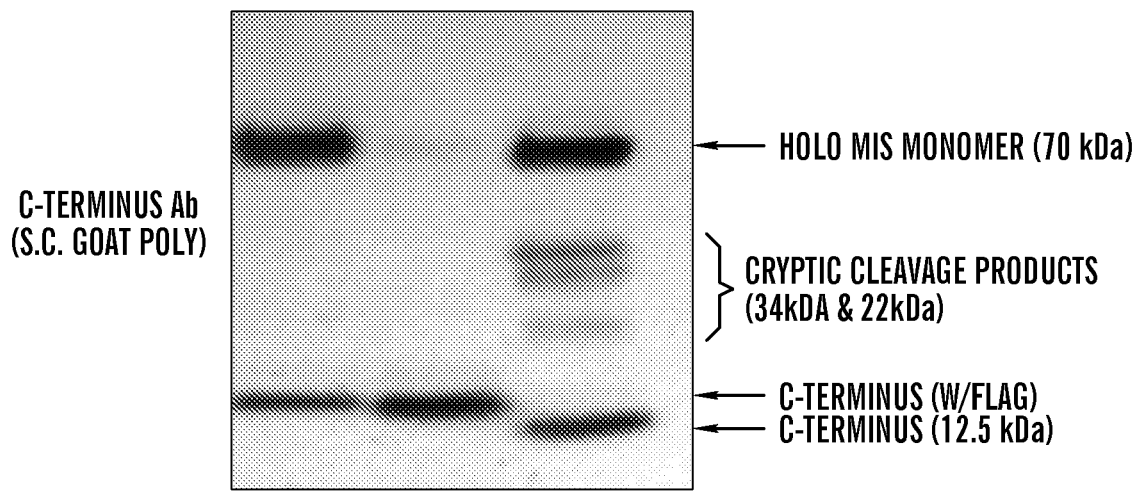

The HSA leader sequence as used herein resulted in an expected increased yield (both higher concentration and higher production) of the recombinant human MIS protein (see FIGS. 2 and 3). However, the presence of the HSA leader sequence also resulted in a surprising and unexpected increase in cleavage from the primary cleavage site (corresponding to cleavage at 451/452 of SEQ ID NO: 1 (or 426/427 of conventional amino acid nomenclature of wild-type human MIS protein) (see FIGS. 2 and 3). This increased yield and increased cleavage was surprising because with an increased yield (and therefore more protein produced by the cell), one would expect a decreased cleavage as the activity of the available cleavage enzymes becomes saturated and overextended. However, this was not the case—in fact the exact opposite occurred where with increased protein production there was increased cleavage from the primary cleavage site.

Other leader sequences are encompassed for use in a recombinant human MIS protein as disclosed herein, e.g., to replace amino acids 1-25 of SEQ ID NO: 1. Such leader sequences are well known in the art, and include the leader sequences comprising an immunoglobulin signal peptide fused to a tissue-type plasminogen activator propeptide (IgSP-tPA), as disclosed in US 2007/0141666, which is incorporated herein in its entirety by reference. Numerous other signal peptides are used for production of secreted proteins. One of them is a murine immunoglobulin signal peptide (IgSP, EMBL Accession No. M13331). IgSP was first identified in 1983 by Loh et al. (Cell. 33:85-93). IgSP is known to give a good expression in mammalian cells. For example. EP patent No. 0382762 discloses a method of producing horseradish peroxidase by constructing a fusion polypeptide between IgSP and horseradish peroxidase.

Other leader sequences include, for example, but not limited to, the MPIF-1 signal sequence (e.g., amino acids 1-21 of GenBank Accession number AAB51134) MKVSVAALSCLMLVTALGSQA (SEQ ID NO: 15); the stanniocalcin signal sequence (MLQNSAVLLLLVISASA, SEQ ID NO:16); the invertase signal sequence (e.g., MLLQAFLFLLAGFAAKISA, SEQ ID NO:17); the yeast mating factor alpha signal sequence (e.g., *K. lactis* killer toxin leader sequence); a hybrid signal sequence (e.g., MKWVSFISLLFLFSSAYSRSLEKR, SEQ ID NO:18); an HSA/MFα-1 hybrid signal sequence (also known as HSA/kex2) (e.g., MKWVSFISLLFLFSSAYSRSLDKR, SEQ ID NO:19); a *K. lactis* killer/MFα-1 fusion leader sequence (e.g., MNIFYIFLFLLSFVQGSLDKR, SEQ ID NO:20); the Immunoglobulin Ig signal sequence (e.g., MGWSCIILFL-VATATGVHS, SEQ ID NO:21); the Fibulin B precursor signal sequence (e.g., MERAAPSRRVPLPLLLLGGLAL-LAAGVDA, SEQ ID NO:22); the clusterin precursor signal sequence (e.g., MMKTLLLFVGLLLTWESGQVLG, SEQ ID NO: 23); and the insulin-like growth factor-binding protein 4 signal sequence (e.g., MLPLCLVAALL-LAAGPGPSLG, SEQ ID NO:24).

Where it is desirable to produce recombinant MIS in a bacterial system, leader sequences can include bacterial leader sequences as disclosed in US Application 2011/0020868. A number of other secretion signals have been described for use in expressing recombinant polypeptides or proteins. See, for example, U.S. Pat. Nos. 5,914,254; 4,963,495; European Patent No. 0 177 343; U.S. Pat. No. 5,082,783; PCT Publication No. WO 89/10971; U.S. Pat. Nos. 6,156,552; 6,495,357; 6,509,181; 6,524,827; 6,528,298; 6,558,939; 6,608,018; 6,617,143; 5,595,898; 5,698,435; and 6,204,023; 6,258,560; PCT Publication Nos. WO 01/21662, WO 02/068660 and U.S. Application Publication 2003/0044906; U.S. Pat. No. 5,641,671; and European Patent No. EP 0 121 352, which are incorporated herein in their entirety by reference.

Modified Cleavage Sites

As discussed herein, the preparation of a MIS protein for preclinical use is complex and inefficient. Human MIS protein is produced from a pre-proprotein, which comprises a leader sequence. The leader sequence (amino acids 1-25 of SEQ ID NO: 1) is cleaved off and the remaining protein (often called "holo-human MIS"), and corresponding to amino acid residues 26-560 of SEQ ID NO:1, must be additionally post-translationally cleaved to result in an N-terminal and an C-terminal domain. These N-terminal and C-terminal domains form a monomer, and two identical monomers (comprising the N- and C-terminal domains) form together to generate a homodimer Holo-human MIS is cleaved into its N- and C-terminal domains most likely by means of furin or a related prohormone convertase PC5, expressed in the gonads. Cleavage occurs primarily at a kex-like site characterized by $R^{-4}XXR^{-1}$ with a serine in the +1 site, which makes the MIS cleavage site monobasic, but more furin/hex consensus. The purified C-terminal domain is the biologically active moiety and cleavage is required for biological activity. A secondary cleavage site, whose significance is unknown, is observed less frequently at residues 229-230 (which correspond to amino acids 254-255 of SEQ ID NO: 1). Non-cleavable mutants of MIS are not biologically active and mutations in the human gene that truncate the carboxy-terminal domain lead to persistent Mullerian duct syndrome. The cleavage of recombinantly expressed MIS protein by CHO cells is incomplete and inefficient, thus cleavage with an exogenous serine protease such as plasmin is required to enhance bioactivity.

Herein, the inventors have modified the kex-like site characterized by $R^{-4}XXR^{-1}$ with an R in the -2 site, which makes the monobasic MIS cleavage site more like a consensus Kex/Furin recognition site. In particular, in one embodiment, the recombinant human MIS is produced from a proprotein where the amino acid residue at position 450 of SEQ ID NO: 1 has been changed from a Q (glutamine or Gln) to a R (arginine, or Arg). This mutation can be referred to as Q450R of SEQ ID NO:1. This corresponds to a change in amino acid residue 425 (Q425R) of MIS which is numbered with conventional protein numbering, where the first numbered amino acid begins after the leader sequence.

This change in amino acid sequence of Q450R of SEQ ID NO:1 allows for production of a highly purified cleaved preparation of human MIS protein which has full bioactivity.

In alternative embodiments, the primary cleavage site in the MIS protein, e.g., the monobasic site which is located at amino acid position 426-427 of human wild-type MIS (corresponding to amino acid 451-452 of SEQ ID NO:1 herein) can be modified to an amino acid recognition site which is recognized by a different cleavage enzyme. For example, the primary cleavage site in the MIS protein, e.g., the monobasic site which is located at amino acid position 426-427 can be modified to an amino acid sequence which is recognized by a protease or peptidase, such as pro-hormone convertases (PC's), or other cleaving agents expressed by a cell and found in surrounding tissue, or produced by a microbe capable of establishing an infection in a mammal. Enzyme-cleavable peptides can, but are not required to, contain one or more amino acids in addition to the amino acid recognition sequence; additional amino acids can be added to the amino terminal, carboxy terminal, or both the amino and carboxy terminal ends of the recognition sequence. Means of adding amino acids to an amino acid sequence, e.g., in an automated peptide synthesizer, as well as means of detecting cleavage of a peptide, e.g., by chromatographic analysis for the amino acid products of such cleavage, are well known to ordinarily skilled artisans given the teachings of this invention.

Prohormone protein convertases constitute a family of serine proteases structurally related to bacterial subtilisins and to yeast kexin. Several eukaryotic members of this family are currently known. Pro-hormone Convertases (PC's) cleave precursor polypeptides at specific basic residues, most often after selected paired basic residues, to generate bioactive peptide and proteins. Many members of the insulin family of proteins (e.g. Insulin, Igf-1) are substrates for PC's.

Tags to Enhance Purification

In some embodiments, a recombinant MIS protein comprises at least one internal label or "tag". In some embodiments the tag can be, for example, a c-myc, poly histidine, or FLAG tag. In some embodiments, the tag is a FLAG tag, for example, a FLAG tag of SEQ ID NO:8. A FLAG tag can be encoded by the nucleic acid of SEQ ID NO 9.

In some embodiments, the tag on the recombinant human MIS protein is internal at the carboxy terminus immediately downstream from the cleavage site. As it is the most flexible part of the C-terminus and not involved in binding to receptor and rendering specificity, as are the "fingertips" of the C-terminus (Papakostas et al, 2010, Lorenzo et al, 2002). In some embodiments, the labeling at this site is most likely to preserve biologic activity. In some embodiments, a tag, e.g., a FLAG tag is located after the primary cleavage site, e.g., after amino acid 450 of SEQ ID NO: 1 (corresponding to amino acid residue 425 of conventional protein nomenclature). In some embodiments, a tag is located between amino acid residues 452 and 453 of SEQ ID NO: 1 (which corresponds with amino acid residues 427 and 428 under normal amino acid nomenclature of MIS protein).

In alternative embodiments, the tag or label is located at any position between sequence 450 and 560 of SEQ ID NO:

1. In some embodiments, the tag is inserted 2 amino acid residues after the modified amino acid at position 450 of SEQ ID NO: 1. However, a position of the tag at the N-terminus of the C-terminal domain of MIS is preferred, as it location at the C-terminus of the C-terminal domain renders the C-terminal domain totally inactive, significantly reducing the bioactivity of the MIS protein.

In some embodiments, a recombinant MIS protein comprises more than one tag, e.g., for example, at least 2 or at least 3, or at least 4 or more than 4 tags. In some embodiments, the tags are sequential (e.g., one after another) and in some embodiments, they are dispersed (e.g., intermittent) in the recombinant human MIS protein. Preferably, the tags do not interfere or substantially affect the bioactivity of the recombinant MIS protein function at binding and activating MISRII. In some embodiments, where the recombinant MIS protein comprises more than one tag, the tags are the same tag. In alternative embodiments, where the recombinant MIS protein comprises more than one tag, the tags are different tags, for example, a recombinant MIS protein can comprise a FLAG tag and a histidine tag. The small size of the Flag tag allows it to be contained in the flexible, non binding N-terminal domain of the C-terminus. Accordingly, in some embodiments, any tag known to a person of ordinary skill in the art can be used in place of the Flag Tag, for example a tag of between about 5-10 amino acids, or between about 10-15 amino acids, or a tag between about 15-20 amino acids, or a tag between 20-30 amino acids, or a tag between about 30-50 amino acids. In some embodiments, a tag greater than 50 amino acids in length is not recommended, as the tag may sterically hinder the flexible N-terminus of the C-terminal domain, and thus inhibit the bioactivity of the recombinant MIS protein.

In some embodiments, a tag-labeled, e.g., FLAG tagged recombinant human MIS protein, such as the LRF recombinant human MIS protein as disclosed herein (see FIG. 1) can be eluted by a single step to produce highly purified efficiently cleaved preparation with full bioactivity. When scaled-up, this purification of recombinant human MIS protein will be suitable for clinical applications; furthermore it will be useful for various binding assays in both clinical and experimental settings. Internal labeling of MIS during translation has proved to be more effective than labeling after purification of the protein as iodination or biotinylation greatly reduced MIS bioactivity. Surprisingly, the inventors have discovered that the LRF recombinant human MIS protein construct is more bioactive than the wild-type MIS. Inserting the FLAG tag sequence has several other distinct advantages. First, its unique amino acid domain is not present in any other gene (except for mouse brain phosphatase), thus making the anti-FLAG antibody very specific. Second, the elution of the protein with the 3x FLAG peptide is specific for the FLAG MIS and not other proteins that bind non-specifically to the agarose beads.

Surprisingly, a FLAG-tagged, cleavage optimized recombinant human MIS (e.g., a RF recombinant human MIS or RARR/S (SEQ ID NO: 27) FLAG MIS) was bioactive whereas a FLAG-tagged, non-cleavage optimized recombinant human MIS (e.g., RAQR/R (SEQ ID NO: 28) FLAG MIS) was not when compared to native human MIS or to the previously prepared untagged RAQR/R (SEQ ID NO: 28) MIS. As it is likely that the presence of the acidic FLAG tag so close to the cleavage site may impair the degree of cleavage, thus causing loss of activity. Thus, the inventors did not anticipate enhanced cleavage with the addition of the Flag tag. Moreover, the holo RAQR/R FLAG MIS ("RAQR/R" disclosed as SEQ ID NO: 28) preparation in CHO (or HEK) cells is not bioactive, as no endogenous processing occurs with the RAQR/R (SEQ ID NO: 28) cleavage site in contrast to what was reported by Kurian (Cancer Res., 1995. 1; 343-349) when the construct lacked the FLAG tag. On the other hand, the retention of the serine at position 428 and the conversion of the monobasic site to dibasic (corresponding to Q>R at amino acid position 425 using conventional protein nomenclature), or Q>R at position 450 of SEQ ID NO: 1) makes the endogenous cleavage more efficient and very specific. Furthermore, a tag such as a FLAG MIS is a powerful tool for binding studies, and can be used to immunoprecipitate the endogenous MISRII without cross-linking. Accordingly, in some embodiments, a labeled recombinant human MIS protein, e.g., a MIS with an internal FLAG is useful in an efficient method for producing a highly pure and biologically active internally labeled form of MIS, which can be used for scale-up for preclinical and clinical use, for the study of MIS binding proteins and for tracking in pharmacokinetic studies.

Variants of a Human Recombinant MIS Protein.

In some embodiments, a recombinant human MIS protein as disclosed can have a modification in the core MIS protein sequence, e.g., amino acids residues 26-560 of SEQ ID NO: 1 (including a modification of amino acid residue 450 from Q to R of SEQ ID NO: 1) and/or the insertion of a tag at the beginning of the C-terminal domain). Such variants are considered to be homologous to wild-type MIS protein.

As used herein, the term "polypeptide" refers to a polymer of amino acids and its equivalent and does not refer to a specific length of the product; thus, peptides, oligopeptides and proteins are included within the definition of a polypeptide. A derivative is a polypeptide having conservative amino acid substitutions, as compared with another sequence. Derivatives further include other modifications of proteins, including, for example, modifications such as glycosylations, acetylations, phosphorylations, and the like.

In some embodiments, a recombinant human MIS protein is at least 75%, at least 80%, at least 85%, at least 90% or at least 95% similar to the homologous recombinant human MIS protein. As used herein, "similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

Homologues and functional derivatives and functional fragments of MIS of SEQ ID NO: 1 are also encompassed for use in the present invention, and can also be identified, for example, by expression of MIS from an expression library. (See, e.g., Sambrook et al. (2001). Molecular cloning: a laboratory manual, 3rd ed. (Cold Spring Harbor, N.Y., Cold Spring Harbor Laboratory Press); Ausubel et al., supra.) A mutated endogenous gene sequence can be referred to as a heterologous transgene; for example, a transgene encoding a mutation in MIS which is not known in naturally-occurring genomes is a heterologous transgene with respect to murine and non-murine, e.g., human species. A MIS protein, such as, for example, those disclosed in U.S. Pat. Nos. 5,427,780, 5,359,033 and 5,661,126 (the disclosures of which are incorporated by reference herein).

The variation in primary structure of core human MIS protein sequence (e.g., amino acids residues 26-560 of SEQ ID NO: 1 (including a modification of amino acid residue 450 from Q to R of SEQ ID NO: 1) and/or the insertion of a tag at the beginning of the N-terminal domain of the C-terminal domain), or functional fragment, or a homologue are encompassed for use in the present invention, for instance, may include deletions, additions and substitutions. The substitutions may be conservative or non-conservative. The differences between a recombinant human MIS protein and a variant generally conserve desired properties, mitigate or eliminate undesired properties and add desired or new properties. For example, variants of a recombinant human MIS protein can have superior activity as compared to wild-type MIS protein.

It will be appreciated by those of skill that the core human MIS protein sequence (e.g., amino acids residues 26-560 of SEQ ID NO: 1) of a recombinant human MIS protein as disclosed herein can be readily manipulated to alter the amino acid sequence of a protein. A gene encoding the MIS protein or a functional fragment, homologue or variant thereof, can be manipulated by a variety of well known techniques for in vitro mutagenesis, among others, to produce variants of the naturally occurring human protein or fragment thereof, herein referred to as variants or muteins, may be used in accordance with the invention.

Other Modifications to a Recombinant Human MIS Protein

The recombinant human MIS protein useful in the present invention can also be modified at their amino termini, for example, so as to increase their hydrophilicity. Increased hydrophobicity enhances exposure of the peptides on the surfaces of lipid-based carriers into which the parent peptide-lipid conjugates have been incorporated. Polar groups suitable for attachment to peptides so as to increase their hydrophilicity are well known, and include, for example and without limitation: acetyl ("Ac"), 3-cyclohexylalanyl ("Cha"), acetyl-serine ("Ac Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

In some embodiments, a recombinant human MIS protein can be fused to one or more fusion partners. In certain embodiments, one of the fusion partners is the Fc protein (e.g., mouse Fc or human Fc). The fusion protein may further include a second fusion partner such as a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence).

In one embodiment, a recombinant human MIS protein fusion protein useful in the methods and compositions as disclosed herein can comprise a human Fc protein or a functional fragment thereof. Accordingly, in one embodiment, a recombinant human MIS protein fusion protein useful in the methods and compositions as disclosed herein can comprises a human Fc molecule as the first fusion partner, where the Fc fragment can be SEQ ID NO: 10 or functional variants or functional derivatives thereof, where SEQ ID NO: 10 is as follows:

```
LELVPRGSGDPIEGRGGGGGDPKSCDKPHTCPLCPAPELLGGPSVFLF
PPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKA
KGQPREPQVYTLPPSRDELTKNQVSLTCLVKGFYPSDIAVEWESNGQP
ENNYKATPPVLDSDGSFFLYSKLTVDKSRWQQGNVFSCSVMHEALHNH
YTQKSLSLSPGK
```

Variations and modifications to a recombinant human MIS protein and vectors can be used to increase or decrease recombinant human MIS protein expression, and to provide means for targeting. For example, a recombinant human MIS protein can be linked with a molecular targeting molecule for targeting cancer cells or ovarian cells, to make the recombinant human MIS protein specific for cancers or tissue specific to the ovary, respectively.

In one embodiment, a recombinant human MIS protein is fused to a second fusion partner, such as a carrier molecule to enhance its bioavailability. Such carriers are known in the art and include poly(alkyl)glycol such as poly ethylene glycol (PEG). Fusion to serum albumin can also increase the serum half-life of therapeutic polypeptides.

In some embodiments, a recombinant human MIS protein can also be fused to a second fusion partner, for example, to a polypeptide that targets the product to a desired location, or, for example, a tag that facilitates its purification, if so desired. In some embodiments, tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

In some embodiments, a recombinant human MIS protein or functional fragment thereof is modified to achieve adequate circulating half-lives, which impact dosing, drug administration and efficacy. Many approaches have been undertaken with the aim to increase the half-life of biotherapeutics. Small proteins below 60 kD are cleared rapidly by the kidney and therefore do not reach their target. This means that high doses are needed to reach efficacy. The modifications to a recombinant human MIS protein and fragments encompassed in the methods of the present invention to increase the half-life of proteins in circulation include: PEGylation; conjugation or genetic fusion with proteins, e.g., transferrin (WO06096515A2), albumin, growth hormone (US2003104578AA); conjugation with cellulose (Levy and Shoseyov, 2002); conjugation or fusion with Fc fragments; glycosylation and mutagenesis approaches (Carter, 2006), which are incorporated herein by reference.

In the case of PEGylation, polyethylene glycol (PEG) is conjugated to a recombinant human MIS protein or fragment, which can be for example a plasma protein, antibody or antibody fragment. The first studies regarding the effect of PEGylation of antibodies were performed in the 1980s. The conjugation can be done either enzymatically or chemically and is well established in the art (Chapman, 2002; Veronese and Pasut, 2005). With PEGylation the total size can be increased, which reduces the chance of renal filtration. PEGylation further protects from proteolytic degradation and slows the clearance from the blood. Further, it has been reported that PEGylation can reduce immunogenicity and increase solubility. The improved pharmacokinetics by the addition of PEG is due to several different mechanisms: increase in size of the molecule, protection from proteolysis, reduced antigenicity, and the masking of specific sequences from cellular receptors. In the case of antibody fragments (Fab), a 20-fold increase in plasma half-life has been achieved by PEGylation (Chapman, 2002).

To date there are several approved PEGylated drugs, e.g., PEG-interferon alpha2b (PEG-INTRON) marketed in 2000 and alpha2a (Pegasys) marketed in 2002. A PEGylated antibody fragment against TNF alpha, called Cimzia or Certolizumab Pegol, was filed for FDA approval for the treatment of Crohn's disease in 2007 and has been approved on Apr. 22, 2008. A limitation of PEGylation is the difficulty in synthesizing long monodisperse species, especially when PEG chains over 1000 kD are needed. For many applications, polydisperse PEG with a chain length over 10000 kD is used, resulting in a population of conjugates having different length PEG chains, which need extensive analytics to ensure equivalent batches between productions. The different length of the PEG chains may result in different biological activities and therefore different pharmacokinetics. Another limitation of PEGylation is a decrease in affinity or activity as it has been observed with alpha-interferon Pegasys, which has only 7% of the antiviral activity of the native protein, but has improved pharmacokinetics due to the enhanced plasma half-life.

In some embodiments, a recombinant human MIS protein or fragment thereof is conjugated with a long lived protein, e.g. albumin, which is 67 kD and has plasma half-life of 19 days in human (Dennis et al., 2002). Albumin is the most abundant protein in plasma and is involved in plasma pH regulation, but also serves as a carrier of substances in plasma. In the case of CD4, increased plasma half-life has been achieved after fusing it to human serum albumin (Yeh et al., 1992). Other examples for fusion proteins are insulin, human growth hormone, transferrin and cytokines (Ali et al., 1999; Duttaroy et al., 2005; Melder et al., 2005; Osborn et al., 2002a; Osborn et al., 2002b; Sung et al., 2003) and see (US2003104578A1, WO06096515A2, and WO07047504A2, herein incorporated in entirety by reference).

The effect of glycosylation on plasma half-life and protein activity has also been extensively studied. In the case of tissue plasminogen activator (tPA) the addition of new glycosylation sites decreased the plasma clearance, and improved the potency (Keyt et al., 1994). Glycoengineering has been successfully applied for a number of recombinant proteins and immunoglobulins (Elliott et al., 2003; Raju and Scallon, 2007; Sinclair and Elliott, 2005; Umana et al., 1999). Further, glycosylation influences the stability of immunoglobulins (Mimura et al., 2000; Raju and Scallon, 2006).

In some embodiments, a recombinant human MIS protein or fragments thereof can be fused to the Fc fragment of an IgG (Ashkenazi and Chamow, 1997). The Fc fusion approach has been utilized, for example in the Trap Technology developed by Regeneron (e.g. IL1 trap and VEGF trap). The use of albumin to extend the half-life of peptides has been described in US2004001827A1. Positive effects of albumin have also been reported for Fab fragments and scFv-HSA fusion protein (Smith et al., 2001). It has been demonstrated that the prolonged serum half-life of albumin is due to a recycling process mediated by the FcRn (Anderson et al., 2006; Chaudhury et al., 2003; Smith et al., 2001).

In some embodiments, a recombinant human MIS protein is conjugated to a biotinylated Fc protein, as disclosed in US application 2010/0209424, which is incorporated herein in its entirety by reference.

As used herein, the term "conjugate" or "conjugation" refers to the attachment of two or more entities to form one entity. For example, the methods of the present invention provide conjugation of a recombinant human MIS protein (i.e. SEQ ID NO: 2 or 3 or fragments or derivatives or variants thereof) joined with another entity, for example a moiety such as a first fusion partner that makes the recombinant human MIS protein stable, such as Ig carrier particle, for example IgG1 Fc. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, a recombinant human MIS protein (i.e. SEQ ID NO: 2 or 3 or fragments, derivatives or variants thereof), can be linked to the first fusion partner via any suitable means, as known in the art, see for example U.S. Pat. Nos. 4,625,014, 5,057,301 and 5,514,363, which are incorporated herein in their entirety by reference. For example, a recombinant human MIS protein can be covalently conjugated to the IgG1 Fc, either directly or through one or more linkers. In one embodiment, a recombinant human MIS protein as disclosed herein is conjugated directly to the first fusion partner (e.g. Fc), and in an alternative embodiment, a recombinant human MIS protein as disclosed herein can be conjugated to a first fusion partner (such as IgG1 Fc) via a linker, e.g. a transport enhancing linker.

A large variety of methods for conjugation of a recombinant human MIS protein as disclosed herein with a first fusion partner (e.g. Fc) are known in the art. Such methods are e.g. described by Hermanson (1996, Bioconjugate Techniques, Academic Press), in U.S. Pat. Nos. 6,180,084 and 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a recombinant human MIS protein can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as a recombinant human MIS protein to be conjugated.

Suitable methods for conjugation of a recombinant human MIS protein as disclosed herein with a first fusion partner (e.g. Fc) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a recombinant human MIS protein as disclosed herein with a first fusion partner (e.g. Fc), for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multi-step protocols can offer a great control of conjugate size and the molar ratio of components.

The term "linker" refers to any means to join two or more entities, for example a recombinant human MIS protein as disclosed herein with a first fusion partner (e.g. Fc). A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of a recombinant human MIS protein as disclosed herein or the first fusion partner (e.g. Fc) are preferred.

Targeting.

In some embodiments, a recombinant human MIS protein, or functional fragment, or a homologue for use in the methods and compositions as disclosed herein can be targeted to a cancer or ovarian cells via a targeting ligand. A targeting ligand is a molecule, e.g., small molecule, protein or fragment thereof that specifically binds with high affinity to a target, e.g., a cell-surface marker on a pre-selected cell, such as a surface protein such as a receptor that is present to a greater degree on the pre-selected cell target than on any other body tissue. Accordingly, in some embodiments, a recombinant human MIS protein for use in the compositions and methods as disclosed herein can be fused to a Fc and/or optionally also to a targeting molecule. In some embodiments, a nucleic acid encoding a targeting ligand can be fused to a nucleotide encoding a recombinant human MIS protein or fragment or homologue or variant thereof. Another example of a targeting ligand is a group of cadherin domains from a human cadherin. A targeting ligand component attached to a recombinant human MIS protein can include a naturally occurring or recombinant or engineered ligand, or a fragment thereof, capable of binding the pre-selected target cell.

Further examples of targeting ligands also include, but are not limited to, antibodies and portions thereof that specifically bind a pre-selected cell surface protein with high affinity. By "high affinity" is meant an equilibrium dissociation constant of at least molar, as determined by assay methods known in the art, for example, BiaCore analysis. In one embodiment, the targeting ligand may also comprise one or more immunoglobulin binding domains isolated from antibodies generated against a selected tissue-specific surface protein or target tissue-specific receptor. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a tissue-specific surface protein, a target tissue-specific receptor, or portion thereof. If the intended targeting fusion polypeptide will be used as a mammalian therapeutic, immunoglobulin binding regions should be derived from the corresponding mammalian immunoglobulins. If the targeting fusion polypeptide is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, lgG, 1gM, IgA, 1gD, and IgE, respectively. Within each lgG class, there are different isotypes (e.g. lgG1, lgG2, etc.). Typically, the antigen-binding region of an antibody will be the most critical in determining specificity and affinity of binding.

An exemplary immunoglobulin (antibody) structural unit of human lgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" (VL) and variable heavy chain (VH) refer to these light and heavy chains respectively. Antibodies exist as intact immunoglobulins, or as a number of well-characterized fragments produced by digestion with various peptidases. For example, pepsin digests an antibody below the disulfide linkages in the hinge region to produce F(ab)'2, a dimer of Fab which itself is a light chain joined to VH-CH by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms immunoglobulin or antibody, as used herein, also includes antibody fragments either produced by the modification of whole antibodies, or those synthesized de novo using recombinant DNA methodologies (e.g., single chain Fv)(scFv)) or those identified using phase display libraries (see, for example, McCafferty et al. (1990) Nature 348:552-554). In addition, the fusion polypeptides of the invention include the variable regions of the heavy (VH) or the light (VL) chains of immunoglobulins, as well as tissue-specific surface protein and target receptor-binding portions thereof. Methods for producing such variable regions are described in Reiter, et al. (1999) J. Mol. Biol. 290:685-698.

Methods for preparing antibodies are known to the art. See, for example, Kohler & Milstein (1975) Nature 256: 495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion polypeptides and methods of the instant invention. Also, transgenic mice, or other organisms such as other mammals, may be used to express human or humanized antibodies. Alternatively phage display technology can be used to identify antibodies, antibody fragments, such as variable domains, and heteromeric Fab fragments that specifically bind to selected antigens.

Screening and selection of preferred immunoglobulins (e.g., antibodies) can be conducted by a variety of methods known to the art: Initial screening for the presence of monoclonal antibodies specific to a tissue-specific or target receptor may be conducted through the use of ELISA-based methods or phage display, for example. A secondary screen is preferably conducted to identify and select a desired monoclonal antibody for use in construction of the tissue-specific fusion polypeptides of the invention. Secondary screening may be conducted with any suitable method known to the art. One method, termed "Biosensor Modification-Assisted Profiling" ("BiaMAP") (US patent publication 2004/101920), allows rapid identification of hybridoma clones producing monoclonal antibodies with desired characteristics. More specifically, monoclonal antibodies are sorted into distinct epitope-related groups based on evaluation of antibody: antigen interactions.

Production of Recombinant Human MIS Proteins

Recombinant human MIS proteins as disclosed herein, and functional fragments and derivatives thereof can be obtained by any suitable method. For example, polypeptides can be produced using conventional recombinant nucleic acid technology such as DNA or RNA, preferably DNA. Guidance and information concerning methods and materials for production of polypeptides using recombinant DNA technology can be found in numerous treatises and reference manuals. See, e.g., Sambrook et al, 1989, Molecular Cloning—A Laboratory Manual, 2nd Ed., Cold Spring Harbor Press; Ausubel et al. (eds.), 1994, Current Protocols in Molecular Biology, John Wiley & Sons, Inc.; Innis et al. (eds.), 1990 PCR Protocols, Academic Press.

Alternatively, recombinant human MIS proteins or functional fragments thereof can be obtained directly by chemical synthesis, e.g., using a commercial peptide synthesizer according to vendor's instructions. Methods and materials for chemical synthesis of polypeptides are well known in the art. See, e.g., Merrifield, 1963, "Solid Phase Synthesis," J. Am. Chem. Soc. 83:2149-2154.

In some embodiments, a recombinant human MIS protein, or functional fragment or derivative or variant thereof can be expressed in the cell following introduction of a DNA encoding the protein, e.g., a nucleic acid encoding recombinant human MIS proteins or homologues or functional derivatives thereof, e.g., in a conventional expression vector as disclosed herein or by a catheter or by cells transformed with the nucleic acid ex vivo and transplanted into the subject.

Assays to Determine the Activity of the Recombinant Human MIS Protein

In one embodiment, an Organ Culture Assay System can be used to assay the bioactivity of a human recombinant MIS protein as disclosed herein. The assay system used was described by Donahoe et al, J. Surg. Res., 23, 141-148, 1977 which is the Mullerian regression organ culture assay. The urogenital ridge was dissected from the 14-day female rat embryo and transferred to an organ culture dish (Falcon, 3010). Specimens were placed on stainless-steel grids coated with a thin layer of 2% agar and incubated for 72 hr at 37 .degree. C. in 5% $CO_2$ and 95% air over 2 ml of culture medium [CMRL 1066 containing 10% fetal calf serum, 1% penicillin (10,000 units/ml)] or a 1:1 mixture of culture medium and the supernatant or gradient fraction to be tested. The incubated tissue was then coated with a mixture of 2% agar and albumin at 44 .degree. C., fixed in buffered formaldehyde, dehydrated in ethanol, cleaned in xylene, and embedded in paraffin. Eight-micrometer serial sections were stained with hematoxylin and eosin for viewing by light microscopy. Sections from the cephalic end of the Mullerian duct were assigned a coded number and graded for regression (Donahoe et al, Biol. Reprod., 15, 329-334, 1976) on a scale of 0 to V. Five slides with six to eight sections per slide were read for each assay. A grade of activity was listed as the nearest whole number to the mean. A test group for the fractionation procedures represents at least 10 assays. If the mean fell midway between two numbers, then both numbers were listed. Grade 0 refers to no regression. The Mullerian duct, which is lined with columnar epithelial cells whose nuclei have a basilar orientation, has a widely patent lumen. Grade I is minimal regression. The duct is slightly smaller, and either the surrounding mesenchyme is condensed around the duct as seen in plastic sections or there is a clear area around the duct as seen in paraffin sections. Grade II refers to mild regression. The duct is smaller, and the mesenchymal condensation or the clear area around the duct is more pronounced. The nucleii of the shorter epithelial cells loose their basilar orientation. Grade III is moderate regression. The duct is very small and disorganized. The tip of the urogenital ridge develops poorly distal to the Wolffian duct. Grade IV is severe regression. The duct is replaced by a whorl of cells. Grade V refers to complete regression. No remnant of the duct can be detected. Positive tissue controls, using fetal testis, and negative tissue controls, where the Mullerian ducts were incubated alone or with muscle were included in each experiment. Mullerian ducts exposed to extracts from non-testicular tissue, to inactive testicular fractions, or to saline served as biochemical controls. Aliquots of all fractions were dialyzed against distilled water and freeze-dried, and protein content was measured.

Delivery of Recombinant Human MIS Protein

Methods known in the art for the therapeutic delivery of a recombinant human MIS protein and/or nucleic acids encoding the same can be used for treating a disease or disorder, such as cancer in a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

In some embodiments, the recombinant human MIS protein is cleaved in vitro to form a bioactive halo-dimer of MIS, comprising two identical monomers, each consisting of the N-terminal domain and the C-terminal domain, and then administered to a subject.

Various delivery systems are known and can be used to administer a recombinant human MIS protein (before or after it has been cleaved into its bioactive form) to a subject, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. A recombinant human MIS protein can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions comprising a recombinant human MIS protein, before or after cleavage into its bioactive form, into the central nervous system by any suitable route, including intraventricular and intrathecal injection; intraventricular injection may be facilitated by an intraventricular catheter, for example, attached to a reservoir, such as an Ommaya reservoir Pulmonary administration can also be employed, e.g., by use of an inhaler or nebulizer, and formulation with an aerosolizing agent.

Methods to Treat Proliferative Diseases and Cancer

One aspect of the present invention provides methods for treating cancers, e.g., cancers which express MISRII in a subject. Accordingly, one aspect of the present invention relates generally to a method of treating a proliferative disease or disorder in a subject, where the proliferative disease or disorder is associated with cells that express a MIS receptor, for example cells expressing MISRII. In some embodiments, the proliferative disease or disorder is cancer, where the cancer or cancer cells express at least one MIS receptor, for example cancer or cancer cells expressing MISRII. The method of the present invention comprises the administration of an effective amount of a recombinant human MIS protein as disclosed herein or a functional fragment or derivative thereof to a subject in with a proliferative disorder, where the cells associated with the proliferative disorder express at least one MIS receptors, for example the cells express MISRII. For example, an effective amount of a recombinant human MIS protein as disclosed herein or a functional fragment is administered to a subject with a cancer expressing at least one MIS receptors, for example expressing MISRII. Thus, by using the methods of the present invention, one can intervene in the proliferative disease, for example cancer, ameliorate the symptoms, and in some cases cure the disease. In some embodiments, the recombinant human MIS protein that can be used for treating proliferative diseases and cancer comprises the amino acid sequence residues 25-559 of SEQ ID NO: 2 or a functional fragment thereof.

Examples of such diseases where proliferation of cells expressing at least one MIS receptors, for example expressing MISRII is the cause of disease are cancers, for example cervical cancer and ovarian cancer. In some embodiments, the cancer expressing at least one MIS receptor, for example MISRII is a cancer cell. In some embodiments, such a cancer cell expressing at least one MIS receptors, for example expressing MISRII is, for example but not limited to, an ovarian cancer cell, vulvar epidermal carcinoma cell, cervical carcinoma cell, endometrial edenocarinaoma cell, ovarian adenocarcinoma.

In alternative embodiments, the cancer expressing at least one MIS receptor, for example cancers expressing MISRII are for example but not limited to; breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

In alternative embodiments, the present invention relates to the use of a recombinant human MIS protein as disclosed herein or a functional fragment or derivative or variant thereof for the treatment of any disorder where administration of the MIS protein or a nucleic acid encoding MIS protein or activation MISRII is whole or part of the therapeutic regime.

In some embodiments, the cancer is a MIS-responsive cancer, for example but not limited to ovarian cancer and cervical cancer. In some embodiments, the cancer expresses MISRII, for example but not limited to ovarian cancer and cervical cancer. In some embodiments, the disorder is a disorder associated with excess androgen states, for example as disclosed in U.S. Pat. No. 6,673,352, which is incorporated in its entirety herein by reference. In some embodiments, the methods of the present invention are used in the treatment of prostatic cancer, polycysic ovarian disease, benign prostatic hypertrophy and precocious puberty.

In some embodiments, the cancer is a chemotherapeutic-resistant or multi-drug resistant cancer, e.g., where the cancer is a paclitaxel, cisplatin, rapamycin, pyrazoloanthrone, or Doxorubicin-resistant cancer.

In a related embodiment, a tissue to be treated is a tumor tissue expressing at least one MIS receptor, for example expressing MISRII of a subject, for example the tumor tissue is, but not limited to a solid tumor, a metastases, a skin cancer, a breast cancer, an ovarian cancer, an cervical cancer, a hemangioma or angiofibroma and the like cancer. Typical solid tumor tissues treatable by the pharmaceutical composition of the invention, includes for example, but not limited to tumors of the lung, pancreas, breast, colon, laryngeal, ovarian, and the like tissues. In some embodiment, the solid tumor tissue treatable by the present methods include thyroid, and the cancer type is medullary thyroid cancer.

In a related embodiment, the invention contemplates the practice of the method of administering a composition comprising a recombinant human MIS protein as disclosed herein or a functional fragment in conjunction with other therapies such as conventional chemotherapy directed against solid tumors and for control of establishment of metastases. For example, a chemotherapeutic agent used in chemotherapy include, but is not limited to, paclitaxel, cisplatin, doxorubicin, rapamycin, pyrazoloanthrone, including but not limited to antra(1,9-cd)pyrazol-6(2H)-one (SP600125) or N1-methyl-1,9-pyrazoloanthrone (M-SP600125) or a functional derivative or functional analogue thereof. In some embodiments, a chemotherapeutic agent is a radiotherapeutic agent. The administration of the compounds described herein is typically conducted prior to and/or at the same time and/or after chemotherapy, although it is also encompassed within the present invention to inhibit cell proliferation after a regimen of chemotherapy at times where the tumor tissue will be responding to the toxic assault by inducing angiogenesis to recover by the provision of a blood supply and nutrients to the tumor tissue. In addition, the pharmaceutical compositions of the invention for the treatment of proliferative disorders, for example cancer, can be administrated prophylatically and/or before the development of a tumor, if the subject has been identified as to have a risk of developing cancer, for example to subjects that are positive for biomarkers of cancer cells or tumors. Insofar as the present methods apply to inhibition of cell proliferation, the methods can also apply to inhibition of tumor tissue growth, to inhibition of tumor metastases formation, and to regression of established tumors.

In some embodiments, the expression of Mullerian Inhibiting Substance (MIS) receptor is measured in a biological sample obtained from the subject, e.g., a cancer or tumor tissue sample or a cancer cell or tumor cell, e.g., a biopsy tissue sample.

The presence of MISRII in the cells in fluids such as blood may be indicative of the presence of cancer. The presence of MISRII in fluids or sites not near a tumor may be indicative of metastasis. In some such embodiments, the compounds of the present invention are administered to the subject, and in some embodiments the compounds of the present invention are administered to the subject in a pharmaceutical composition comprising one or more additional therapies.

The inventive methods disclosed herein provide for the parenteral and oral administration of a recombinant human MIS protein as disclosed herein or a functional fragment or derivative thereof, in combination with other pharmaceutical compositions to subjects in need of such treatment. Parenteral administration includes, but is not limited to, intravenous (IV), intramuscular (IM), subcutaneous (SC), intraperitoneal (IP), intranasal, and inhalant routes. In the method of the present invention, a recombinant human MIS protein as disclosed herein or a functional fragment or analogs thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the subject. In general, a dose that is administered by subcutaneous injection will be greater than the therapeutically-equivalent dose given intravenously or intramuscularly. Preferably, the dose of compounds of the present invention will be administered at doses from about 0.1 mg to about 250 mg. In some embodiments, the dose of compounds of the present invention will be from about 1 mg to about 60 mg.

The methods of the present invention for treating cancer expressing at least one MIS receptor, for example expressing MISRII, are useful for treatment of proliferation-related diseases or cancer, which is associated with cells expressing at least one MIS receptor, for example MISRII, comprising contacting a tissue in which proliferation is occurring, or is at risk for occurring, with a composition comprising a therapeutically effective amount of a recombinant human MIS protein as disclosed herein or a functional fragment or functional derivatives thereof.

In some embodiments, the subject treated by the methods of the present invention in its many embodiments is a human subject, although it is to be understood that the principles of the invention indicate that the invention is effective with respect to all mammals. In this context, a mammal is understood to include any mammalian species in which treatment of diseases associated with cancer or a proliferative-related disorder is desirable, particularly agricultural and domestic mammalian species, as well as transgenic animals.

Uses

In another embodiment, the present invention provides a method for treating a variety of conditions by administering an effective amount of a recombinant human MIS protein or functional derivatives thereof of the invention to a subject in need thereof. Conditions that may be treated by the compounds of this invention, or a pharmaceutical composition containing the same, include any condition which is treated or reduces the symptoms by administration of MIS or activation of MIS signaling or activation of MISRII, and thereby benefit from administration of a recombinant human MIS protein or functional derivatives thereof. Representative conditions in this regard include, for example, but not limited to, cancers that express MIS receptors, for example cancer that express MISRII, for example, but not limited to ovarian, cervical and endometrial cancer. Other conditions which can be treated with MIS or activation of MIS signalling reduces the symptoms are, for example, rheumatoid arthritis, proliferative diseases such as cancer, treatment of prostatic cancer, polycysic ovarian disease, benign prostatic hypertrophy and precocious puberty and other hyperandrogen disorders such as testotoxicosis.

Accordingly, the present invention relates to the use of a recombinant human MIS protein or functional derivatives thereof for the treatment of any disorder where administration of the MIS protein or a nucleic acid encoding MIS protein or a functional derivative of MIS or activation MISRII is whole, or part, of the therapeutic regime. In some embodiments, the recombinant human MIS protein that can be used comprises the amino acid residues 25-559 of SEQ ID NO: 2 or a functional fragment thereof.

In some embodiments, the methods of the present invention are directed to use of a recombinant human MIS protein or functional derivatives thereof with other therapeutic agents, for example chemotherapy agents, wherein the chemotherapy agents, for example paclitaxel or MIS can be used at a lower dose that results in decreased side effects.

Uses of a Recombinant Human MIS Protein or Functional Derivatives or Analogues Thereof for the Treatment of Excess Androgen States In another embodiment, a recombinant human MIS protein or functional derivatives or analogues thereof, can be used for the treatment of a disorder associated with excess androgen production in a subject. The inventors have previously demonstrated that the administration of MIS protein and/or MIS nucleic acid decreases levels of androgen in a subject, and decreases serum levels of androgen in a subject, as disclosed in U.S. Pat. No. 6,673,352 and U.S. patent application Ser. No. 10/683,346, which are incorporated herein in their entirety by reference. Transgenic mice that overexpress MIS have also shown to have decreased serum testosterone concentrations, and administration of MIS results in decreased serum testosterone levels (Sriraman et al., J Androl. 2001, 22(5):750-8 and Trbovich et al., PNAS, 2001 Mar. 13; 98(6):3393-7). MIS has also been demonstrated to suppress both androgen-stimulated growth and androgen-independent survival of cells, and MIS regulates prostate growth by suppressing testicular testosterone synthesis also direct regulates androgen-induced gene expression and growth in the prostate at the cellular level (Trann et al, Mol Endocrinol. 2006, 20(10):2382-91).

Androgen stimulates or controls the development and maintenance of masculine characteristics in vertebrates by binding to androgen receptors. Androgens are also known as androgenic hormones or testoids, and are also the precursor of all estrogens, the female sex hormones. The primary and most well-known androgen is testosterone.

Without wishing to be bound by theory, excessive androgen production by the adrenal glands and/or the ovary, results in androgen excess and can result from increased local tissue sensitivity to circulating androgens. Androgen excess affects different tissues and organ systems, causing clinical conditions ranging from acne to hirsutism to frank virilization.

Hyperandrogenism, which refers to the excess production and secretion of androgens and precursors, is a common and sometimes serious endrocrinopathy for women of reproductive age. The excess androgens and precursors originate from the adrenal glands and ovaries in various proportions and manifest in varying effects depending on the amount of excess androgen. Clinical manifestations range from hirsutism (excessive hair growth of male pattern, sometimes accompanied by acne) to virilization (clitorimegaly, temporal balding, deepening of voice, or enhanced musculature).

Hyperandrogenism occurs as part of a wide spectrum of disease manifestations, including polycystic ovary syndrome (PCOS) which is a variable combination of hirsutism, infertility, obesity, insulin resistance and polycystic ovaries, the HAIR-AN syndrome (hyperandrogenism, insulin resistance and acanthosis *nigricans*), ovarian hyperthecosis (HAIR-AN with hyperplasia of luteinized theca cells in ovarian stroma), and other manifestations of high intraovarian androgen concentrations (e.g., follicular maturation arrest, atresia, anovulation, dysmenorrhea, dysfunctional uterine bleeding, infertility), androgenproducing tumors (virilizing ovarian or adrenal tumors).

Hirsutism is excessive recognizable hair growth characterized by an increase in the number and length of terminal hairs in androgen-sensitive areas. Racial, familial, genetic, and ethnic differences all affect the occurrence of hirsutism. Hirsutism is difficult to quantitate. The entire body needs to be inspected and the findings must be documented carefully. Particular attention should be directed to the chin, lip, sideburns, breasts, and sternum, the midline between the umbilicus and the pubis and the thigh.

Ferriman and Gallwey published a rating scale for grading hirsutism and is commonly known by persons of ordinary skill in the art. This scale allows the physician to measure a response to therapy objectively. This system is the most widely used and evaluates body areas for absent-to-severe hirsutism with scores of 0-4, respectively. Scores of 8 and higher are consistent with a diagnosis of hirsutism. This scale does not measure the thickness of the hair, which is another way of objectively assessing excess hair. Scoring systems are a useful aid in quantifying hirsutism and in evaluating treatment response. Even with scores greater than 8, the patient provides the definition. From a clinical standpoint, the patient can determine if he or she notices a difference. Photographs are helpful for documentation and for following the progress of therapy.

Virilization is relatively uncommon; it occurs with extreme hyperandrogenism. Virilization is characterized by temporal balding, breast atrophy, androgenic muscle development, clitoral hypertrophy, amenorrhea, deepening of the voice, and extreme hirsutism.

Current medical therapies for women are directed against the adrenals, the ovaries or the androgen receptor. Glucocorticoid therapy is directed against the adrenal glands but is limited, in some cases, by unwanted suppression of cortisol synthesis. GnRH therapy is directed against the ovaries, but is expensive, and its long-term effects are unknown. Further, therapy using oral contraceptives may be unsuitable because most contain progestins with androgenic activity.

Because the abnormal production of androgens is implicated in the pathways of many diseases and/or disorders for which there are no acceptable treatments, a need exists to find small molecules to inhibit the production of gonadotropins and/or androgens in mammals for their treatment and/or prophylaxis.

Accordingly, in one embodiment, a recombinant human MIS protein or functional derivatives or analogues thereof, can be used for the treatment of a disorder associated with excess androgen production in a subject. In some embodiments, the recombinant human MIS protein that can be used comprises the amino acid residues 25-559 of SEQ ID NO: 2 or a functional fragment thereof.

The term "androgen" is used herein to mean steroids that encourage the development of male sex characteristics and include the steroid derivatives of androstane including, testosterone, androstenedione, and analogs.

As used herein, a disease state or disorder characterized by "androgenic dependency" is a disease state which is exacerbated by, or caused by, insufficient, excessive, inappropriate or unregulated androgen production. Examples of such diseases in men include, but are not limited to, BPH, metastatic prostatic carcinoma, testicular cancer, androgen dependent acne, male pattern baldness and precocious puberty in boys. Examples of such diseases in women include, but are not limited to, hyperandrogenism, hirsutism, virilization, POCS, HAIR-AN syndrome, ovarian hyperthecosis, follicular maturation arrest, atresia, anovulation, dysmenorrhea, dysfunctional uterine bleeding, infertility, androgen-producing tumors.

As used herein, "androgen inhibiting" refers to an effective amount of an the pyrazoloanthrone or functional derivatives or analogues thereof as defined herein, such as SP600125, which will cause a decrease in the in vivo levels of the androgen to normal or sub-normal levels, when administered to a subject for the prophylaxis or treatment of a disease state which is exacerbated by, or caused by, excessive or unregulated androgen production.

In some embodiments, a recombinant human MIS protein or functional derivatives or analogues thereof as disclosed herein, can be used to treat prostate cancer. The impact of androgens on prostate carcinoma is known, as is the treatment of prostate cancer by androgen deprivation, including androgen blockade and inhibition of androgen synthesis (Huggins et al., Archs. Surg., Vol. 43, pp. 209-223 (1941)). J. Steroid Biochem. Molec. Biol., Vol. 37, pp. 349-362 (1990)). In addition, steroid hormones are widely used as contraceptives. Anti-spermatogenic agents are male contraceptives that inhibit spermatogenesis, the process leading to mature spermatazoa. Drugs that interfere in this process include androgens and anti-androgens. Since the anti-androgenic effects of a recombinant human MIS protein or functional derivatives or analogues thereof as disclosed herein are reversible, the recombinant human MIS protein can also be used as a male contraceptive agent. Korolkovas, A., Essentials Of Medicinal Chemistry, Second Edition, pp. 1032 (1988).

In some embodiments, other agents can be used in combination with the pharmaceutical compositions comprising a recombinant human MIS protein or functional derivatives or analogues thereof as disclosed herein for the treatment of excess androgen in a subject. In some embodiments, the agents function to lower the serum-free androgen levels and blocking the peripheral androgen action. Examples of such agents include, but are not limited to, suppression of ovarian androgens by administration of estrogens and/or progestins (i.e., contraceptive pill) or GnRH agonist and add-back estrogen therapy; suppression of adrenal androgens by administration of glucocorticoids (such as dexamethasone, prednisolone), antiandrogens (such as spironolactone, flutamide, cyproterone acetate), 5α-reductase inhibitor (such as finasteride), bromocriptine, and insulin-sensitizing drugs (such as metformin, thiazolidinediones).

Subjects amenable to treatment with a recombinant human MIS protein or functional derivatives or analogues thereof by the methods as disclosed herein are subjects that have been identified with a disease or disorder associated with excess androgen levels, such as, for example disorders such as, but not limited to BPH, prostate carcinoma, benign prostic hypertrophy, testicular cancer, androgen dependent acne, male pattern baldness, precocious puberty, hyperandrogenism, hirsutism, virilization, POCS, HIAR-AN syndrome, ovarian hyperthecosis, follicular maturation arrest, atresia, anovulation, dysmenorrheal, dysfunctional uterine bleeding, infertility and androgen-producing tumors.

In some embodiments, subjects amenable to treatment with a recombinant human MIS protein orfunctional derivatives or analogues thereof by the methods as disclosed herein are subjects with congenical adrenal hyperplasma (CAH), which can be commonly identified by one of ordinary skill in the art. CAH is most typically an autosomal recessive disorder where the enzyme 21-hydrolase is missing or functionally deficent. Alternatively subjects with CAH can have a loss and/or reduction in the function of 11α-hydroxylase enzyme and/or a 3α-hydroxy-steroid dehydrogenase enzyme. When these enzymes are missing or functioning at low levels, the body cannot make adequate amounts of the adrenal steroid hormones cortisol and aldosterone. High levels of ACTH that stimulate adrenal hyperplasia and hypersecretion of androgen precursors for cortisol and aldosterone synthesis ensue. CAH can appear in utero or develop postnatally. Pseudohermaphroditism may be present at birth.

The 21-hydroxylase deficiency is the most common autosomal-recessive disorder (more common than cystic fibrosis) and manifests itself with elevated levels of 17-hydroxy-progesterone. The 11a-hydroxylase deficiency is characterized by elevated levels of 11-deoxy-cortisol (compound S) and results in elevated levels of deoxycorticosterone (DOC), a mineralocorticoid. Hypertension and hypokalemia can be a prominent feature of 11a-hydroxylase deficiency. Another form of CAH, 3a-hydroxy-steroid dehydrogenase deficiency, results in elevated levels of pregnenolone, 17-hydroxy-pregnenolone, and DHEA. This condition is lethal if not detected because no corticosteroids are synthesized.

A partial defect in the above enzymes that manifests after puberty results in elevated levels of adrenal steroids via the same mechanism. The elevations are not as marked as they are with the congenital condition and this condition is referred to as nonclassical (maturity-onset or late-onset) CAH. Accordingly, in some embodiments, subjects amenable to treatment with a recombinant human MIS protein or functional derivatives or analogues thereof by the methods as disclosed herein are subjects with nonclassical (maturity-onset or late onset) CAH.

In some embodiments, subjects amenable to treatment with a recombinant human MIS protein or functional derivatives or analogues thereof by the methods as disclosed herein are female subjects with testosterone levels about or exceeding 2.0 ng/mL (200 ng/dL, 8.92 nmol/L) or at least about 2.5 times the upper limit of the reference range. In some embodiments, such subjects have Sertoli-Leydig cell tumors, hilus cell tumors, and lipoid cell (adrenal rest) tumors are the most common Sertoli-Leydig cell tumors reach palpable size at the time of clinical diagnosis, whereas hilar cell and lipoid cell tumors are difficult to detect by any means because of their small size.

In some embodiments, subjects amenable to treatment with a recombinant human MIS protein or functional derivatives or analogues thereof by the methods as disclosed herein are subjects with tumors of the adrenal glands (adenomas, carcinomas), which secrete elevated levels of androgens. In such embodiments, such subjects amenable to treatment by the methods as disclosed herein can be identified by having a DHEAS level of about or exceeding 7 µg/mL (18 µmol/L).

Other subjects that are amenable to the methods of treatment of excess androgen states as disclosed herein include, for example, classical and nonclassical (late-onset) CAH, cushing syndrome, where subjects with Cushing syndrome secrete elevated androgens, Hyperandrogenic, insulin resistance, and acanthosis *nigricans* (HAIR-AN) syndrome. In some embodiments, other subjects amenable to the methods of treatment of excess androgen states as disclosed herein include, for example, subjects with mild androgenic disorders, such as, but not limited to, Ovulatory PCOS (Ovulatory hyperandrogenic subjects with polycystic ovary at ultrasonography), Idiopathic hyperandrogenism (an Ovulatory hyperandrogenic subject but with normal ovaries at ultrasonography); Idiopathic hirsutism (subjects with an androgenic phenotype with normal androgens).

Reference testosterone levels and DHEAS levels are commonly known by persons of ordinary skill in the art, and are disclosed in Guay et al, International Journal of Impotence Research (2004) 16, 112-120, which is incorporated herein in its entirety by reference. Briefly, normal androgen levels in women between the ages of 20 and 49 years range between; DHEAS; about 195.6-140.4 ug/dl; serum testosterone about 51.5-33.7 ng/dl and free testosterone 1.51-1.03 pg/ml. Accordingly, subjects amenable to the treatment of the pyrazoloanthrone or functional derivatives or analogues thereof by the methods as disclosed herein have at least about a 20%, or at least about a 30% or at least about a 40% or at least about a 50%, or at least about a 60% or at least about a 70%, or at least about a 80%, or at least about a 90%, or at least about a 100% or greater increase in DHEAS or serum testosterone, or free testosterone levels as compared to the highest range value of the normal value for DHEAS (195.6 µg/dl), serum testosterone (51.5 ng/dl), free testostereone (1.51 pg/ml). In some embodiments, subjects amenable to the treatment of the pyrazoloanthrone or functional derivatives or analogues thereof by the methods as disclosed herein have at least about a 2-fold, or at least about a 3-fold, or at least about a 4-fold, or at least about a 5-fold, or at least about a 10-fold or greater increase in DHEAS or serum testosterone, or free testosterone levels as compared to the highest range value of the normal value for DHEAS (195.6 µg/dl), serum testosterone (51.5 ng/dl), free testostereone (1.51 pg/ml).

DHEAS can be measured by one of ordinary skill in the art using a kit from by Diagnostic Products Corporation of Los Angeles, Calif., USA. Cross-reactivity has previously been determined as being 100% for DHEAS and 0.121% with androstenedione, 15% with 9-hydroxyandrostenedione, 0.046% with estrone 3 sulfate, 0.55% with androsterone sulfate, 0.5% with DHEA and negligible for all other steroids tested. Free Testosterone can be measured by one of ordinary skill in the art using was measured using the Coat a Count Kits of Diagnostic Products Corporation, Los Angeles, Calif., USA. Cross-reactivity has previously been determined to be 0.41% for dihydrotestosterone, 0.01% for androstenedione, 0.10% for methyl testosterone and0.01% for all other steroids tested. Total serum testosterone levels can be measured by one of ordinary skill in the art using with the Immunochem serum testosterone kit of ICN Biomedicals Inc., Diagnostic Division of Costa Mesa, Calif., USA.

The assays to determine serum pregnenolone and 17-hydroxypregnenolone can be performed by one of ordinary skill in the art from the kit from Quest Laboratory in Tarzana, Calif., USA. Free Androgen Index (FAI) can be calculated using the following formula: (Total testosterone ng/dl×0.0347)/(SHBG nmol/l)×100=FAI.

Administration of Pharmaceutical Compositions

A recombinant human MIS protein or derivative or functional fragment thereof can be administered by any route known in the art or described herein, for example, oral, parenteral (e.g., intravenously or intramuscularly), intraperitoneal, rectal, cutaneous, nasal, vaginal, inhalant, skin (patch), or ocular. The recombinant human MIS protein or derivative or functional fragment protein may be administered in any dose or dosing regimen.

With respect to the therapeutic methods of the invention, it is not intended that the administration of a recombinant human MIS protein or polynucleotide encoding such a recombinant human MIS protein or functional fragment thereof be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat an autoimmune disease or immune-related disorder as disclosed herein. An effective amount, e.g., a therapeutically effective dose of a recombinant human MIS protein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising a recombinant human MIS protein agent can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, an effective amounts of a recombinant human MIS protein or derivative or functional fragment thereof can provided at a dose of 0.0001, 0.01, 0.01, 0.1, 1, 5, 10, 25, 50, 100, 500, or 1,000 mg/kg. Effective doses may be extrapolated from dose-response curves derived from in vitro or animal model test bioassays or systems. In some embodiments, doses of a recombinant human MIS protein are about 1 pg/kg to 10 mg/kg (body weight of patient) although lower and higher doses can also be administered.

In some embodiments, reference ranges for doses of recombinant human MIS are estimated from reference groups in the United States, and are disclosed in Antimullerian Hormone (AMH), Serum from Mayo Medical Laboratories. Retrieved April 2012. In some embodiments, female subjects can be administered the following doses of recombinant human MIS: females younger than 24 months: Less than 5 ng/mL; females 24 months to 12 years: Less than 10 ng/mL; females 13-45 years: 1 to 10 ng/mL; females older than 45 years: Less than 1 ng/mL. In some embodiments, male subjects can be administered the following doses of recombinant human MIS; males younger than 24 months: 15 to 500 ng/m; males between 24 months to 12 years: 7 to 240 ng/mL; males older than 12 years: 0.7 to 20 ng/mL. It is noted that MIS measurements may be less accurate if the person being measured is vitamin D deficient.

Additionally, as additivity, synergy, or competition has been demonstrated with MIS and rapamycin, AzadC, doxorubicin, cisplatin, and paclitaxel, recombinant human MIS as disclosed herein can be administered in combination with selective targeted therapies, for example to achieve greater activity against ovarian cancer than the use of recombinant human MIS or the chemotherapeutic agent used alone.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of a recombinant human MIS protein or functional derivatives or functional fragments thereof as disclosed herein, and the condition of the patient, the autoimmune disease to be treated, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising a recombinant human MIS protein or functional derivatives or functional fragments thereof are optionally tested in one or more appropriate in vitro and/or in vivo animal models of disease, such a an Mullerian duct regression bioassay as disclosed herein in the Examples, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of a recombinant human MIS protein or functional derivatives or functional fragments thereof at various concentrations, e.g., as applied to the mass and overall health of the patient. Administration can be accomplished via single or divided doses.

In determining the effective amount of a recombinant human MIS protein or functional derivatives or functional fragments thereof to be administered in the treatment or prophylaxis of a disease, the physician evaluates circulating plasma levels, formulation toxicities, and progression of the disease. The selected dosage level will also depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, a recombinant human MIS protein as disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising a recombinant human MIS protein or functional fragment or variant thereof as disclosed herein can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Furthermore, actual dosage levels of a recombinant human MIS protein in a pharmaceutical composition can be varied so as to obtain an amount of the active ingredient which is effective to achieve the desired therapeutic response for a particular subject, composition, and mode of administration, without being toxic to the subject. A pharmaceutical composition comprising a recombinant human MIS protein or functional fragment or variant thereof as disclosed herein can be a "therapeutically effective amount" and/or a "prophylactically effective amount". In general, a suitable daily dose of a composition comprising a recombinant human MIS protein or functional fragment or variant thereof as disclosed herein will be that amount of the a recombinant human MIS protein which is the lowest dose effective to produce a therapeutic effect, such as a reduction of a symptom of a proliferative disorder or cancer as disclosed herein. Such an effective dose will generally depend upon the factors described above.

If desired, the effective daily dose of a composition comprising a recombinant human MIS protein or functional fragment or variant thereof can be administered as two, three, four, five, six or more sub-doses administered separately at appropriate intervals throughout the day, optionally, in unit dosage forms.

The dosage level administered to a subject can be constant over a desired period of time, for example, at least 1 week, at least 2 weeks, at least 3 weeks, at least 1 month, at least 2 months, at least 3 months, at least 6 months, at least 1 year, or at least 5 years. Alternatively, the dosage level administered to a subject can vary depending on the progression of the condition being treated.

It is to be noted that dosage values may vary with the type and severity of the cancer to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. An appropriate experimental model which can be used includes determining a the dose can be use of the mullerian duct regression bioassay as disclosed herein in the examples, or a in vivo cancer model which is commonly known by ordinary skill in the art. In vivo cancer models are discussed in Frese et al., "Maximizing mouse cancer models" Nat Rev Cancer. 2007 September; 7(9):645-58 and Santos et al., Genetically modified mouse models in cancer studies. Clin Transl Oncol. 2008 December; 10(12):794-803, and "Cancer stem cells in mouse models of cancer", 6th Annual MDI Stem Cell Symposium, MDI Biological Lab, Salisbury Cove, Me., Aug. 10-11, 2007" which are incorporated herein in their entirety by reference.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of a recombinant human MIS protein can be assessed in a mouse model of cancer, or using the Mullerian Duct Regression bioassay as disclosed herein in the Examples and FIG. 4.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals exemplified herein, which treatment has a length proportional to the length of the disease process and drug effectiveness. The doses may be single doses or multiple doses over a period of several days, but single doses are preferred.

In some embodiments, a recombinant human MIS protein (e.g., proteins or nucleic acids encoding a recombinant human MIS protein or fragments thereof) can be administered to humans and other animals for therapy by any suitable route of administration, including orally, nasally, as by, for example, a spray, rectally, intravaginally, parenterally, intracisternally and topically, as by powders, ointments or drops, including buccally and sublingually.

After formulation with an appropriate pharmaceutically acceptable carrier in a desired dosage, a pharmaceutical composition comprising a recombinant human MIS protein or functional fragment or variant thereof as disclosed herein can be administered to a subject. A pharmaceutical a composition comprising a recombinant human MIS protein or functional fragment or variant thereof can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

In a specific embodiment, it may be desirable to administer the pharmaceutical composition comprising a recombinant human MIS protein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, a recombinant human MIS protein as disclosed herein can be applied to the muscle using topical creams, patches, intramuscular injections and the like.

In some embodiments, a recombinant human MIS protein can be administered to a subject orally (e.g., in capsules, suspensions or tablets) or by parenteral administration. Conventional methods for oral administration include administering a recombinant human MIS protein in any one of the following; tablets, suspensions, solutions, emulsions, capsules, powders, syrups and the like are usable. Known techniques that deliver a recombinant human MIS protein orally or intravenously and retain the biological activity are preferred. Parenteral administration can include, for example, intramuscular, intravenous, intraarticular, intraarterial, intrathecal, subcutaneous, or intraperitoneal administration. A recombinant human MIS protein can also be administered orally, transdermally, topically, by inhalation (e.g., intrabronchial, intranasal, oral inhalation or intranasal drops) or rectally. Administration can be local or systemic as indicated. Agents, e.g., nucleic acid agents which encode a recombinant human MIS protein or functional fragment thereof can also be delivered using a vector, e.g., a viral vector by methods which are well known to those skilled in the art.

When administering a composition comprising a recombinant human MIS protein or functional fragment or variant thereof as disclosed herein parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the a recombinant human MIS protein or functional fragment or variant thereof as disclosed herein and the particular therapeutic or prophylactic effect to be achieved, and (b) the limitations inherent in the art of compounding a recombinant human MIS protein an active agent for the treatment of sensitivity in individuals.

The pharmaceutically acceptable compositions comprising a recombinant human MIS protein or functional fragment or variant thereof as disclosed herein can be suspended in aqueous vehicles and introduced through conventional hypodermic needles or using infusion pumps.

Pharmaceutical Compositions

In some embodiments, a composition comprising a recombinant human MIS protein or functional fragment or variant thereof as disclosed herein can be formulated in any suitable means, e.g., as a sterile injectable solution, e.g., which can be prepared by incorporating the recombinant human MIS protein in the required amount of the appropriate solvent with various of the other ingredients, as desired.

A pharmacological formulation of a composition comprising a recombinant human MIS protein or functional fragment or variant thereof as disclosed herein can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those presented in U.S. Pat. Nos. 5,225,182; 5,169,383; 5,167,616; 4,959,217; 4,925,678; 4,487,603; 4,486,194; 4,447,233; 4,447, 224; 4,439,196 and 4,475,196. Other such implants, delivery systems, and modules are well known to those skilled in the art.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, e.g., parabens, chlorobutanol, phenol and sorbic acid. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

In another embodiment, a composition comprising a recombinant human MIS protein or functional fragment or variant thereof as disclosed herein can comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing a recombinant human MIS protein or functional fragment or variant thereof, such variables as the efficiency of active compound encapsulation, labiality of the active compound, homogeneity and size of the resulting population of vesicles, active compound-to-lipid ratio, permeability, instability of the preparation, and pharmaceutical acceptability of the formulation should be considered.

In another embodiment, a recombinant human MIS protein can be delivered in a vesicle, in particular a liposome (see Langer (1990) Science 249:1527-1533). In yet another embodiment, a recombinant human MIS protein can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a recombinant human MIS protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Prior to introduction, a composition comprising a recombinant human MIS protein or functional fragment or variant thereof as disclosed herein can be sterilized, by any of the numerous available techniques of the art, such as with gamma radiation or electron beam sterilization.

In another embodiment of the invention, a composition comprising a recombinant human MIS protein or functional fragment or variant thereof as disclosed herein, can be administered and/or formulated in conjunction (e.g., in combination) with any other therapeutic agent. For purpose of administration, a recombinant human MIS protein or functional fragment or variant thereof as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in Remington's Pharmaceutical Sciences, Gennaro, Ed., Mack Publishing Co., Easton, Pa. 1990.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more resolvins and/or protectins or their analogues of the invention.

Formulations of a composition comprising a recombinant human MIS protein or functional fragment or variant thereof as disclosed herein can be prepared by a number or means known to persons skilled in the art. In some embodiments the formulations can be prepared for administration as an aerosol formulation, e.g., by combining (i) a recombinant human MIS protein or functional fragment or variant thereof as disclosed herein in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

In certain embodiments, a composition comprising a recombinant human MIS protein as disclosed herein can be administered to a subject as a pharmaceutical composition with a pharmaceutically acceptable carrier. In certain embodiments, these pharmaceutical compositions optionally further comprise one or more additional therapeutic agents. In certain embodiments, the additional therapeutic agent or agents are autoimmune disease or drugs, such as immune suppressants and the like. In some embodiments, an additional therapeutic agent is a cortiosteriod. In some embodiments, an additional therapeutic agent is selected from the group consisting of Prednisone, methylprednisolone, Kenalog, Medrol Oral, Medrol (Pak) Oral, Depo-Medrol Inj, prednisolone Oral, Solu-Medrol Inj, hydrocortisone Oral, Cortef Oral, Solu-Medrol IV, cortisone Oral, Celestone Soluspan Inj, Orapred ODT Oral, Orapred Oral, Prelone Oral, methylprednisolone acetate Inj, Prednisone Intensol Oral, betamethasone acet & sod phos Inj, Veripred, Celestone Oral, methylprednisolone sodium succ IV, methylprednisolone sodium succ Inj, Millipred Oral, Solu-Medrol (PF) Inj, Solu-Cortef Inj, Aristospan Intra-Articular Inj, hydrocortisone sod succinate Inj, prednisolone sodium phosphate Oral, methylprednisolone sod suc(PF) IV, Solu-Medrol (PF) IV, triamcinolone hexacetonide Inj, A-Hydrocort Inj, A-Methapred Inj, Millipred DP Oral, Flo-Pred Oral, Aristospan Intralesional Inj, betamethasone Oral, methylprednisolone sod suc(PF) Inj, hydrocortisone sod succ (PF) Inj, Solu-Cortef (PF) Inj, prednisolone acetate Oral, dexamethasone in 0.9% NaCl IV, Rayos, levothyroxine. Of course, such therapeutic agents are which are known to those of ordinary skill in the art can readily be substituted as this list should not be considered exhaustive or limiting.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations of the invention suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or *acacia*; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, a composition comprising a recombinant human MIS protein or functional fragment or variant thereof as disclosed herein can be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a recombinant human MIS protein of this invention, e.g., for muscular administration include powders, sprays, ointments, pastes, creams, lotions, gels, solutions, patches and inhalants. A recombinant human MIS protein or functional fragment or variant thereof as disclosed herein may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a recombinant human MIS protein of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a recombinant human MIS protein or functional fragment or variant thereof can be isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

In some embodiments, the composition comprises at least one a recombinant human MIS protein in combination with a pharmaceutically acceptable carrier. Some examples of materials which can serve as pharmaceutically acceptable carriers include, without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, a composition comprising a recombinant human MIS protein or functional fragment or variant thereof as disclosed herein can contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of patients without undue toxicity, irritation, allergic response, and the like, commensurate with a reasonable benefit/risk ratio, and effective for their intended use. These compounds include the zwitterionic forms, where possible, of r compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds or agents that are rapidly transformed in vivo to yield the active recombinant human MIS protein, e.g., a biologically active or functional active MIS protein or nucleic acid (e.g., mRNA, DNA, MOD-RNA) which encodes a functionally active MIS protein. In some embodiments, a recombinant human MIS protein prodrug can be activated by hydrolysis in blood, e.g., via cleavage of a leader sequence, and or cleavage at the primary cleavage site to result in the N-terminal and C-terminal domains for production of a bioactive MIS protein, similar to how insulin is activated from its proprotein into an active insulin protein. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a recombinant human MIS protein, to mask side effects or toxicity, or to alter other characteristics or properties of the recombinant human MIS protein.

By virtue of knowledge of pharmacodynamic processes and drug metabolism or post-translational protein processing of MIS in vivo, once a pharmaceutically active compound is identified, those of skill in the pharmaceutical art generally can design a recombinant human MIS protein prodrug which can be activated in vivo to increase levels of a bioactive MIS protein in the subject (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

As discussed herein, in some embodiments a composition comprising a recombinant human MIS protein or functional fragment or variant thereof as disclosed herein can be conjugated or covalently attached to a targeting agent to increase their tissue specificity and targeting to a cell, for example a muscle cells. Targeting agents can include, for example without limitation, antibodies, cytokines and receptor ligands, as discussed in the section entitled "targeting." In some embodiments, the targeting agent is overexpressed on the cells to be targeted, for example the muscle cells as compared to non-muscle cells.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Gene Therapy

In some embodiments, a nucleic acid encoding a recombinant human MIS protein or functional fragment thereof as disclosed herein, can be suitably administered as a vector, e.g., a viral vector.

In some embodiments, a nucleic acid encoding a recombinant human MIS protein can be effectively used in treatment by gene therapy. See, generally, for example, U.S. Pat. No. 5,399,346, which is incorporated herein by reference. The general principle is to introduce the polynucleotide into a target cell in a patient, and where it is transcribed into the protein.

Entry into the cell can be facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

Expression vectors compatible with eukaryotic cells, preferably those compatible with vertebrate cells, can be used to produce recombinant constructs for the expression of a recombinant human MIS protein or a functional derivative or functional variant or functional fragment thereof as disclosed herein. Eukaryotic cell expression vectors are well known in the art and are available from several commercial sources. Typically, such vectors are provided containing convenient restriction sites for insertion of the desired DNA segment. These vectors can be viral vectors such as adenovirus, adeno-associated virus, pox virus such as an orthopox (vaccinia and attenuated vaccinia), avipox, lentivirus, murine moloney leukemia virus, etc.

Alternatively, in some embodiments, a plasmid expression vector can be used. Plasmid expression vectors include, but are not limited to, pcDNA3.1, pET vectors (Novagen®), pGEX vectors (GE Life Sciences), and pMAL vectors (New England labs. Inc.) for protein expression in E. coli host cell such as BL21, BL21(DE3) and AD494(DE3)pLysS, Rosetta (DE3), and Origami (DE3) ((Novagen®); the strong CMV promoter-based pcDNA3.1 (Invitrogen™ Inc.) and pClneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech®), pAd/CMV/V5-DEST, pAd-DEST vector (Invitrogen™ Inc.) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS and pAAV-IRES-hrGFP for adeno-associated virus-mediated gene transfer and expression in mammalian cells; BACpak6 baculovirus (Clontech®) and pFastBac™ HT (Invitrogen™ Inc.) for the expression in Spodopera frugiperda 9 (Sf9) and Sfl 1 insect cell lines; pMT/BiP/V5-His (Invitrogen™ Inc.) for the expression in Drosophila Schneider S2 cells; Pichia expression vectors pPICZα, pPICZ, pFLDα and pFLD (Invitrogen™ Inc.) for expression in Pichia pastoris and vectors pMETα and pMET for expression in P. methanolica; pYES2/GS and pYD1 (Invitrogen™ Inc.) vectors for expression in yeast Saccharomyces cerevisiae. Recent advances in the large scale expression heterologous proteins in Chlamydomonas reinhardtii are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

Viral vector systems which can be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. In a preferred embodiment, the vector is an adenovirus. Replication-defective viruses can also be advantageous.

The vector may or may not be incorporated into the cells genome. The constructs may include viral sequences for transfection, if desired. Alternatively, the construct may be incorporated into vectors capable of episomal replication, e.g., EPV and EBV vectors.

Constructs for the expression of a nucleic acid encoding a recombinant human MIS protein as disclosed herein., e.g., DNA, MOD-RNA or RNAa, can generally be operatively linked to regulatory elements, e.g., promoters, enhancers, etc., to ensure the expression of the construct in target cells. Other specifics for vectors and constructs are described in further detail below.

Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Included in the term "regulatory elements" are nucleic acid sequences such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc. Regulatory sequences useful in the methods as disclosed herein are promoter elements which are sufficient to render promoter-dependent gene expression controllable for cell type-specific, tissue-specific or inducible by external signals or agents (e.g. enhancers or repressors); such elements may be located in the 5' or 3' regions of the native gene, or within an intron.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue, such as cells of ovarian origin.

The term "constitutively active promoter" refers to a promoter of a gene which is expressed at all times within a given cell. Exemplary promoters for use in mammalian cells include cytomegalovirus (CMV), and for use in prokaryotic cells include the bacteriophage T7 and T3 promoters, and the like. The term "inducible promoter" refers to a promoter of a gene which can be expressed in response to a given signal, for example addition or reduction of an agent. Non-limiting examples of an inducible promoter are "tet-on" and "tet-off" promoters, or promoters that are regulated in a specific tissue type.

In a specific embodiment, viral vectors that contain nucleic acid sequences e.g., DNA, MOD-RNA or RNAa encoding a recombinant human MIS protein or functional fragment thereof as disclosed herein can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a recombinant human MIS protein are cloned into one or more vectors, which facilitate delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

The production of a recombinant retroviral vector carrying a gene of interest is typically achieved in two stages. First, sequence encoding a recombinant human MIS protein or a functional derivative or functional variant or functional fragment thereof, alone or fused to –Fc can be inserted into a retroviral vector which contains the sequences necessary for the efficient expression of the metabolic regulators (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (–PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant retroviral vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Another preferred viral vector is a pox virus such as a vaccinia virus, for example an attenuated vaccinia such as Modified Virus Ankara (MVA) or NYVAC, an avipox such as fowl pox or canary pox. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In another embodiment, lentiviral vectors are used, such as the HIV based vectors described in U.S. Pat. Nos. 6,143,520; 5,665,557; and 5,981,276, which are herein incorporated by reference. In some embodiments, a viral vector such as an Adeno-associated virus (AAV) vector is used. Exemplary AAV vectors are disclosed in Walsh et al., Proc. Soc. Exp. Biol. Med. 204:289-300 (1993); U.S. Pat. No. 5,436,146 which is incorporated herein by reference; Gao et al., Gene Therapy 2005, 5, 285-297; Vandenberghe et al., Gene Therapy 2009, 16, 311-319; Gao et al., PNAS 2002, 99, 11854-11859; Gao et al., PNAS 2003, 100, 6081-6086; Gao et al., J. of Virology 2004, 78, 6381-6388; Molecular Cloning: A Laboratory Manual ($4^{th}$ edition) ed. by M. Green and J. Sambrook. In some embodiments, the AAV vector is an AAV1, AAV2, AAV4, AAV5, AAV6, AAV7, AAV8, AAV9, AAVrh.10, AAV2.5. It should be noted that the selection of a particular type of AAV vectors can depend on the target tissue.

In some embodiments, when a recombinant human MIS protein encoded by a viral vector is expressed endogenously in a subject, the expression level of the recombinant human MIS protein disclosed herein can be constant over a desired period of time, for example, at least 1 week, at least 2 weeks, at least 3 weeks, at least 1 month, at least 2 months, at least 3 months, at least 6 months, at least 1 year, or at least 5 years. In some embodiments, the expression of the recombination human MIS protein disclosed herein can be sustained at or above a therapeutically effective dosage level over a desired period of time.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

U.S. Pat. No. 5,676,954 (which is herein incorporated by reference) reports on the injection of genetic material, complexed with cationic liposome carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals. Such cationic lipid complexes or nanoparticles can also be used to deliver protein.

A gene or nucleic acid sequence can be introduced into a target cell by any suitable method. For example, a recombinant human MIS protein construct can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding a recombinant human MIS protein can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a gene or nucleic acid sequence encoding a recombinant human MIS protein can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999)).

Methods known in the art for the therapeutic delivery of agents such as proteins and/or nucleic acids can be used for the delivery of a polypeptide or nucleic acid encoding a recombinant human MIS protein to a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to directly administer therapeutic polypeptides such as a recombinant human MIS protein and/or a nucleic acid encoding a recombinant human MIS protein as disclosed herein, e.g., encapsulation in liposomes, microparticles, microcapsules, recombinant cells capable of expressing the compound, and receptor-mediated endocytosis (see, e.g., Wu and Wu, 1987, J. Biol. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked recombinant human MIS protein encoding nucleic acid segment into the selected expression/delivery vector, many equivalent vectors for the practice of the methods described herein can be generated.

It will be appreciated by those of skill that cloned genes readily can be manipulated to alter the amino acid sequence of a protein. The cloned gene for recombinant human MIS protein can be manipulated by a variety of well-known techniques for in vitro mutagenesis, among others, to produce variants of the naturally occurring human protein, herein referred to as muteins or variants or mutants of a recombinant human MIS protein, which may be used in accordance with the methods and compositions described herein.

The variation in primary structure of muteins of a recombinant human MIS protein useful in the invention, for instance, may include deletions, additions and substitutions. The substitutions may be conservative or non-conservative. The differences between the natural protein and the mutein generally conserve desired properties, mitigate or eliminate undesired properties and add desired or new properties.

Remington's Pharmaceutical sciences Ed. Germany, Merk Publishing, Easton, Pa., 1 995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

Kits

The invention also provides kits or pharmaceutical packages that comprise a recombinant human MIS protein or functional variant or functional fragment or fusion protein thereof for use in the prevention and/or treatment of a proliferative disease or disorder, e.g., cancer or disease of excess androgen as disclosed herein. The kit can comprise a recombinant human MIS protein composition in the form of, for example, tablets, capsules, or lyophilized powders, and can optionally include instructions for using a recombinant human MIS protein for the treatment of cancer or disease associated with androgen dependency. A composition comprising a recombinant human MIS protein or functional variant or functional fragment or fusion protein thereof can be provided in the kits or packages in a bottle or another appropriate form (e.g., a blister pack). Optionally, the kits or pharmaceutical packages can also include other pharmaceutically active agents (see, e.g., the agents listed above, such as other agents used for treatment of autoimmune diseases and disorders), and/or materials used in administration of the drug(s), such as diluents, needles, syringes, applicators, and the like.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

Some embodiments of the invention are listed in the following paragraphs:

1. A recombinant Mullerian Inhibiting Substance (MIS) protein comprising a modification of at least one amino acid between residues 448-452 of SEQ ID NO: 1 to increase cleavage as compared to in the absence of a modification.
2. The recombinant MIS protein of paragraph 1, further comprising a non-MIS leader sequence or a functional fragment thereof in place of the MIS leader sequence of amino acids 1-25 of SEQ ID NO: 1, andwherein the recombinant MIS protein has increased cleavage and increased yield of production in vitro as compared to wild-type MIS protein corresponding to amino acid residues of SEQ ID NO: 1.
3. The recombinant MIS protein of paragraph 1 or 2, wherein the recombinant MIS protein further comprises a Tag protein.
4. The recombinant MIS protein of paragraph 2, wherein the non-MIS leader sequence is an albumin leader sequence or a functional fragment thereof.
5. The recombinant MIS protein of paragraph 4, wherein the albumin leader sequence is a human serum albumin (HSA) leader sequence or a fragment thereof.
6. The recombinant MIS protein of paragraph 5, wherein the HSA leader sequence comprises the amino acid sequence of SEQ ID NO: 6 or a variant that is at least 80% homologous thereto.
7. The recombinant MIS protein of paragraph 5, wherein a fragment of the HSA leader sequence comprises at least 10 amino acids of SEQ ID NO: 6 or a variant that is at least 80% homologous thereto.
8. The recombinant MIS protein of paragraph 5, wherein the HSA leader sequence comprises at least 15 amino acids of SEQ ID NO: 6, or a variant that is at least 80% homologous thereto.
9. The recombinant MIS protein of paragraph 5, wherein the HSA leader sequence comprises at least 11 amino acids of SEQ ID NO: 6, or a variant that is at least 80% homologous thereto.
10. The recombinant MIS protein of paragraph 5, wherein a fragment of the HSA leader sequence is selected from the group consisting of: MKWVTFISLLFLFSSAYS (SEQ ID NO: 13); MKWVTFISLLFLFSSAYSRGVFRR (SEQ ID NO: 6); MKWVSFISLLFLFSSAYS (SEQ ID NO:14).
11. The recombinant MIS protein of paragraph 2, wherein the non-MIS leader sequence is selected from a group consisting of: immunoglobulin signal peptide fused to a tissue-type plasminogen activator propeptide (IgSP-tPA), murine immunoglobulin signal peptide (IgSP), a MPIF-1 signal sequence (MKVSVAALSCLMLVTALGSQA (SEQ ID NO: 15); a stanniocalcin signal sequence (MLQNSAVLLLLVISASA (SEQ ID NO:16)); an invertase signal sequence (MLLQAFLFLLAGFAAKISA (SEQ ID NO:17)); a yeast mating factor alpha signal sequence (*K. lactis* killer toxin leader sequence); a hybrid signal sequence (MKWVSFISLLFLFSSAYSRSLEKR, (SEQ ID NO:18)); a HSA/MFα-1 hybrid signal sequence (MKWVSFISLLFLFSSAYSRSLDKR (SEQ ID NO:19)); a *K. lactis* killer/MFα-1 fusion leader sequence (MNIFYIFLFLLSFVQGSLDKR (SEQ ID NO:20)); an immunoglobulin Ig signal sequence (MGWSCIILFLVATATGVHS (SEQ ID NO:21)); a Fibulin B precursor signal sequence (MERAAPSRRVPLPLLLLGGLALLAAGVDA (SEQ ID NO:22)); a clusterin precursor signal sequence (MMKTLLLFVGLLLTWESGQVLG (SEQ ID NO: 23)); and the insulin-like growth factor-binding protein 4 signal sequence (MLPLCLVAALLLAAGPGPSLG (SEQ ID NO:24)) or a functional fragment thereof.
12. The recombinant MIS protein of paragraph 1, comprising a modification of amino acid 450 of SEQ ID NO: 1 from Q to R to increase cleavage as compared to in the absence of such a modification.
13. The recombinant MIS protein of paragraph 1, further comprising a modification of amino acid 452 of SEQ ID NO: 1 from S to R to increase cleavage as compared to in the absence of such a modification.
14. The recombinant MIS protein of paragraph 3, wherein the tag is a FLAG tag.
15. The recombinant MIS protein of paragraph 14, wherein the FLAG tag comprises amino acid sequence DYKDDDDK (SEQ ID NO: 8), or a functional derivative or variant thereof.
16. The recombinant MIS protein of paragraph 14, wherein the FLAG tag is located after amino acid residue 452 of SEQ ID NO: 1 and before amino acid residue 453 of SEQ ID NO: 1.

17. The recombinant MIS protein of paragraph 14, wherein the FLAG tag is located between amino acid residue 452 and 453 of SEQ ID NO: 1.
18. The recombinant MIS protein of paragraph 1, which comprises the amino acid sequence of SEQ ID NO: 2 or a functional fragment thereof.
19. The recombinant MIS protein of paragraph 1, which comprises the amino acid sequence of SEQ ID NO: 3 or a functional fragment thereof.
20. The recombinant MIS protein of paragraph 18, which is encoded by nucleic acid sequence of SEQ ID NO: 4.
21. The recombinant MIS protein of paragraph 19, which is encoded by nucleic acid sequence of SEQ ID NO: 5.
22. A pharmaceutical composition comprising the recombinant MIS protein of any of paragraphs 1 to 21 and a pharmaceutically acceptable carrier.
23. A polynucleotide encoding the recombinant MIS protein of any of paragraphs 1 to 21.
24. The polynucleotide of paragraph 23, wherein the nucleotide corresponds to SEQ ID NO: 4 or a nucleotide which has at least 95% sequence identity to the nucleic acid sequence of SEQ ID NO: 4.
25. The polynucleotide of paragraph 23, wherein the nucleotide corresponds to SEQ ID NO: 5 or a nucleotide which has at least 95% sequence identity to the nucleic acid sequence of SEQ ID NO: 5.
26. A vector comprising the polynucleotide of paragraphs 23-25.
27. The vector of paragraph 26, wherein the vector is a viral vector or an expression vector.
28. The vector of paragraph 27, wherein the expression vector is pcDNA 3.1 or cDNA or genome vector for bacteria (e.g., *e coli*) or bacteriophage.
29. The vector of paragraph 27, wherein the viral vector is selected from the group consisting of an adenoviral vector, a poxvirus vector and a lentiviral vector.
30. The vector of paragraph 27, wherein the viral vector is an adeno-associated vector (AAV).
31. The vector of paragraph 30, wherein the AAV is AAV9.
32. The vector of any of paragraphs 26 to 31, wherein the nucleic acid sequence encodes a recombinant MIS protein or fragment thereof which has at least 95% sequence identity to the nucleic acid sequence of SEQ ID NO: 4 or SEQ ID NO: 5, wherein the nucleic acid sequence is operatively linked to tissue- or cell-type specific promoter.
33. A human MIS protein produced by post-translational processing of the recombinant human MIS protein of paragraph 1.
34. A host cell comprising the vector of any of the paragraphs 26 to 32.
35. A pharmaceutical composition comprising the vector of any of the paragraphs 26 to 32 and a pharmaceutically acceptable carrier.
36. A purified preparation of human MIS protein produced from the recombinant human MIS protein of any of paragraphs 1 to 21.
37. A method for treating a subject with cancer, comprising administering a composition comprising a recombinant MIS protein, wherein the recombinant MIS protein comprises a modification of at least one amino acid between residues 448-452 of SEQ ID NO: 1 to increase cleavage as compared to in the absence of a modification.
38. The method of paragraph 37, wherein the recombinant MIS protein has increased cleavage and increased yield of production in vitro as compared to wild-type MIS protein corresponding to amino acid residues of SEQ ID NO: 1.
39. The method of paragraph 37, wherein the recombinant MIS protein is produced from a pre-proprotein comprising a non-MIS leader sequence or a functional fragment thereof in place of the MIS leader sequence of amino acids 1-25 of SEQ ID NO: 1.
40. The method of paragraph 37, wherein the recombinant MIS protein further comprises a Tag protein.
41. The method of paragraph 39, wherein the non-MIS leader sequence is an albumin leader sequence or a functional fragment thereof.
42. The method of paragraph 41, wherein the albumin leader sequence is a human serum albumin (HSA) leader sequence or a fragment thereof.
43. The method of paragraph 37, wherein the recombinant MIS protein comprises a modification of amino acid 450 of SEQ ID NO: 1 from Q to R to increase cleavage as compared to in the absence of such a modification.
44. The method of paragraph 40, wherein the tag is a FLAG tag comprising amino acid sequence of SEQ ID NO: 8 or a functional fragment thereof.
45. The method of paragraph 37, wherein the recombinant MIS protein comprises the amino acid residues 25-559 of SEQ ID NO: 2 or a functional fragment thereof.
46. The method of paragraph 37, wherein the recombinant MIS protein comprises the amino acid residues 25-567 of SEQ ID NO: 3 or a functional fragment thereof.
47. The method of paragraph 37, wherein the cancer is a MIS Responsive II cancer.
48. The method of paragraph 37, wherein the cancer is ovarian cancer.
49. The method of paragraph 37, wherein the cancer is a chemotherapeutic-resistant or multi-drug resistant cancer.
50. The method of paragraph 37, wherein the administration of the recombinant MIS protein is prior to, during, or after administration of an additional agent or cancer therapy.
51. The method of paragraph 37, wherein the cancer expresses Mullerian Inhibiting Substance Receptor II (MISRII).
52. The method of paragraph 51, wherein the expression of Mullerian Inhibiting Substance (MIS) receptor is measured in a biological sample obtained from the subject.
53. The method of paragraph 52, wherein the biological sample is a cancer or tumor tissue sample or a cancer cell or tumor cell.
54. The method of paragraph 52, wherein the biological sample is a biopsy tissue sample.
55. The method of paragraph 37, wherein the cancer is an ovarian cancer cell, vulvar epidermal carcinoma cell, cervical carcinoma cell, endometrial edenocarinaoma cell and ovarian adenocarcinoma cell.
56. The method of paragraph 37, wherein the cancer is selected from the group consisting of: breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, gum cancer, kidney cancer, liver cancer, nasopharynx cancer, ovarian cancer, prostate cancer, skin cancer, stomach cancer, testis cancer, tongue cancer, melanoma, ocular melanoma, or uterine cancer.

57. The method of paragraph 49, wherein the multi-drug resistant cancer is a paclitaxel- or Doxorubicin-resistant cancer.
58. The method of paragraph 37, wherein administering is intravenous, intradermal, intramuscular, intraarterial, intralesional, percutaneous, or subcutaneous, or by aerosol.
59. The method of paragraph 37, wherein administering is prophylactic administration.
60. The method of paragraph 37, wherein administering is therapeutic administration.
61. The method of paragraph 37, wherein the subject is a mammal.
62. The method of paragraph 61, wherein the mammal is a human.
63. The method of paragraph 37, wherein at least one additional agent is administered to the subject in combination with (e.g., before, during or after) administration of the recombinant human MIS.
64. The method of paragraph 63, wherein the additional agent is a therapeutic agent or chemotherapeutic agent.
65. The method of paragraph 64, wherein the chemotherapeutic agent is selected from the group consisting of: paclitaxel, cisplatin, doxorubicin, rapamycin, pyrazoloanthrone.
66. The method of paragraph 64, wherein the chemotherapeutic agent is a radiotherapeutic agent.
67. The method of paragraph 64, wherein the chemotherapeutic agent is a pyrazoloanthrone.
68. The method of paragraph 67, wherein the pyrazoloanthrone is antra(1,9-cd)pyrazol-6(2H)-one (SP600125) or a functional derivative or functional analogue thereof.
69. A method of decreasing the dose of a chemotherapeutic agent for the treatment of cancer, the method comprising administering to the subject a therapeutically effective amount of a recombinant MIS protein, wherein the recombinant MIS protein comprises a modification of amino acid 450 of SEQ ID NO: 1 from Q to R, and wherein the therapeutically effective dose of the chemotherapeutic agent in the presence of the recombinant MIS protein is lower as compared to the therapeutically effective dose of the chemotherapeutic agent alone.
70. The method of paragraph 69, wherein the recombinant MIS protein further comprises a Tag protein.
71. Use of recombinant MIS protein for the manufacture of a medicament for treating cancer, wherein the recombinant MIS protein comprises a modification of amino acid 450 of SEQ ID NO: 1 from Q to R, and wherein the cancer expresses a Mullerian Inhibiting Substance (MIS) receptor.
72. The use of paragraph 71, wherein the recombinant MIS protein further comprises a Tag protein.
73. The use of paragraph 71, wherein the Mullerian Inhibiting Substance (MIS) receptor is MIS type II receptor or a homologue or functional fragment thereof.
74. An article of manufacture comprising packaging material and a pharmaceutical composition comprising the recombinant MIS protein of any of paragraphs 1 to 21, wherein the packaging material comprises a label which indicates the pharmaceutical composition may be administered, for a sufficient term at an effective dose, for treating or reducing the risk of cancer which expresses a Mullerian Inhibiting Substance (MIS) receptor.
75. A method of treating a subject affected with cancer, the method comprising assessing the expression and/or activity of Mullerian Inhibiting Substance Receptor II (MISRII) in a biological sample obtained from the subject, wherein a clinician reviews the results and if the results indicate the presence of expression and/or activity of MISRII, the clinician directs the subject to be treated with pharmaceutical composition of paragraph 22 or 35.
76. The method of paragraph 75, wherein the biological sample is a tissue sample.
77. The method of paragraph 76, wherein the tissue sample is a cancer or tumor tissue sample or a cancer cell or tumor cell.
78. The method of paragraph 76, wherein the biological sample is a biopsy tissue sample.
79. The method of paragraph 75, wherein the cancer is an ovarian cancer cell, vulvar epidermal carcinoma cell, cervical carcinoma cell, endometrial edenocarinaoma cell and ovarian adenocarcinoma cell.
80. The method of paragraph 75, wherein the cancer is breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, gum cancer, kidney cancer, liver cancer, nasopharynx cancer, ovarian cancer, prostate cancer, skin cancer, stomach cancer, testis cancer, tongue cancer, melanoma, ocular melanoma or uterine cancer.
81. Use of a recombinant MIS protein to decrease the plasma serum levels of one or more androgens in a subject in need thereof, wherein the recombinant MIS protein comprises a modification of amino acid 450 of SEQ ID NO: 1 from Q to R.
82. The use of paragraph 81, wherein the recombinant MIS protein further comprises a Tag protein.
83. The use of paragraph 81, wherein one or more androgens is testosterone.
84. The use of paragraph 81, wherein the subject in need thereof has benign prostatic hypertrophy.
85. The use of paragraph 81, wherein the subject in need thereof has prostate cancer.
86. The use of paragraph 81, wherein the subject in need thereof has polycystic ovarian disease and/or precocious puberty.
87. The use of paragraph 81, wherein the subject in need thereof has a disease or disorder selected from the group consisting of: Benign Prostatic Hyperplasia (BPH), prostate carcinoma, testicular cancer, androgen dependent acne, male pattern baldness, precocious puberty, hyperandrogenism, hirsutism, virilization, Polycystic Ovary Syndrome (POCS), hyperandrogenism (HA) and insulin resistance (IR) and acanthosis *nigricans* (AN) (HIAR-AN) syndrome, ovarian hyperthecosis, follicular maturation arrest, atresia, anovulation, dysmenorrheal, dysfunctional uterine bleeding, infertility and androgen-producing tumors.
88. A method to treat a disease or disorder characterized by androgenic dependency, comprising administering to a subject an effective amount of the pharmaceutical composition of paragraph 22 or 35, wherein the pharmaceutical composition reduces the level of at least one androgen in the plasma serum of the subject and results in a decrease in at least one symptom of a disease or disorder characterized by androgenic dependency.

89. A method to decrease the plasma level of one or more androgens in a subject, the method comprising administering an effective amount of a recombinant MIS protein, wherein the recombinant MIS protein comprises a modification of amino acid 450 of SEQ ID NO: 1 from Q to R, and wherein the recombinant MIS protein decreases the plasma serum levels of one or more androgens in the subject.

90. The method of paragraph 89, wherein the recombinant MIS protein further comprises a Tag protein.

91. The method of paragraph 89, wherein the subject has a disease or disorder characterized by androgenic dependency.

92. The method of any of paragraphs 89 to 91, wherein the disease or disorder is selected from the group consisting of: Benign Prostatic Hyperplasia (BPH), prostate carcinoma, testicular cancer, androgen dependent acne, male pattern baldness, precocious puberty, hyperandrogenism, hirsutism, virilization, Polycystic Ovary Syndrome (POCS), hyperandrogenism (HA) and insulin resistance (IR) and acanthosis *nigricans* (AN) (HIAR-AN) syndrome, ovarian hyperthecosis, follicular maturation arrest, atresia, anovulation, dysmenorrheal, dysfunctional uterine bleeding, infertility and androgen-producing tumors.

93. A kit comprising a recombinant MIS protein of any of paragraphs 1-21 and a pharmaceutically acceptable carrier.

94. The kit of paragraph 93, optionally further comprising instructions of use of the recombinant MIS protein for the treatment of cancer or treatment of an androgenic dependency disorder.

The invention can be understood more fully by reference to the following detailed description and illustrative examples, that are intended to exemplify non-limiting embodiments of the invention.

EXAMPLES

The following examples are provided for illustrative purposes only and are not intended to limit the scope of the invention.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the Figs. was chosen and described in order to best explain the principles of the invention, the practical application, and to enable others of ordinary skill in the art to understand the invention for various embodiments with various modifications as are suited to the particular use contemplated.

Materials and Methods

Constructs and Plasmid Cloning.

WT-MIS: pBG311 Vector with Genomic Sequence of MIS.

The vector was constructed as previously described (Cate et al, 1986). Briefly, the genomic sequence of human MIS was sub-cloned into a pBG311 expression vector from chMIS33 which was isolated from a human cosmid library using a bovine cDNA probe (Cate et al. 1986).

RF-MIS: pcDNA 3.1 and pAAV-IRES-NEO Vectors Containing MIS cDNA with Native MIS Leader Sequence, Modified Cleavage Site, and Flag Tag.

The coding sequence of MIS, present in a pcDNA3.1 vector containing a FLAG-labeled full-length human MIS cDNA sequence previously described (Papakostas et al, 2010) was subcloned into a pAAV-IRES-Neo expression vector at an ECORV site. This coding sequence contains a FLAG-epitope inserted after a modified cleavage site at position 428 (RARR/S) (SEQ ID NO: 27) (Papakostas et al, 2010).

LR-MIS: pcDNA 3.1 Vector Containing MIS cDNA with Human Serum Albumin Leader Sequence and Modified Cleavage Site.

The pcDNA3.1 vector containing a full-length human MIS cDNA sequence containing a modified cleavage site, as previously described (Papakostas et al, 2010) was used to incorporate the albumin leader sequence. The albumin leader was cloned in the place of the MIS leader using a forward primer containing an EcoRV site: CGAGATACAT-GAAGTGGGTGAGCTTCATCAGCCTGCTGTTCCTGT TCAGCAGCGCTTA CTCCCGCGGTGTGTTCCG GCGC AGAGCAGAGGAGCCAGCTGTG (SEQ ID NO: 11) (with the nucleic acid encoding the leader sequence highlighted in bold) and a backward primer at position 451-432 of MIS GCTCCTGGAACCTCAGCGAG (SEQ ID NO: 12).

LRF-MIS: pcDNA 3.1 Vector Containing MIS cDNA with Human Serum Albumin Leader Sequence, Modified Cleavage Site and Flag Tag.

The pcDNA3.1 vector containing a full-length human MIS cDNA sequence containing a modified cleavage site and a flag tag, as previously described (Papakostas et al, 2010) was used to incorporate the albumin leader sequence as described above.

Transfections and Cloning:

Wild-Type MIS (WT-MIS).

The WT-MIS construct (pBG311) along with pSV2DHFR was previously transfected in DHFR− CHO cells and the B9 clone was selected as the highest expresser as previously described (Cate et al, 1986).

RARR/S-Flag MIS (RF-MIS) ("RARR/S" Disclosed as SEQ ID NO: 27):

The RF-MIS construct (in pAAV-IRES-NEO) was transfected in CHO-S cells using Fugene 6 (Roche) according to the manufacturer's protocol and the CHO93 stably expressing clone was selected under geneticin selection (550 ug/ml) as the highest expresser determined by western blot.

LR-MIS.

The LR-MIS construct (in pcDNA3.1) was transfected in CHO-K1 cells using lipofectamine 2000 (invitrogen), according to the manufacturer's protocol. Clones were selected in 800 ug/ml of geneticin, and the highest expressers as determined by western blot (LR8, 11 and 22) were chosen for further study.

LRF-MIS.

The LRF-MIS construct (in pcDNA3.1) was transfected in CHO-K1 cells using lipofectamine 2000 (invitrogen), according to the manufacturer's protocol. Clones were selected in 800 ug/ml of geneticin (G418), and the highest expressers as determined by western blot (LRF8, 18 and 22) were chosen for further study.

Media and Culture Conditions:

B9 clone. B9 is grown in roller bottles (1700 $cm^2$) with 250 ml of alpha MEM-supplemented with 5% female fetal calf serum (FFCS) (Biologos), 0.24 µM methotrexate, 2 nM glutamine, 100 U/ml penicillin and 100 ug/ml streptomycin (Invitrogen) maintained confluent for several months in 5%

CO2, at 37 C while media is collected every 3-4 days. Media is screened by western and MIS ELISA to monitor and measure production.

CHO93 clone.

CHO93 is grown in roller bottles (1700 cm$^2$) with 250 ml of DMEM:F12 supplemented with 10% FFCS, 550 ug/ml of geneticin, 2 nM glutamine, 100 U/ml penicillin and 100 ug/ml streptomycin (Invitrogen) maintained confluent for several months in 5% CO2, at 37 C while media is collected every 3-4 days. Media is screened by western and MIS ELISA to monitor and measure production.

LR8, 11, 22 and LRF8, 18, 22 Clones.

Both LR and LRF clones are grown in roller bottles (1700 cm$^2$) with 250 ml of DMEM supplemented with 10% FFCS, 800 ug/ml of geneticin, 2 nM glutamine, 100 U/ml penicillin and 100 ug/ml streptomycin (Invitrogen) maintained confluent for several months in 5% CO2, at 37 C while media is collected every 7 days. Media is screened by western and MIS ELISA to monitor and measure production.

Purification of MIS.

Purification using immunoaffitnity anti-Flag beads. RF-MIS and LRF-MIS, which contain a flag tag, are isolated from serum-containing media collected from roller bottles of stably expressing clones of CHO (CHO93, LRF8, LRF18, LRF22) as described above. Collected media is spun down to discard dead cells and the supernatant is collected into 500 ml containers and stored in −20 C until purification. For purification, media is thawed at 4 C overnight and then incubated with anti-FLAG agarose beads (SIGMA, 500 µl packed beads/500 ml media), mixing with rotation overnight at 4 C. Subsequently, the beads are precipitated at 13000 rpm, for 10 seconds and washed extensively (7x) with coldIX Tris Buffered Saline (TBS) (SIGMA). All reagents are kept on ice. RF-MIS and LRF-MIS is eluted with 50 µg of 3×FLAG peptide (SIGMA)/500 µl beads in 1×TBS at 25 C for 45 minutes with rotation. The beads are spun down at 13000 rpm, for 10 seconds at room temperature and the supernatant containing the FLAG MIS is collected, aliquoted, and stored in low protein binding Eppendorf tubes (VWR) at −80 C for subsequent use.

Purification Using Anti-MIS 6E11 Immunoaffinity Column.

The 6E11 MIS monoclonal antibody column was produced as previously described (Ragin et al, 1992). Briefly, a 5 ml immunoaffinity column was constructed using approximately 50 mg of protein A—sepharose (Sigma Chemical Co., St Louis, Mo.)—purified mouse monoclonal anti-human rhMIS antibody, as previously described. [Ragin 1992, Hudson 1990], covalently attached to 5 ml packed Affigel-10 agarose resin (Biorad Laboratories, Richmont, Calif.) per manufacturer's instructions (approximately 80% coupling efficiency). The column was blocked with ethonalamine and equilibrated with 50 ml of 20 mM 4-(2-hydroxyethyl)-1-piperazineethanesulfonic acid (Hepes), pH 7.4 and 200 ml concentrated (10x, serum free) conditioned media loaded at 1 column vol/h at 4° C. After loading, the column was washed with 10 column volumes of 20 mM Hepes, pH 7.4. A pre-elution step employed 1 column volume containing 0.5M NaCl in 20 mM Hepes, pH 7.4. Elution of bound rhMIS was achieved using 1M Acetic Acid in 20 mM Hepes, pH 3.0. The majority of the rhMIS eluted in a 2-5 ml fraction, post 2 ml void volume fraction. Eluted rhMIS was immediately neutralized with NaOH to a pH between 7.0 and 7.4. The acid eluted fractions were dialyzed overnight versus 0.02M Hepes, pH7.4. The resulting rhMIS was analyzed for total protein by Bradford method (Bradford, 1976) and for rhMIS concentrations by an enzyme-linked immunoassay (Hudson 1990) and examined by polyacrylamide gel electrophoresis (Weber 1969), Western blot analysis (Towbin 1979), in vitro Mullerian duct regression bioassays and tumor antiproliferative assays (Chin 1991).

Electrophoresis and Western Blotting

Samples were reduced with 100 mM Dithiothreitol in 1× Laemmli buffer (0.0625 mM Tris pH 6.8, 2% (w/v) SDS stock, 10% (v/v) glycerol, 0.002% (w/v) bromophenol blue) and heat denatured on a thermoblock at 70° C. for 10 min. Samples were run on a 4-12% Tris-Bis NuPage Novex "mini" gel (Invitrogen) at 130V with 1×MES running buffer (Invitrogen). Gels were stained with coomassie stain (0.3% Brilliant Blue R-250, 45% Methanol, 10% Acetic Acid in $H_2O$) for 15 min at room temperature with agitation. Subsequently, they were agitated overnight at room temperature in de-staining solution (20% methanol, 10% acetic acid in $H_2O$) with agitation.

For Western blot analysis, gels were transferred onto PVDF (Millipore) membranes, previously equilibrated in 1× NuPage transfer buffer (Invitrogen) containing 12% (v/v) methanol, at 25V for 45 min and at 35V for another 45 min. Membranes were blocked with 1×PBS, 0.1% Tween-20 containing 5% nonfat dry milk for 30 min at room temperature and probed with horseradish peroxidase conjugated mouse monoclonal anti-FLAG M2 antibody (SIGMA) (1:1000), goat C20 anti-MIS c-terminus antibody (Santa Cruz) (1:200) or rabbit MGH4 anti-MIS n-terminus MIS antibody (custom) (1:1000). Blots were washed two times 5 min each at room temperature with 1×PBS, Tween-20 0.1%, and incubated with appropriate secondary antibody if necessary, and washed three times (5 mins) Proteins bands were visualized with the ECL kit detection system (Perkin-Elmer) onto Kodak Biomax MR film.

Animals and Organ Cultures:

The standard organ culture bioassay for Mullerian Inhibiting Substance (MIS) was performed as described previously (Donahoe, 1977). Briefly, female urogenital ridges from timed pregnant rats at E14.5 (Harlan) were dissected and cultured on agar coated stainless steel grids mounted above fortified Cambridge Medical Research Laboratories (CMRL) 1066 media (Life Technologies) supplemented with 10% FFCS (to avoid an effect of bovine MIS in male serum), 1% penicillin/streptomycin, 1% L-Glutamine, 1% Fungizone (Invitrogen), and 1 nM testosterone (Sigma). After incubation for 72 hours in humidified 5% $CO_2$ at 37° C., the specimens were fixed in Zamboni buffer (15% formaldehyde solution, and 5% picric acid), and embedded in paraffin, and 8-um sections of the cephalic end were stained with hematoxylin and eosin. The sections were then scored from 0 (no regression) to 5 (complete regression), by two experienced observers. Cultures were carried out with purified RF-MIS, LRF-MIS or WT-MIS at a final concentration of 5 µg/ml, and at lower doses of 3, 2, and 1 µg/ml.

Example 1

Purification of Mullerian Inhibiting Substance (MIS) protein for preclinical efficacy (Pieretti-Vanmarcke et al. 2006), has predominantly been done from conditioned media from CHO cells transfected with a genomic clone (Cate et al. 1986). The media was then immunoaffinity purified (Ragin et al. 1992) using a mouse monoclonal antibody (Hudson et al. 1990) or purified by serial chromatography (Lorenzo et al. 2002). Biologic activity was detected in an embryonic organ culture Mullerian duct regression assay (Donahoe et al. 1977) and immunoactivity detected by an ELISA (Hudson et al. 1990) using monoclonal and polyclonal antibodies raised to human MIS. The transfected CHO cells were subsequently adapted to serum free conditions and suspension culture (MacLaughlin/Stafford/Dean, Donahoe unpublished), clonally selected, scaled, and purified as above. Western analysis confirmed 25-30% cleavage to yield the homodimerized C-terminus bioactive moeity which was held in noncovalent association with the homodimerized N terminus, with cleavage at the Kex-like, primary cleavage site at amino acid residues 426-427, and secondary cleavage at amino acid positions 229-230. Bands on reduced electrophoretic gels at 70, 55, 34, 24, and 12.5 kDa were all MIS fragments, as determined by amino acid sequencing (Ragin et al. 1992; Lorenzo et al. 2002), and representative of predicted Kex and dibasic cleavage products.

To optimize cleavage and the primary cleavage site at amino acid position 427, the recognition sequence was mutagenized to create a dibasic cleavage site; the RAQR/R (SEQ ID NO: 28) variant was bioactive (Kurian et al, 1994). Position 425 (corresponding to amino acid residue 450 of SEQ ID NO: 1) was then mutagenized to create a more consensus Kex cleavage site (Nachtigal & Ingraham 1996) (Hosaka et al. 1991), RARR/S (SEQ ID NO: 27), and an 8 amino acid Flag (DYKDDDDK) (SEQ ID NO:8) tag was added just downstream of the first serine in the C-terminus to aid in detection and purification. Expression of this variant resulted in improved cleavage and increased bioactivity. By comparison, when the C-terminal arginine (Kurian et al 1994) was followed by Flag, the protein produced by this construct was bioinactive (Papakostas et al 2010); thus, the serine appeared to be important for preservation of bioactivity. The RARR/S (SEQ ID NO: 27) Flag construct (Papakostas et al 2010) was transfected into CHO cells and improved cleavage and preservation of bioactivity confirmed (Papakostas et al, 2010). The modification of the cleavage site increased the cleavage to over 50-60% (Papakostas et al, 2010).

To scale expression, the MIS RARR/S (SEQ ID NO: 27) Flag construct was further modified to substitute the endogenous MIS leader sequence with that of human serum albumin (HSA). HSA is the most abundant protein in plasma and is produced at a very high rate by the liver to achieve a blood concentration ranging from 3.4 to 5.4 g/dL (Farrugia 2010). The production and processing of HSA is finely tuned to allow efficient maturation and secretion of the protein. HSA, like MIS is synthesized as a prepro-protein, which contains a leader sequence that is subsequently cleaved during maturation. This HSA leader sequence consists of only 24 AA, is not immunogenic in humans, and is removed during protein processing. Here the inventors demonstrate that substitution of the MIS leader sequence with that of HSA increases production, and unexpectedly, cleavage, which correlates with increased potency of the recombinant human MIS product.

Example 2

Previous efforts to scale up production of human recombinant MIS led us to develop a new construct featuring the cDNA of hMIS with a modified cleavage site at position 427/428 inserted into pcDNA3.1 (Papakostas et al, 2010). By substituting the modified RARR/S (SEQ ID NO: 27) for the endogenous RAQR/S (SEQ ID NO: 26) (noted as R in constructs), and inserting a Flag tag immediately downstream of the cleavage site (noted as F in construct) (Table 1) (FIG. 1), the inventors demonstrated increased cleavage of the tagged C-terminus (Papakostas et al, 2010). Furthermore, the recombinant RARR/S-Flag MIS ("RARR/S" disclosed as SEQ ID NO: 27) (referred to herein as "RF-MIS") protein retained bioactivity in the fetal rat urogenital ridge assay (Papakostas et al, 2010). To overcome low expression yields, the backbone vector of RF-MIS was switched to pAAV-IRES-Neo, and cloned into CHO-S cells, and screened under high Geneticin concentration. The resulting expression vector is polycistronic and includes an internal ribosomal entry site (IRES) driving expression of the neomycin resistance cassette downstream of MIS, allowing for better selection of high expressers. The highest expressing clone, CHO93, was subsequently scaled up for production using roller bottles and recombinant RF-MIS was purified using anti-flag M2 immunoaffinity beads (Table 2). However, while RF-MIS has increased cleavage of the active C-terminus, and importantly, less internal cryptic cleavage (FIG. 2)(FIG. 3), the yield and production of the cDNA clone CHO93 (0.16 pg/cell/day) remains much lower than that of the genomic clone B9 (10.59 pg/cell/day)(Table 3), although it is unclear whether this is due to the expression vector, the CHO cells, the nature of the drug selection, or the type of message produced (cDNA versus genomic MIS).

To improve production, the original R-MIS and RF-MIS construct in pcDNA3.1 vectors were modified by substituting the 24 AA of the HSA leader sequence (pre-pro peptide) (herein noted as L in constructs) to the 25AA MIS leader to create the "LR" and "LRF" constructs (Table 1) (FIG. 1).

TABLE 1

List of modifications to the MIS wild-type sequence and corresponding nomenclature.

| Notation | Native | Modification (shown in BOLD) | Position (AA) (normal protein nomenclature) | Position on SEQ ID NO: 1 | Purpose |
| --- | --- | --- | --- | --- | --- |
| R | RAQR/S (SEQ ID NO: 26) | RARR/S (SEQ ID NO: 27) | 423-427 | 448-452 | Furin/Kex2 census site for improved cleavage |
| F | n/a | FLAG Tag (DYKDDDDK) (SEQ ID NO: 8) | Located between 427-428 | Located between 452-453 of SEQ ID NO: 1 | C-terminus FLAG tag for easier purification and tracking. |
| L | MIS Leader Sequence | Albumin Leader Sequence | 1-25 | 1-25 | Increased production, secretion and cleavage. |

HSA leader sequence fusion has been shown to increase production of recombinant interleukins (Carter et al, 2010) and TNF-alpha (Maeda Y et al 1997), and has been suggested as a way to produce proteins otherwise difficult to express and to scale. Furthermore, HSA is known to also enhance secretion of fused proteins such as human lysozyme in yeast expression system with *Pichia pastoris* (Xiong et al, 2008). The three highest stably expressing clones in CHOK1 were selected for further analysis: LR8/11/18 and LRF8/18/22 (FIG. 2). Both cloning efficiency and expression levels were greater for the LR clones than the LRF clones, suggesting the Flag tag may make expression less efficient. Similarly to CHO93, all LR and LRF clones have reduced peptide fragments resulting from internal cryptic cleavage at position 229, when compared to the wild type (WT-MIS) protein produced by B9. Unexpectedly, they also appear to have greater proportion of cleaved C-terminus (FIGS. 2 and 3). This increased cleavage could be explained by the strong evolutionary pressures on the albumin leader for efficient processing in the trans-golgi network and transport to secretory vesicles, since albumin is endogenously secreted at much higher rate than MIS (Rothschild et al. 1988). LRF18 was chosen for characterization since it is the highest expressing LRF clone, and can be purified and tracked using the Flag-tag (Table 2).

TABLE 2

List of constructs and cell line clones producing MIS and corresponding purification methods.

| Construct | Clones | Vector | Cell Line | Purification |
|---|---|---|---|---|
| MIS | B9 | MIS WT genomic sequence in pBG311 plasmid. | CHO cells lacking the DHFR gene. | Immunoaffinity using 6E11 monoclonal antibody against MIS or serial chromatography. |
| RF-MIS | CHO93 | MIS cDNA sequence inserted into pAAV-IRES-Neo plasmid. | CHO-S | Immunoaffinity using M2 monoclonal antibody against FLAG tag. |
| LR-MIS | LR8 LR11 LR18 | MIS cDNA sequence inserted into pcDNA3.1plasmid. | CHO-K1 | Immunoaffinity using 6E11 monoclonal antibody against MIS or serial chromatography. |
| LRF-MIS | LRF8 LRF18 LRF22 | MIS cDNA sequence inserted into pcDNA3.1plasmid. | CHO-K1 | Immunoaffinity using M2 monoclonal antibody against FLAG tag. |

When cultured for 24 hours in flasks, the concentration of MIS, as detected by ELISA, is greater in the media of B9 (WT-MIS) (15 μg/ml) than in the media of clones (LR8: 3.04 μg/ml); LR11: 11.66 μg/ml; LR22: 6.28 μg/ml) (Table 3). The highest producing clone of LR, LR11 secretes 3.24 pg/cell/day of MIS while the WT clone B9 produces 10.58 pg/cell/day, however, LR11 cells grow much more compact fashion, conversely, the highest expressing clone of LRF, LRF18 has both higher concentration (1.1 μg/ml) and higher production (0.26 pg/cell/day) than RF-MIS (CHO93) with (0.67 μg/ml) and (0.15 pg/cell/day) (Table3). Thus, the addition of the HSA leader increases the production of the flag-tagged MIS product but not the untagged product. However, as the flag-tagged constructs clearly do not produce as much as the untagged ones, the flag tag may be interfering with protein stability or expression. Coomassie stains and western blot show that the product purified from LRF18 by anti-flag immunoaffinity purification has fewer bands representative of internal cleavage (Ragin 1992) than the MIS purified from WT-MIS (B9) using anti-MIS affinity purification (FIG. 3).

TABLE 3

Purification yield from MIS from various constructs.

|  | WT-MIS | RF-MIS | LRF-MIS | LR-MIS |
|---|---|---|---|---|
| MIS concentration (μg/ml) at 24 hours | 15 | 0.67 | 1.10 | 11.67 |
| Production (pg/cell/day) | 10.59 | 0.15 | 0.26 | 3.24 |
| Purification yield (% w/w) | 15% | 20% | 20% | 15% |
| Percent cleavage | 20% | 50% | 90% | 90% |

Figure 4A:
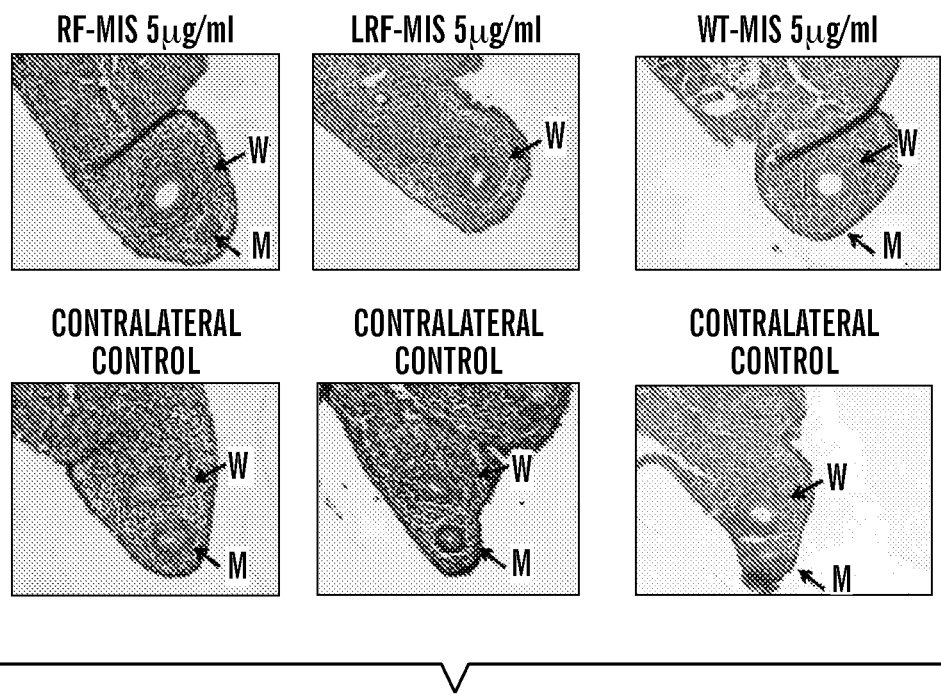
FIGS. 4A-4B show the comparison of 5 ug/ml (35 uM) of WT, RF, and LRF recombinant MIS in a Mullerian duct regression bioassay. Recombinant human MIS produces was incubated for 72 h with fetal rat uro-genital ridges.
Figure 4B:
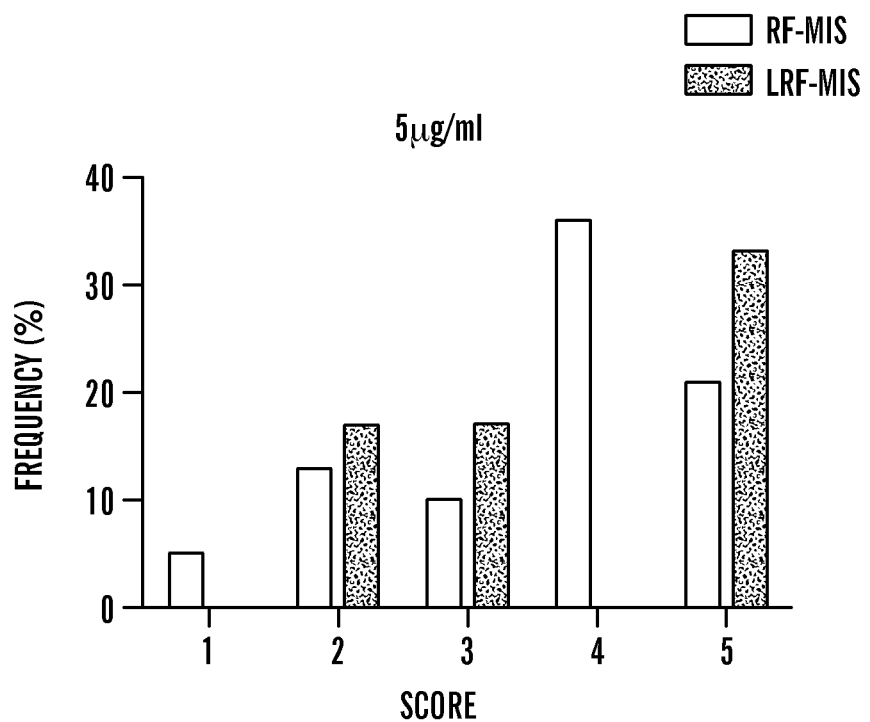

Since the C-terminus of MIS has previously been shown to be the active moiety (Pepinski 1988, Maclaughlin et al 1992), increased cleavage should correlate with greater bioactivity in the rat UGR assay. Here, the inventors demonstrate that that LRF-MIS is able to fully regress the Mullerian duct at 5 μg/ml (35 μM) and show greater activity than RF-MIS and WT-MIS at these concentrations, which only display partial regression (FIG. 4). Furthermore LRF-MIS continues to display full regression even at lower doses, down to 2 μg/ml, a dose at which WT-MIS no longer shows any activity (data not shown). Accordingly, the presence of the leader sequence (L) in the LRF-MIS recombinant human MIS protein results in a dose-dependently decrease the regression of the Mullerian ducts, as compared to the RF-MIS construct, indicating that this construct has a higher potency and is more active than the RF-MIS construct.

Taken together, the inventors demonstrate herein that the LR product results in a greater yield of production with increased cleavage and higher bioactivity or potency.

Accordingly, the inventors demonstrate that the HSA leader sequence surprisingly resulted in an increased yield (both higher concentration and higher production) of the recombinant human MIS protein (see FIGS. 2 and 3). Furthermore, the presence of the HSA leader sequence also resulted in an unexpectedly increase in cleavage from the primary cleavage site (corresponding to cleavage at 451/452 of SEQ ID NO: 1 (or 426/427 of conventional amino acid nomenclature of wild-type human MIS protein) (see FIGS. 2 and 3). This increased yield and increased cleavage was surprising because with an increased yield (and therefore more protein produced by the cell), one would expect a decreased cleavage as the activity of the available cleavage enzymes becomes saturated and overextended. However, this was not the case—in fact the exact opposite occurred where with increased protein production there was increased cleavage from the primary cleavage site.

This is particularly unexpected as the effect of the leader sequence, which is not located anywhere near the cleavage site of the primary cleavage site of MIS, was not expected to have an effect on increased cleavage as the leader sequence is typically cleaved first before the post-translation cleavage of the proprotein MIS.

Furthermore, the leader sequence also resulted in less cleavage from the secondary cleavage site (located between amino acid residues 229/230 of normal wild-type MIS numbering or corresponding to residues 254/255 of SEQ ID NO: 1). This is also surprising, considering that there was no modification to the secondary cleavage site.

Additionally, the presence of the leader sequence also increased the production and yield even when a FLAG tag is present in the recombinant human MIS protein. (The FLAG tag significantly decreases the yield as shown in Table 3). This again was a surprising discovery, as the leader sequence is not located anywhere near the FLAG tag and it would not be expected that such a modification to the leader sequence would increase the production yield of a protein comprising a FLAG tag.

Example 3

LR11 is grown in 5 layer flask with 250 ml of DMEM or in 10 layer flasks (1700 cm$^2$) with 500 ml media supplemented with 10% FFCS, 800 ug/ml of geneticin, 2 nM glutamine, 100 U/ml penicillin and 100 ug/ml streptomycin (Invitrogen) maintained confluent for several months in 5% CO2, at 37 C. Once a week, the media is replaced with a serum-free media which omits FFCS and replaces it with non-essential amino acids (NEAA) and ITS (insulin, transferring, selenium) supplements for 72 h. The media is then concentrated 10× using tangential flow osmosis membranes. Using these methods media of 4-5 ug/ml is concentrated to 25-50 ug/ml, and effective purification yield of LR-MIS rises to approximately 30%.

TABLE 4

Purification yield from MIS from various constructs using a new serum-free media purification protocol.

|  | WT-MIS | RF-MIS | LRF-MIS | LR-MIS |
| --- | --- | --- | --- | --- |
| MIS concentration (µg/ml) at 24 hours | 16.821 | 1.236 | 2.149 | 4.866 |
| Production (pg/cell/day) | 7.597 | 0.254 | 0.430 | 1.142 |
| Concentration in serum-free media at 24 h | 1.528 | 0.223 | 0.457 | 1.411 |
| Purification yield (% w/w) | 15% | 20% | 20% | 30% |
| Percent cleavage in serum-free media | 25% | 50% | 37% | 79% |

REFERENCES

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference. Accordingly, the references are each incorporated herein in their entirety by reference.

Cate, R. L. et al., 1986. Development of mullerian inhibiting substance as an anti-cancer drug. *Cold Spring Harbor symposia on quantitative biology,* 51 Pt 1, pp. 641-647.

Donahoe, P. K., Ito, Y. & Hendren, W. H., 3rd, 1977. A graded organ culture assay for the detection of Mullerian inhibiting substance. *The Journal of surgical research,* 23(2), pp. 141-148.

Farrugia, A., 2010. Albumin usage in clinical medicine: tradition or therapeutic? *Transfusion medicine reviews,* 24(1), pp. 53-63.

Hosaka, M. et al., 1991. Arg-X-Lys/Arg-Arg motif as a signal for precursor cleavage catalyzed by furin within the constitutive secretory pathway. *Journal of Biological Chemistry,* 266(19), pp. 12127-12130. Available at: [Accessed Feb. 21, 2013].

Hudson, P. L. et al., 1990. An immunoassay to detect human müllerian inhibiting substance in males and females during normal development. *The Journal of clinical endocrinology and metabolism,* 70(1), pp. 16-22.

Lorenzo, H. K. et al., 2002. New approaches for high-yield purification of Müllerian inhibiting substance improve its bioactivity. *Journal of chromatography. B, Analytical technologies in the biomedical and life sciences,* 766(1), pp. 89-98.

Nachtigal, M. W. & Ingraham, H. A., 1996. Bioactivation of Müllerian inhibiting substance during gonadal development by a kex2/subtilisin-like endoprotease. *Proceedings of the National Academy of Sciences of the United States of America,* 93(15), pp. 7711-7716.

Pieretti-Vanmarcke, R. et al., 2006. Recombinant human Mullerian inhibiting substance inhibits long-term growth of MIS type II receptor-directed transgenic mouse ovarian cancers in vivo. *Clinical Cancer Research: An Official Journal of the American Association for Cancer Research,* 12(5), pp. 1593-1598.

Ragin, R. C. et al., 1992. Human müllerian inhibiting substance: enhanced purification imparts biochemical stability and restores antiproliferative effects. Protein expression and purification, 3(3), pp. 236-245.

Rothschild, M. A., Oratz, M. & Schreiber, S. S., 1988. Serum albumin. *Hepatology* (Baltimore, Md.), 8(2), pp. 385-401.

Papakostos, T. D. et al., Development of an efficenty cleaved, bioactive, highly pure FLAG-tagged recombinant human Mullerian Inhibiting Substance. *Protein Expression and Purification,* 2010; 70; 32-38.

SEQUENCE LISTING:
MIS (560AA)-amino acid sequence (underlined
identifies native MIS leader sequence)
SEQ ID NO: 1

<u>mrdlpltsla lvlsalgall gtealr</u>aeep avgtsglifr edldwppgsp qeplclvalg gdsngssspl rvvgalsaye qaflgavqra rwgprdlatf gvcntgdrqa alpslrrlga wlrdpggqrl vvlhleevtw eptpslrfqe pppggagppe lallvlypgp gpevtvtrag lpgaqslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal agfpqglvnl sdpaalerll dgeepllll1 rptaattgdp aplhdptsap watalarrva aelqaaaael rslpglppat apllarllal cpggpgglgd plralllika lqglrvewrg rdprgpgrag rsagataadg pcalrelsvd lraersvlip etyqanncqg vcgwpqsdrn prygnhvvll lkmqvrgaal arppccvpta yagkllisls eerisahhvp nmvatecgcr LR (559AA) BOLD indicates-albumin leader sequence;
Underlined identifies the Modified cleavage site
SEQ ID NO: 2
mkwvtfisll flfssaysrg vfrr <u>r</u>aeep avgtsglifr edldwppgsp qeplclvalg gdsngssspl rvvgalsaye qaflgavqra rwgprdlatf gvcntgdrqa alpslrrlga wlrdpggqrl vvlhleevtw eptpslrfqe pppggagppe lallvlypgp gpevtvtrag lpgaqslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal agfpqglvnl sdpaalerll dgeepllll1 rptaattgdp aplhdptsap watalarrva aelqaaaael rslpglppat apllarllal cpggpgglgd plralllika lqglrvewrg rdprgpgra<u>R</u> rsagataadg pcalrelsvd lraersvlip etyqanncqg vcgwpqsdrn prygnhvvll lkmqvrgaal arppccvpta yagkllisls eerisahhvp nmvatecgcr LRF (567AA) Italicized indicates Flag tag
(DYKDDDDK (SEQ ID NO: 8))
SEQ ID NO: 3
mkwvtfisll flfssaysrg vfrr raeep avgtsglifr edldwppgsp qeplclvalg gdsngssspl rvvgalsaye qaflgavqra rwgprdlatf gvcntgdrqa alpslrrlga wlrdpggqrl vvlhleevtw eptpslrfqe pppggagppe lallvlypgp gpevtvtrag lpgagslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal -continued agfpqglvnl sdpaalerll dgeepllll1 rptaattgdp aplhdptsap watalarrva aelqaaaael rslpglppat apllarllal cpggpgglgd plralllika lqglrvewrg rdprgpgra<u>R</u> rs*DYKDDDDK* agataadg pcalrelsvd lraersvlip etyqanncqg vcgwpqsdrn prygnhvvll lkmqvrgaal arppccvpta yagkllisls eerisahhvp nmvatecgcr LR-nucleic acid sequence
SEQ ID NO: 4
*ATGAAGTGGGTGAGCTTCATCA*GCCTGCTGTTCCTGTTC

*AGCAGCGCTTACTCCCGGCGGTGTGTTCCGCCGCAGAGCA*

GAGGAGCCAGCTGTGGGCACCAGTGGCCTCATCTTCCGAGAAGACTTGG

ACTGGCCTCCAGGCAGCCCACAAGAGCCTCTGTGCCTGGTGGCACTGGG

CGGGGACAGCAATGGCAGCAGCTCCCCCCTGCGGGTGGTGGGGGCTCTA

AGCGCCTATGAGCAGGCCTTCCTGGGGGCCGTGCAGAGGGCCCGCTGGG

GCCCCCGAGACCTGGCCACCTTCGGGGTCTGCAACACCGGTGACAGGCA

GGCTGCCTTGCCCTCTCTACGGCGGCTGGGGGCCTGGCTGCGGGACCCT

GGGGGGCAGCGCCTGGTGGTCCTACACCTGGAGGAAGTGACCTGGGAGC

CAACACCCTCGCTGAGGTTCCAGGAGCCCCCGCCTGGAGGAGCTGGCCC

CCCAGAGCTGGCGCTGCTGGTGCTGTACCCTGGGCCTGGCCCTGAGGTC

ACTGTGACGAGGGCTGGGCTGCCGGGTGCCCAGAGCCTCTGCCCCTCCC

GAGACACCCGCTACCTGGTGTTAGCGGTGGACCGCCCTGCGGGGGCCTG

GCGCGGCTCCGGGCTGGCCTTGACCCTGCAGCCCCGCGGAGAGGACTCC

CGGCTGAGTACCGCCCGGCTGCAGGCACTGCTGTTCGGCGACGACCACC

GCTGCTTCACACGGATGACCCCGGCCCTGCTCCTGCTGCCGCGGTCCGA

GCCCGCGCCGCTGCCTGCGCACGGCCAGCTGGACACCGTGCCCTTCCCG

CCGCCCAGGCCATCCGCGGAACTCGAGGAGTCGCCACCCAGCGCAGACC

CCTTCCTGGAGACGCTCACGCGCCTGGTGCGGGCGCTGCGGGTCCCCCC

GGCCCGGGCCTCCGCGCCGCGCCTGGCCCTGGATCCGGACGCGCTGGCC

GGCTTCCCGCAGGGCCTAGTCAACCTGTCGGACCCCGCGGCGCTGGAGC

GCCTACTCGACGGCGAGGAGCCGCTGCTGCTGCTGAGGCCCACTGC

GGCCACCACCGGGGATCCTGCGCCCCTGCACGACCCCACGTCGGCGCCG

TGGGCCACGGCCCTGGCGCGCCGCGTGGCTGCTGAACTGCAAGCGGCGG

CTGCCGAGCTGCGAAGCCTCCCGGGTCTGCCTCCGGCCACAGCCCCGCT

GCTGGCGCGCCTGCTCGCGCTCTGCCCAGGTGGCCCCGGCGGCCTCGGC

GATCCCCTGCGAGCGCTGCTGCTCCTGAAGGCGCTGCAGGGCCTGCGCG

TGGAGTGGCGCGGGCGGGATCCGCGCGGGCCGGGTCGGGCACGGCGCAG

CGCGGGGGGCCACCGCCGCCGACGGGCCGTGCGCGCTGCGCGAGCTCAGC

GTAGACCTCCGCGCCGAGCGCTCCGTACTCATCCCCGAGACCTACCAGG

CCAACAATTGCCAGGGCGTGTGCGGCTGGCCTCAGTCCGACCGCAACCC

GCGCTACGGCAACCACGTGGTGCTGCTGCTGAAGATGCAGGCCCGTGGG

GCCGCCCTGGCGCGCCCACCCTGCTGCGTGCCCACCGCCTACGCGGGCA

AGCTGCTCATCAGCCTGTCGGAGGAGCGCATCAGCGCGCACCACGTGCC

CAACATGGTGGCCACCGAGTGTGGCTGCCGGTGA

LRF-nucleic acid sequence

SEQ ID NO: 5

ATGAAGTGGGTGAGCTTCATCAGCCTGCTGTTCCTGTTC

AGCAGCGCTTACTCCCGCGGTGTGTTCCGCCGCAGAGCA

GAGCCAGCTGTGGGCACCAGTGGCCTCATCTTCCGAGAAGACTTGGACT

GGCCTCCAGGCAGCCCACAAGAGCCTCTGTGCCTGGTGGCACTGGGCGG

GGACAGCAATGGCAGCAGCTCCCCCCTGCGGGTGGTGGGGGCTCTAAGC

GCCTATGAGCAGGCCTTCCTGGGGGCCGTGCAGAGGGCCCGCTGGGGCC

CCCGAGACCTGGCCACCTTCGGGGTCTGCAACACCGGTGACAGGCAGGC

TGCCTTGCCCTCTCTACGGCGGCTGGGGCCTGGCTGCGGGACCCTGGG

GGGCAGCGCCTGGTGGTCCTACACCTGGAGGAAGTGACCTGGGAGCCAA

CACCCTCGCTGAGGTTCCAGGAGCCCCGCCTGGAGGAGCTGGCCCCCC

AGAGCTGGCGCTGCTGGTGCTGTACCCTGGGCCTGGCCCTGAGGTCACT

GTGACGAGGGCTGGGCTGCCGGGTGCCCAGAGCCTCTGCCCCTCCCGAG

ACACCCGCTACCTGGTGTTAGCGGTGGACCGCCCTGCGGGGCCTGGCG

CGGCTCCGGGCTGGCCTTGACCCTGCAGCCCCGCGGAGAGGACTCCCGG

CTGAGTACCGCCCGGCTGCAGGCACTGCTGTTCGGCGACGACCACCGCT

GCTTCACACGGATGACCCCGGCCCTGCTCCTGCTGCCGCGGTCCGAGCC

CGCGCCGCTGCCTGCGCACGGCCAGCTGGACACCGTGCCCTTCCCGCCG

CCCAGGCCATCCGCGGAACTCGAGGAGTCGCCACCCAGCGCAGACCCCT

TCCTGGAGACGCTCACGCGCCTGGTGCGGGCGCTGCGGGTCCCCCCGGC

CCGGGCCTCCGCGCCGCGCCTGGCCCTGGATCCGGACGCGCTGGCCGGC

TTCCCGCAGGGCCTAGTCAACCTGTCGGACCCCGCGGCGCTGGAGCGCC

TACTCGACGGCGAGGAGCCGCTGCTGCTGCTGAGGCCCACTGCGGC

CACCACCGGGGATCCTGCGCCCCTGCACGACCCCACGTCGGCGCCGTGG

GCCACGGCCCTGGCGCGCCGCGTGGCTGCTGAACTGCAAGCGGCGGCTG

CCGAGCTGCGAAGCCTCCCGGGTCTGCCTCCGGCCACAGCCCCGCTGCT

GGCGCGCCTGCTCGCGCTCTGCCCAGGTGGCCCCGGCGGCCTCGGCGAT

CCCCTGCGAGCGCTGCTGCTCCTGAAGGCGCTGCAGGGCCTGCGCGTGG

AGTGGCGCGGGCGGGATCCGCGCGGGCCGGGTCGGGCACGGCGCAGC

*gactacaaggatgacgacgacaag*GCGGGGGCCACCGCCGCCGACGG

GCCGTGCGCGCTGCGCGAGCTCAGCGTAGACCTCCGCGCCGAGCGCTCC

GTACTCATCCCCGAGACCTACCAGGCCAACAATTGCCAGGGCGTGTGCG

GCTGGCCTCAGTCCGACCGCAACCCGCGCTACGGCAACCACGTGGTGCT

GCTGCTGAAGATGCAGGCCCGTGGGGCCGCCCTGGCGCGCCCACCCTGC

TGCGTGCCCACCGCCTACGCGGGCAAGCTGCTCATCAGCCTGTCGGAGG

AGCGCATCAGCGCGCACCACGTGCCCAACATGGTGGCCACCGAGTGTGG

CTGCCGGTGA

HSA Leader Sequence (amino acid sequence):

SEQ ID NO: 6 mkwvtfisll flfssaysrg vfrr

HSA Leader Sequence (nucleic acid sequence):

SEQ ID NO: 7

*ATGAAGTGGGTGAGCTTCATCAGCCTGCTGTTCCTGTTCA*
*GCAGCGCTTACTCCCGCGGTGTGTTCCGCCGCAGAGCA*

FLAG tag (amino acid sequence):

SEQ ID NO: 8

DYKDDDDK

FLAG tag (nucleic acid sequence):

SEQ ID NO: 9

*gactacaaggatgacgacgacaag*

---

The invention claimed is:

1. A recombinant Mullerian Inhibiting Substance (MIS) protein comprising a combination of a polypeptide with at least 95% sequence identity to amino acid residues 26-451 of SEQ ID NO: 1 and a non-MIS leader sequence in place of the MIS leader sequence of amino acids 1-25 of SEQ ID NO: 1, wherein at least residue 450 of SEQ ID NO: 1 is changed from Q to R or a conservative amino acid of R, wherein the recombinant MIS protein has increased cleavage and increased yield of production in vitro as compared to wild-type MIS protein corresponding to amino acid residues of SEQ ID NO: 1, and wherein the recombinant MIS protein does not comprise a FLAG tag.

2. The recombinant MIS protein of claim 1, wherein the recombinant MIS protein is a homodimer comprising two monomers, each monomer comprising a N-terminal domain of the recombinant MIS protein comprising amino acid residues 26-451 of SEQ ID NO: 1, wherein residue 450 of SEQ ID NO: 1 is changed from Q to R or a conservative amino acid of R, and the C-terminal domain of recombinant MIS protein comprising amino acid residues 452-560 of SEQ ID NO: 1.

3. The recombinant MIS protein of claim 1, wherein the non-MIS leader sequence is selected from the group consisting of: albumin leader sequence, immunoglobulin signal peptide fused to a tissue-type plasminogen activator propeptide (IgSP-tPA), murine immunoglobulin signal peptide (IgSP), a MPIF-1 signal sequence (SEQ ID NO: 15); a stanniocalcin signal sequence (SEQ ID NO:16); an invertase signal sequence (SEQ ID NO:17); a yeast mating factor alpha signal sequence (K. lactis killer toxin leader sequence); a hybrid signal sequence (SEQ ID NO:18); a HSA/MFα-1 hybrid signal sequence (SEQ ID NO:19); a K. lactis killer/MFα-1 fusion leader sequence (SEQ ID NO:20); an immunoglobulin Ig signal sequence (SEQ ID NO:21); a Fibulin B precursor signal sequence (SEQ ID NO:22); a clusterin precursor signal sequence (SEQ ID NO: 23); and the insulin-like growth factor-binding protein 4 signal sequence (SEQ ID NO: 24); or a functional variant thereof having at least 95% homology thereof.

4. The recombinant MIS protein of claim 3, wherein the albumin leader sequence is a human albumin sequence (HSA) leader sequence comprising the amino acid sequence of SEQ ID NO: 13 or a functional variant that is at least 95% homologous thereto.

5. The recombinant MIS protein of claim 4, wherein a functional variant of the HSA leader sequence that is at least 95% homologous to SEQ ID NO: 13 is selected from the group consisting of: MKWVTFISLLFLFSSAYSRGVFRR (SEQ ID NO: 6); and MKWVSFISLLFLFSSAYS (SEQ ID NO:14).

6. The recombinant MIS protein of claim 1, further comprising a modification of amino acid 452 of SEQ ID NO: 1 from S to R to increase cleavage as compared to in the absence of such a modification.

7. The recombinant MIS protein of claim 1, which comprises the amino acid sequence of SEQ ID NO: 2 or a recombinant MIS protein having an amino acid sequence at least 95% identical to amino acids 25-559 of SEQ ID NO: 2, where SEQ ID NO: 2 has a R residue at position 449 of SEQ ID NO:2.

8. The recombinant MIS protein of claim 7, which is encoded by nucleic acid sequence of SEQ ID NO: 4.

9. The recombinant MIS protein of claim 1, wherein the conservative amino acid of R is K.

10. The recombinant MIS protein of claim 2, wherein the conservative amino acid of R is K.

11. A pharmaceutical composition comprising the recombinant MIS protein of claim 2 and a pharmaceutically acceptable carrier.

12. A kit comprising a recombinant MIS protein of claim 1 and a pharmaceutically acceptable carrier.

13. A pharmaceutical composition comprising the recombinant MIS protein of claim 10 and a pharmaceutically acceptable carrier.

14. A kit comprising a recombinant MIS protein of claim 9, and a pharmaceutically acceptable carrier.

* * * * *

SEQUENCE LISTING

<160> NUMBER OF SEQ ID NOS: 28

<210> SEQ ID NO 1
<211> LENGTH: 560
<212> TYPE: PRT
<213> ORGANISM: Homo sapiens

<400> SEQUENCE: 1

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

```
Leu Ala Thr Phe Gly Val Cys Asn Thr Gly Asp Arg Gln Ala Ala Leu
                100                 105                 110

Pro Ser Leu Arg Arg Leu Gly Ala Trp Leu Arg Asp Pro Gly Gly Gln
            115                 120                 125

Arg Leu Val Val Leu His Leu Glu Glu Val Thr Trp Glu Pro Thr Pro
        130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Arg Pro
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Lys Ala Leu Gln
            420                 425                 430

Gly Leu Arg Val Glu Trp Arg Gly Arg Asp Pro Arg Gly Pro Gly Arg
        435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510
```

```
Met Gln Val Arg Gly Ala Ala Leu Ala Arg Pro Pro Cys Cys Val Pro
            515                 520                 525

Thr Ala Tyr Ala Gly Lys Leu Leu Ile Ser Leu Ser Glu Glu Arg Ile
        530                 535                 540

Ser Ala His His Val Pro Asn Met Val Ala Thr Glu Cys Gly Cys Arg
545                 550                 555                 560

<210> SEQ ID NO 2
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
            20                  25                  30

Thr Ser Gly Leu Ile Phe Arg Glu Asp Leu Asp Trp Pro Pro Gly Ser
        35                  40                  45

Pro Gln Glu Pro Leu Cys Leu Val Ala Leu Gly Gly Asp Ser Asn Gly
    50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro
            100                 105                 110

Ser Leu Arg Arg Leu Gly Ala Trp Leu Arg Asp Pro Gly Gly Gln Arg
        115                 120                 125

Leu Val Val Leu His Leu Glu Glu Val Thr Trp Glu Pro Thr Pro Ser
    130                 135                 140

Leu Arg Phe Gln Glu Pro Pro Gly Gly Ala Gly Pro Pro Glu Leu
145                 150                 155                 160

Ala Leu Leu Val Leu Tyr Pro Gly Pro Gly Pro Glu Val Thr Val Thr
                165                 170                 175

Arg Ala Gly Leu Pro Gly Ala Gln Ser Leu Cys Pro Ser Arg Asp Thr
            180                 185                 190

Arg Tyr Leu Val Leu Ala Val Asp Arg Pro Ala Gly Ala Trp Arg Gly
        195                 200                 205

Ser Gly Leu Ala Leu Thr Leu Gln Pro Arg Gly Glu Asp Ser Arg Leu
    210                 215                 220

Ser Thr Ala Arg Leu Gln Ala Leu Leu Phe Gly Asp Asp His Arg Cys
225                 230                 235                 240

Phe Thr Arg Met Thr Pro Ala Leu Leu Leu Leu Pro Arg Ser Glu Pro
                245                 250                 255

Ala Pro Leu Pro Ala His Gly Gln Leu Asp Thr Val Pro Phe Pro Pro
            260                 265                 270

Pro Arg Pro Ser Ala Glu Leu Glu Glu Ser Pro Ser Ala Asp Pro
        275                 280                 285

Phe Leu Glu Thr Leu Thr Arg Leu Val Arg Ala Leu Arg Val Pro Pro
    290                 295                 300

Ala Arg Ala Ser Ala Pro Arg Leu Ala Leu Asp Pro Asp Ala Leu Ala
305                 310                 315                 320
```

```
Gly Phe Pro Gln Gly Leu Val Asn Leu Ser Asp Pro Ala Ala Leu Glu
            325                 330                 335

Arg Leu Leu Asp Gly Glu Pro Leu Leu Leu Leu Arg Pro Thr
            340                 345                 350

Ala Ala Thr Thr Gly Asp Pro Ala Pro Leu His Asp Pro Thr Ser Ala
            355                 360                 365

Pro Trp Ala Thr Ala Leu Ala Arg Arg Val Ala Glu Leu Gln Ala
    370                 375                 380

Ala Ala Ala Glu Leu Arg Ser Leu Pro Gly Leu Pro Pro Ala Thr Ala
385                 390                 395                 400

Pro Leu Leu Ala Arg Leu Leu Ala Leu Cys Pro Gly Gly Pro Gly Gly
            405                 410                 415

Leu Gly Asp Pro Leu Arg Ala Leu Leu Leu Lys Ala Leu Gln Gly
            420                 425                 430

Leu Arg Val Glu Trp Arg Gly Arg Asp Pro Arg Gly Pro Gly Arg Ala
            435                 440                 445

Arg Arg Ser Ala Gly Ala Thr Ala Ala Asp Gly Pro Cys Ala Leu Arg
    450                 455                 460

Glu Leu Ser Val Asp Leu Arg Ala Glu Arg Ser Val Leu Ile Pro Glu
465                 470                 475                 480

Thr Tyr Gln Ala Asn Asn Cys Gln Gly Val Cys Gly Trp Pro Gln Ser
            485                 490                 495

Asp Arg Asn Pro Arg Tyr Gly Asn His Val Val Leu Leu Lys Met
            500                 505                 510

Gln Val Arg Gly Ala Ala Leu Ala Arg Pro Pro Cys Cys Val Pro Thr
            515                 520                 525

Ala Tyr Ala Gly Lys Leu Leu Ile Ser Leu Ser Glu Glu Arg Ile Ser
    530                 535                 540

Ala His His Val Pro Asn Met Val Ala Thr Glu Cys Gly Cys Arg
545                 550                 555

<210> SEQ ID NO 3
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
            20                  25                  30

Thr Ser Gly Leu Ile Phe Arg Glu Asp Leu Asp Trp Pro Pro Gly Ser
            35                  40                  45

Pro Gln Glu Pro Leu Cys Leu Val Ala Leu Gly Gly Asp Ser Asn Gly
        50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro
            100                 105                 110

Ser Leu Arg Arg Leu Gly Ala Trp Leu Arg Asp Pro Gly Gly Gln Arg
```

-continued

```
            115                 120                 125
Leu Val Val Leu His Leu Glu Glu Val Thr Trp Glu Pro Thr Pro Ser
    130                 135                 140
Leu Arg Phe Gln Glu Pro Pro Gly Gly Ala Gly Pro Pro Glu Leu
145                 150                 155                 160
Ala Leu Leu Val Leu Tyr Pro Gly Pro Pro Glu Val Thr Val Thr
                    165                 170                 175
Arg Ala Gly Leu Pro Gly Ala Gln Ser Leu Cys Pro Ser Arg Asp Thr
                180                 185                 190
Arg Tyr Leu Val Leu Ala Val Asp Arg Pro Ala Gly Ala Trp Arg Gly
            195                 200                 205
Ser Gly Leu Ala Leu Thr Leu Gln Pro Arg Gly Glu Asp Ser Arg Leu
    210                 215                 220
Ser Thr Ala Arg Leu Gln Ala Leu Leu Phe Gly Asp Asp His Arg Cys
225                 230                 235                 240
Phe Thr Arg Met Thr Pro Ala Leu Leu Leu Pro Arg Ser Glu Pro
                    245                 250                 255
Ala Pro Leu Pro Ala His Gly Gln Leu Asp Thr Val Pro Phe Pro Pro
                260                 265                 270
Pro Arg Pro Ser Ala Glu Leu Glu Glu Ser Pro Pro Ser Ala Asp Pro
            275                 280                 285
Phe Leu Glu Thr Leu Thr Arg Leu Val Arg Ala Leu Arg Val Pro Pro
    290                 295                 300
Ala Arg Ala Ser Ala Pro Arg Leu Ala Leu Asp Pro Asp Ala Leu Ala
305                 310                 315                 320
Gly Phe Pro Gln Gly Leu Val Asn Leu Ser Asp Pro Ala Ala Leu Glu
                    325                 330                 335
Arg Leu Leu Asp Gly Glu Glu Pro Leu Leu Leu Leu Arg Pro Thr
                340                 345                 350
Ala Ala Thr Thr Gly Asp Pro Ala Pro Leu His Asp Pro Thr Ser Ala
            355                 360                 365
Pro Trp Ala Thr Ala Leu Ala Arg Arg Val Ala Ala Glu Leu Gln Ala
    370                 375                 380
Ala Ala Ala Glu Leu Arg Ser Leu Pro Gly Leu Pro Pro Ala Thr Ala
385                 390                 395                 400
Pro Leu Leu Ala Arg Leu Leu Ala Leu Cys Pro Gly Pro Gly Gly
                    405                 410                 415
Leu Gly Asp Pro Leu Arg Ala Leu Leu Leu Lys Ala Leu Gln Gly
                420                 425                 430
Leu Arg Val Glu Trp Arg Gly Arg Asp Pro Arg Gly Pro Gly Arg Ala
            435                 440                 445
Arg Arg Ser Asp Tyr Lys Asp Asp Asp Lys Ala Gly Ala Thr Ala
    450                 455                 460
Ala Asp Gly Pro Cys Ala Leu Arg Glu Leu Ser Val Asp Leu Arg Ala
465                 470                 475                 480
Glu Arg Ser Val Leu Ile Pro Glu Thr Tyr Gln Ala Asn Asn Cys Gln
                    485                 490                 495
Gly Val Cys Gly Trp Pro Gln Ser Asp Arg Asn Pro Arg Tyr Gly Asn
                500                 505                 510
His Val Val Leu Leu Leu Lys Met Gln Val Arg Gly Ala Ala Leu Ala
            515                 520                 525
Arg Pro Pro Cys Cys Val Pro Thr Ala Tyr Ala Gly Lys Leu Leu Ile
    530                 535                 540
```

Ser Leu Ser Glu Glu Arg Ile Ser Ala His His Val Pro Asn Met Val
545                 550                 555                 560

Ala Thr Glu Cys Gly Cys Arg
            565

<210> SEQ ID NO 4
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | | | | |
|---|---|---|---|---|
| atgaagtggg | tgagcttcat | cagcctgctg | ttcctgttca | gcagcgctta ctcccgcggt | 60 |
| gtgttccgcc | gcagagcaga | ggagccagct | gtgggcacca | gtggcctcat cttccgagaa | 120 |
| gacttggact | ggcctccagg | cagcccacaa | gagcctctgt | gcctggtggc actgggcggg | 180 |
| gacagcaatg | gcagcagctc | cccctgcgg | gtggtggggg | ctctaagcgc ctatgagcag | 240 |
| gccttcctgg | gggccgtgca | gagggcccgc | tggggccccc | gagacctggc caccttcggg | 300 |
| gtctgcaaca | ccggtgacag | gcaggctgcc | ttgccctctc | tacggcggct gggggcctgg | 360 |
| ctgcgggacc | ctgggggca | gcgcctggtg | gtcctacacc | tggaggaagt gacctgggag | 420 |
| ccaacaccct | cgctgaggtt | ccaggagccc | ccgcctggag | gagctggccc ccagagctg | 480 |
| gcgctgctgg | tgctgtaccc | tgggcctggc | cctgaggtca | ctgtgacgag ggctgggctg | 540 |
| ccgggtgccc | agagcctctg | cccctcccga | gacacccgct | acctggtgtt agcggtggac | 600 |
| cgccctgcgg | gggcctggcg | cggctccggg | ctggccttga | ccctgcagcc ccgcggagag | 660 |
| gactcccggc | tgagtaccgc | ccggctgcag | gcactgctgt | cggcgacga ccaccgctgc | 720 |
| ttcacacgga | tgaccccggc | cctgctcctg | ctgccgcggt | ccgagcccgc gccgctgcct | 780 |
| gcgcacggc | agctggacac | cgtgcccttc | ccgccgccca | ggccatccgc ggaactcgag | 840 |
| gagtcgccac | ccagcgcaga | ccccttcctg | gagacgctca | cgcgcctggt gcgggcgctg | 900 |
| cgggtccccc | cggcccgggc | ctccgcgccg | cgcctggccc | tggatccgga cgcgctggcc | 960 |
| ggcttcccgc | agggcctagt | caacctgtcg | gaccccgcgg | cgctggagcg cctactcgac | 1020 |
| ggcgaggagc | gcctgctgct | gctgctgagg | cccactgcgg | ccaccaccgg ggatcctgcg | 1080 |
| cccctgcacg | accccacgtc | ggcgccgtgg | gccacggccc | tggcgcgccg cgtggctgct | 1140 |
| gaactgcaag | cggcggctgc | cgagctgcga | agcctcccgg | gtctgcctcc ggccacagcc | 1200 |
| ccgctgctgg | cgcgcctgct | cgcgctctgc | ccaggtggcc | ccggcggcct cggcgatccc | 1260 |
| ctgcgagcgc | tgctgctcct | gaaggcgctg | cagggcctgc | gcgtggagtg gcgcgggcgg | 1320 |
| gatccgcgcg | ggccgggtcg | ggcacggcgc | agcgcggggg | ccaccgccgc cgacgggccg | 1380 |
| tgcgcgctgc | gcgagctcag | cgtagacctc | cgcgccgagc | gctccgtact catccccgag | 1440 |
| acctaccagg | ccaacaattg | ccagggcgtg | tgcggctggc | ctcagtccga ccgcaacccg | 1500 |
| cgctacggca | accacgtggt | gctgctgctg | aagatgcagg | cccgtggggc cgccctggcg | 1560 |
| cgcccacccct | gctgcgtgcc | caccgcctac | gcgggcaagc | tgctcatcag cctgtcggag | 1620 |
| gagcgcatca | gcgcgcacca | cgtgcccaac | atggtggcca | ccgagtgtgg ctgccggtga | 1680 |

<210> SEQ ID NO 5
<211> LENGTH: 1704
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atgaagtggg tgagcttcat cagcctgctg ttcctgttca gcagcgctta ctcccgcggt      60
gtgttccgcc gcagagcaga ggagccagct gtgggcacca gtggcctcat cttccgagaa    120
gacttggact ggcctccagg cagcccacaa gagcctctgt gcctggtggc actgggcggg    180
gacagcaatg gcagcagctc ccccctgcgg gtggtggggg ctctaagcgc ctatgagcag    240
gccttcctgg gggccgtgca gagggcccgc tggggccccc gagacctggc caccttcggg    300
gtctgcaaca ccggtgacag gcaggctgcc ttgccctctc tacggcggct ggggggcctgg    360
ctgcgggacc ctggggggca gcgcctggtg gtcctacacc tggaggaagt gacctgggag    420
ccaacaccct cgctgaggtt ccaggagccc ccgcctggag gagctggccc ccagagctg      480
gcgctgctgg tgctgtaccc tgggcctggc cctgaggtca ctgtgacgag ggctgggctg    540
ccgggtgccc agagcctctg cccctcccga gacacccgct acctggtgtt agcggtggac    600
cgccctgcgg gggcctggcg cggctccggg ctggccttga ccctgcagcc ccgcggagag    660
gactcccggc tgagtaccgc ccggctgcag gcactgctgt cggcgacga ccaccgctgc      720
ttcacacgga tgaccccggc cctgctcctg ctgccgcggt ccgagcccgc gccgctgcct    780
gcgcacggcc agctggacac cgtgcccttc ccgccgccca ggccatccgc ggaactcgag    840
gagtcgccac cagcgcaga ccccttcctg gagacgctca cgcgcctggt gcgggcgctg      900
cgggtccccc cggcccgggc ctccgcgccg cgcctggccc tggatccgga cgcgctggcc    960
ggcttcccgc agggcctagt caacctgtcg accccgcgg cgctggagcg cctactcgac    1020
ggcgaggagc cgctgctgct gctgctgagg cccactgcgg ccaccaccgg ggatcctgcg    1080
cccctgcacg accccacgtc ggcgccgtgg ccacggccc tggcgcgccg cgtggctgct    1140
gaactgcaag cggcggctgc cgagctgcga agcctcccgg gtctgcctcc ggccacagcc    1200
ccgctgctgg cgcgcctgct cgcgctctgc ccaggtggcc ccggcggcct cggcgatccc    1260
ctgcgagcgc tgctgctcct gaaggcgctg cagggcctgc gcgtggagtg gcgcgggcgg    1320
gatccgcgcg ggccgggtcg ggcacggcgc agcgactaca aggatgacga cgacaaggcg    1380
ggggccaccg ccgccgacgg gccgtgcgcg ctgcgcgagc tcagcgtaga cctccgcgcc    1440
gagcgctccg tactcatccc cgagacctac caggccaaca attgccaggg cgtgtgcggc    1500
tggcctcagt ccgaccgcaa cccgcgctac ggcaaccacg tggtgctgct gctgaagatg    1560
caggcccgtg gggccgccct ggcgcgccca ccctgctgcg tgcccaccgc ctacgcgggc    1620
aagctgctca tcagcctgtc ggaggagcgc atcagcgcgc accacgtgcc caacatggtg    1680
gccaccgagt gtggctgccg gtga                                          1704
```

<210> SEQ ID NO 6
<211> LENGTH: 24
<212> TYPE: PRT
<213> ORGANISM: Homo sapiens

<400> SEQUENCE: 6

Met Lys Trp Val Thr Phe Ile Ser Leu Leu Phe Leu Phe Ser Ser Ala
1               5                   10                  15

Tyr Ser Arg Gly Val Phe Arg Arg
            20

```
<210> SEQ ID NO 7
<211> LENGTH: 78
<212> TYPE: DNA
<213> ORGANISM: Homo sapiens

<400> SEQUENCE: 7
atgaagtggg tgagcttcat cagcctgctg ttcctgttca gcagcgctta ctcccgcggt    60
gtgttccgcc gcagagca                                                  78

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Tyr Lys Asp Asp Asp Asp Lys
1               5

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gactacaagg atgacgacga caag                                           24

<210> SEQ ID NO 10
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Glu Leu Val Pro Arg Gly Ser Gly Asp Pro Ile Glu Gly Arg Gly
1               5                   10                  15

Gly Gly Gly Gly Asp Pro Lys Ser Cys Asp Lys Pro His Thr Cys Pro
            20                  25                  30

Leu Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160
```

```
Asp Glu Leu Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
        180                 185                 190

Glu Asn Asn Tyr Lys Ala Thr Pro Pro Val Leu Asp Ser Asp Gly Ser
    195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
            245                 250

<210> SEQ ID NO 11
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
cgagatacat gaagtgggtg agcttcatca gcctgctgtt cctgttcagc agcgcttact    60
cccgcggtgt gttccggcgc agagcagagg agccagctgt g                      101

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctcctggaa cctcagcgag                                                20

<210> SEQ ID NO 13
<211> LENGTH: 18
<212> TYPE: PRT
<213> ORGANISM: Homo sapiens

<400> SEQUENCE: 13

Met Lys Trp Val Thr Phe Ile Ser Leu Leu Phe Leu Phe Ser Ser Ala
1               5                   10                  15

Tyr Ser

<210> SEQ ID NO 14
<211> LENGTH: 18
<212> TYPE: PRT
<213> ORGANISM: Homo sapiens

<400> SEQUENCE: 14

Met Lys Trp Val Ser Phe Ile Ser Leu Leu Phe Leu Phe Ser Ser Ala
1               5                   10                  15

Tyr Ser

<210> SEQ ID NO 15
<211> LENGTH: 21
<212> TYPE: PRT
<213> ORGANISM: Unknown
<220> FEATURE:
<223> OTHER INFORMATION: Description of Unknown: MPIF-1
``` signal sequence

<400> SEQUENCE: 15

Met Lys Val Ser Val Ala Ala Leu Ser Cys Leu Met Leu Val Thr Ala
1               5                   10                  15

Leu Gly Ser Gln Ala
            20

<210> SEQ ID NO 16
<211> LENGTH: 17
<212> TYPE: PRT
<213> ORGANISM: Unknown
<220> FEATURE:
<223> OTHER INFORMATION: Description of Unknown: Stanniocalcin
      signal sequence

<400> SEQUENCE: 16

Met Leu Gln Asn Ser Ala Val Leu Leu Leu Val Ile Ser Ala Ser
1               5                   10                  15

Ala

<210> SEQ ID NO 17
<211> LENGTH: 19
<212> TYPE: PRT
<213> ORGANISM: Unknown
<220> FEATURE:
<223> OTHER INFORMATION: Description of Unknown: Invertase
      signal sequence

<400> SEQUENCE: 17

Met Leu Leu Gln Ala Phe Leu Phe Leu Leu Ala Gly Phe Ala Ala Lys
1               5                   10                  15

Ile Ser Ala

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Lys Trp Val Ser Phe Ile Ser Leu Leu Phe Leu Phe Ser Ser Ala
1               5                   10                  15

Tyr Ser Arg Ser Leu Glu Lys Arg
            20

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Lys Trp Val Ser Phe Ile Ser Leu Leu Phe Leu Phe Ser Ser Ala
1               5                   10                  15

Tyr Ser Arg Ser Leu Asp Lys Arg
            20

<210> SEQ ID NO 20
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Asn Ile Phe Tyr Ile Phe Leu Phe Leu Leu Ser Phe Val Gln Gly
1               5                   10                  15

Ser Leu Asp Lys Arg
            20

<210> SEQ ID NO 21
<211> LENGTH: 19
<212> TYPE: PRT
<213> ORGANISM: Unknown
<220> FEATURE:
<223> OTHER INFORMATION: Description of Unknown: Immunoglobulin
      Ig signal sequence

<400> SEQUENCE: 21

Met Gly Trp Ser Cys Ile Ile Leu Phe Leu Val Ala Thr Ala Thr Gly
1               5                   10                  15

Val His Ser

<210> SEQ ID NO 22
<211> LENGTH: 29
<212> TYPE: PRT
<213> ORGANISM: Unknown
<220> FEATURE:
<223> OTHER INFORMATION: Description of Unknown: Fibulin B
      precursor signal sequence

<400> SEQUENCE: 22

Met Glu Arg Ala Ala Pro Ser Arg Arg Val Pro Leu Pro Leu Leu Leu
1               5                   10                  15

Leu Gly Gly Leu Ala Leu Leu Ala Ala Gly Val Asp Ala
            20                  25

<210> SEQ ID NO 23
<211> LENGTH: 22
<212> TYPE: PRT
<213> ORGANISM: Unknown
<220> FEATURE:
<223> OTHER INFORMATION: Description of Unknown: Clusterin
      precursor signal sequence

<400> SEQUENCE: 23

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 24
<211> LENGTH: 21
<212> TYPE: PRT
<213> ORGANISM: Unknown
<220> FEATURE:
<223> OTHER INFORMATION: Description of Unknown: Insulin-like
      growth factor-binding protein 4 signal sequence

<400> SEQUENCE: 24

Met Leu Pro Leu Cys Leu Val Ala Ala Leu Leu Leu Ala Ala Gly Pro
1               5                   10                  15

Gly Pro Ser Leu Gly
```

```
<210> SEQ ID NO 25
<211> LENGTH: 25
<212> TYPE: PRT
<213> ORGANISM: Homo sapiens

<400> SEQUENCE: 25

Met Arg Asp Leu Pro Leu Thr Ser Leu Ala Leu Val Leu Ser Ala Leu
1               5                   10                  15

Gly Ala Leu Leu Gly Thr Glu Ala Leu
            20                  25

<210> SEQ ID NO 26
<211> LENGTH: 5
<212> TYPE: PRT
<213> ORGANISM: Homo sapiens

<400> SEQUENCE: 26

Arg Ala Gln Arg Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Arg Arg Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Gln Arg Arg
1               5
```